(12) United States Patent
Lai

(10) Patent No.: US 8,709,774 B2
(45) Date of Patent: Apr. 29, 2014

(54) SPERM FACTOR SEQUENCES

(75) Inventor: Francis Anthony Lai, Cardiff (GB)

(73) Assignee: University College Cardiff Consultants Limited, Cardiff (GB)

(*) Notice: Subject to any disclaimer, the term of this patent is extended or adjusted under 35 U.S.C. 154(b) by 952 days.

(21) Appl. No.: 12/122,056

(22) Filed: May 16, 2008

(65) Prior Publication Data

US 2008/0289057 A1 Nov. 20, 2008

Related U.S. Application Data

(63) Continuation-in-part of application No. 10/493,927, filed as application No. PCT/GB02/04739 on Oct. 18, 2002, now abandoned.

(30) Foreign Application Priority Data

Oct. 24, 2001 (GB) .................................. 0125498.6
Jun. 28, 2002 (GB) .................................. 0214945.8

(51) Int. Cl.
*C12N 9/20* (2006.01)
*C12Q 1/68* (2006.01)
*C12Q 1/44* (2006.01)
*C07H 21/04* (2006.01)

(52) U.S. Cl.
USPC ............ 435/198; 435/6.18; 435/19; 536/23.2

(58) Field of Classification Search
None
See application file for complete search history.

(56) References Cited

FOREIGN PATENT DOCUMENTS

| WO | WO 96/25495 | 8/1996 |
| WO | WO 02/06302 | 1/2002 |

OTHER PUBLICATIONS

Nucleic acid and amino acid sequence Alignment of SEQ ID No. 1 and 3 with the nucleic acid and amino acid sequence of Mayers et al.*
Wu et al. Sperm factor induces intracellular free calcium oscillations by stimulating the phosphoinositide pathway. Biology of Reproduction 64. 2001; pp. 1338-1349.
Sha et al. NYD-SP27: a novel human testis development gene. 2001. Database EMBL 'Online! retrieved from EMBL Database accession No. AY035866 XP 002238168.
Adachi et al. Mus musculus adult male testis CDNA, Riken full length . . . 2001. Database EMBL xOnline!; retrieved from EMBL Database accession N. AKD06672;XP 002238169.
Saunders et al. PLCC: a sperm-specific trigger of Ca2+ oscillations in eggs and embryo development. Development 129. 2002. pp. 3533-3544.
Database Genbank, Database Accession No. AB070108, 2001.
Database Genbank, Database Accession No. AB070109, 2001.

* cited by examiner

*Primary Examiner* — Iqbal H Chowdhury
(74) *Attorney, Agent, or Firm* — King & Schickli, PLLC

(57) ABSTRACT

A nucleic acid sequence, including an isolated, purified or recombinant nucleic acid sequence, includes: (a) a nucleic acid sequence encoding a polypeptide encompassed by the present invention, namely, a PLC-zeta; PLCζ amino acid sequence, capable of triggering calcium oscillations in oocytes; (b) a sequence substantially homologous to or that hybridizes to sequence (a) under stringent conditions; (c) a sequence substantially homologous to or that hybridizes to the sequences (a) or (b) but for degeneracy of the genetic code; and (d) an oligonucleotide specific for any of the sequences (a), (b) or (c) above.

3 Claims, 23 Drawing Sheets

Expression of mouse PLC-zeta in CHO cells

Plot of calcium concentration (nM; ordinate) with time (secs; abscissa)

Expression of mouse PLC-zeta complementary RNA by micro-injection into Mouse Eggs Plot of calcium concentration (ordinate) with time (abscissa)

Schematic Alignment of PLC Regions

Activation and Embryo Development to Blastocyst in
$^{D210R}$ PLC-zeta-injected Mouse Eggs Pipette concentration of PLCζ (µg/ml)

a) Luminescence    b) Time course of expression a) Cell number in blastocysts b) Cell distribution in blastocysts c) Differentiation staining a) Image of luminescence b) Development rate

PLCζ-luc expression in human oocytes.

a)

b)

SEQUENCE LISTING

```
<160> NUMBER OF SEQ ID NOS: 28

<210> SEQ ID NO 1
<211> LENGTH: 608
<212> TYPE: PRT
<213> ORGANISM: Human

<400> SEQUENCE: 1

Met Glu Met Arg Trp Phe Leu Ser Lys Ile Gln Asp Asp Phe Arg Gly
1               5                   10                  15

Gly Lys Ile Asn Leu Glu Lys Thr Gln Arg Leu Leu Glu Lys Leu Asp
            20                  25                  30

Ile Arg Cys Ser Tyr Ile His Val Lys Gln Ile Phe Lys Asp Asn Asp
        35                  40                  45

Arg Leu Lys Gln Gly Arg Ile Thr Ile Glu Glu Phe Arg Ala Ile Tyr
    50                  55                  60

Arg Ile Ile Thr His Arg Glu Glu Ile Ile Glu Ile Phe Asn Thr Tyr
65                  70                  75                  80

Ser Glu Asn Arg Lys Ile Leu Leu Ala Ser Asn Leu Ala Gln Phe Leu
                85                  90                  95

Thr Gln Glu Gln Tyr Ala Ala Glu Met Ser Lys Ala Ile Ala Phe Glu
            100                 105                 110

Ile Ile Gln Lys Tyr Glu Pro Ile Glu Glu Val Arg Lys Ala His Gln
        115                 120                 125

Met Ser Leu Glu Gly Phe Thr Arg Tyr Met Asp Ser Arg Glu Cys Leu
    130                 135                 140
```

```
Leu Phe Lys Asn Glu Cys Arg Lys Val Tyr Gln Asp Met Thr His Pro
145                 150                 155                 160

Leu Asn Asp Tyr Phe Ile Ser Ser His Asn Thr Tyr Leu Val Ser
            165                 170                 175

Asp Gln Leu Leu Gly Pro Ser Asp Leu Trp Gly Tyr Val Ser Ala Leu
        180                 185                 190

Val Lys Gly Cys Arg Cys Leu Glu Ile Asp Cys Trp Asp Gly Ala Gln
            195                 200                 205

Asn Glu Pro Val Val Tyr His Gly Tyr Thr Leu Thr Ser Lys Leu Leu
        210                 215                 220

Phe Lys Thr Val Ile Gln Ala Ile His Lys Tyr Ala Phe Met Thr Ser
225                 230                 235                 240

Asp Tyr Pro Val Val Leu Ser Leu Glu Asn His Cys Ser Thr Ala Gln
            245                 250                 255

Gln Glu Val Met Ala Asp Asn Leu Gln Ala Thr Phe Gly Glu Ser Leu
            260                 265                 270

Leu Ser Asp Met Leu Asp Asp Phe Pro Asp Thr Leu Pro Ser Pro Glu
        275                 280                 285

Ala Leu Lys Phe Lys Ile Leu Val Lys Asn Lys Lys Ile Gly Thr Leu
        290                 295                 300

Lys Glu Thr His Glu Arg Lys Gly Ser Asp Lys Arg Gly Asp Asn Gln
305                 310                 315                 320

Asp Lys Glu Thr Gly Val Lys Lys Leu Pro Gly Val Met Leu Phe Lys
            325                 330                 335

Lys Lys Lys Thr Arg Lys Leu Lys Ile Ala Leu Ala Leu Ser Asp Leu
            340                 345                 350

Val Ile Tyr Thr Lys Ala Glu Lys Phe Lys Ser Phe Gln His Ser Arg
        355                 360                 365

Leu Tyr Gln Gln Phe Asn Glu Asn Asn Ser Ile Gly Glu Thr Gln Ala
        370                 375                 380

Arg Lys Leu Ser Lys Leu Arg Val His Glu Phe Ile Phe His Thr Arg
385                 390                 395                 400

Lys Phe Ile Thr Arg Ile Tyr Pro Lys Ala Thr Arg Ala Asp Ser Ser
            405                 410                 415

Asn Phe Asn Pro Gln Glu Phe Trp Asn Ile Gly Cys Gln Met Val Ala
            420                 425                 430

Leu Asn Phe Gln Thr Pro Gly Leu Pro Met Asp Leu Gln Asn Gly Lys
            435                 440                 445

Phe Leu Asp Asn Gly Gly Ser Gly Tyr Ile Leu Lys Pro His Phe Leu
        450                 455                 460

Arg Glu Ser Lys Ser Tyr Phe Asn Pro Ser Asn Ile Lys Glu Gly Met
465                 470                 475                 480

Pro Ile Thr Leu Thr Ile Arg Leu Ile Ser Gly Ile Gln Leu Pro Leu
            485                 490                 495

Thr His Ser Ser Ser Asn Lys Gly Asp Ser Leu Val Ile Ile Glu Val
            500                 505                 510

Phe Gly Val Pro Asn Asp Gln Met Lys Gln Gln Thr Arg Val Ile Lys
        515                 520                 525

Lys Asn Ala Phe Ser Pro Arg Trp Asn Glu Thr Phe Thr Phe Ile Ile
        530                 535                 540

His Val Pro Glu Leu Ala Leu Ile Arg Phe Val Val Glu Gly Gln Gly
545                 550                 555                 560

Leu Ile Ala Gly Asn Glu Phe Leu Gly Gln Tyr Thr Leu Pro Leu Leu
```

```
              565                 570                 575
Cys Met Asn Lys Gly Tyr Arg Arg Ile Pro Leu Phe Ser Arg Met Gly
            580                 585                 590

Glu Ser Leu Glu Pro Ala Ser Leu Phe Val Tyr Val Trp Tyr Val Arg
            595                 600                 605

<210> SEQ ID NO 2
<211> LENGTH: 647
<212> TYPE: PRT
<213> ORGANISM: Mouse

<400> SEQUENCE: 2

Met Glu Ser Gln Leu His Glu Leu Ala Glu Ala Arg Trp Phe Leu Ser
1               5                   10                  15

Lys Val Gln Asp Asp Phe Arg Gly Gly Lys Ile Asn Val Glu Ile Thr
            20                  25                  30

His Lys Leu Leu Glu Lys Leu Asp Phe Pro Cys His Phe Ala His Val
        35                  40                  45

Lys His Ile Phe Lys Glu Asn Asp Arg Gln Asn Gln Gly Arg Ile Thr
    50                  55                  60

Ile Glu Glu Phe Arg Ala Ile Tyr Arg Cys Ile Val His Arg Glu Glu
65                  70                  75                  80

Ile Thr Glu Ile Phe Asn Thr Tyr Thr Glu Asn Arg Lys Ile Leu Ser
                85                  90                  95

Glu Asn Ser Leu Ile Glu Phe Leu Thr Gln Glu Gln Tyr Glu Met Glu
            100                 105                 110

Ile Asp His Ser Asp Ser Val Glu Ile Ile Asn Lys Tyr Glu Pro Ile
        115                 120                 125

Glu Glu Val Lys Gly Glu Arg Gln Met Ser Ile Glu Gly Phe Ala Arg
    130                 135                 140

Tyr Met Phe Ser Ser Glu Cys Leu Leu Phe Lys Glu Asn Cys Lys Thr
145                 150                 155                 160

Val Tyr Gln Asp Met Asn His Pro Leu Ser Asp Tyr Phe Ile Ser Ser
                165                 170                 175

Ser His Asn Thr Tyr Leu Ile Ser Asp Gln Ile Leu Gly Pro Ser Asp
            180                 185                 190

Ile Trp Gly Tyr Val Ser Ala Leu Val Lys Gly Cys Arg Cys Leu Glu
        195                 200                 205

Ile Asp Cys Trp Asp Gly Ser Gln Asn Glu Pro Ile Val Tyr His Gly
    210                 215                 220

Tyr Thr Phe Thr Ser Lys Leu Leu Phe Lys Thr Val Val Gln Ala Ile
225                 230                 235                 240

Asn Lys Tyr Ala Phe Val Thr Ser Asp Tyr Pro Val Val Leu Ser Leu
                245                 250                 255

Glu Asn His Cys Ser Pro Gly Gln Gln Glu Val Met Ala Ser Ile Leu
            260                 265                 270

Gln Ser Thr Phe Gly Asp Phe Leu Leu Ser Asp Met Leu Glu Glu Phe
        275                 280                 285

Pro Asp Thr Leu Pro Ser Pro Glu Ala Leu Lys Phe Lys Ile Leu Val
    290                 295                 300

Lys Asn Arg Lys Val Gly Thr Leu Ser Glu Thr His Glu Arg Ile Gly
305                 310                 315                 320

Thr Asp Lys Ser Gly Gln Val Leu Glu Trp Lys Glu Val Ile Tyr Glu
                325                 330                 335

Asp Gly Asp Glu Asp Ser Gly Met Asp Pro Glu Thr Trp Asp Val Phe
```

-continued

```
                     340                 345                 350
Leu Ser Arg Ile Lys Glu Glu Arg Glu Ala Asp Pro Ser Thr Leu Ser
                355                 360                 365
Gly Ile Ala Gly Val Lys Lys Arg Lys Arg Lys Met Lys Ile Ala Met
            370                 375                 380
Ala Leu Ser Asp Leu Val Ile Tyr Thr Lys Ala Glu Lys Phe Arg Asn
385                 390                 395                 400
Phe Gln Tyr Ser Arg Val Tyr Gln Gln Phe Asn Glu Thr Asn Ser Ile
                405                 410                 415
Gly Glu Ser Arg Ala Arg Lys Leu Ser Lys Leu Arg Val His Glu Phe
            420                 425                 430
Ile Phe His Thr Ala Ala Phe Ile Thr Arg Val Tyr Pro Lys Met Met
        435                 440                 445
Arg Ala Asp Ser Ser Asn Phe Asn Pro Gln Glu Phe Trp Asn Val Gly
    450                 455                 460
Cys Gln Met Val Ala Leu Asn Phe Gln Thr Pro Gly Leu Pro Met Asp
465                 470                 475                 480
Leu Gln Asn Gly Lys Phe Leu Asp Asn Gly Gly Ser Gly Tyr Ile Leu
                485                 490                 495
Lys Pro Asp Ile Leu Arg Asp Thr Thr Leu Gly Phe Asn Pro Asn Glu
            500                 505                 510
Pro Glu Tyr Asp Asp His Pro Val Thr Leu Thr Ile Arg Ile Ile Ser
        515                 520                 525
Gly Ile Gln Leu Pro Val Ser Ser Ser Asn Thr Pro Asp Ile Val
    530                 535                 540
Val Ile Ile Glu Val Tyr Gly Val Pro Asn Asp His Val Lys Gln Gln
545                 550                 555                 560
Thr Arg Val Val Lys Asn Asn Ala Phe Ser Pro Lys Trp Asn Glu Thr
                565                 570                 575
Phe Thr Phe Leu Ile Gln Val Pro Glu Leu Ala Leu Ile Arg Phe Val
            580                 585                 590
Val Glu Thr Gln Gln Gly Leu Leu Ser Gly Asn Glu Leu Leu Gly Gln
        595                 600                 605
Tyr Thr Leu Pro Val Leu Cys Met Asn Lys Gly Tyr Arg Arg Val Pro
    610                 615                 620
Leu Phe Ser Lys Ser Gly Ala Asn Leu Glu Pro Ser Ser Leu Phe Ile
625                 630                 635                 640
Tyr Val Trp Tyr Phe Arg Glu
                645

<210> SEQ ID NO 3
<211> LENGTH: 1827
<212> TYPE: DNA
<213> ORGANISM: Human

<400> SEQUENCE: 3
atggaaatga  datggttttt  gtcaaagatt  caggatgact  tcagaggtgg  aaaaattaac    60
ctagaaaaaa  ctcagaggtt  acttgaaaaa  ttagatattc  ggtgcagtta  tattcatgtg   120
aaacagattt  ttaaggacaa  tgacaggctg  aaacaaggaa  gaatcaccat  agaagaattt   180
agagcaattt  atcgaattat  cacgcacaga  agagaaatta  ttgagatttt  caacacatat   240
tctgaaaacc  ggaaaattct  tttagcaagt  aatctggctc  aatttctgac  acaagaacaa   300
tatgcagctg  agatgagtaa  agctattgct  tttgagatca  ttcagaaata  cgagcctatc   360
gaagaagtta  ggaaagcaca  ccaaatgtca  ttagaaggtt  ttacaagata  catggattca   420
```

-continued

```
cgtgaatgtc tactgtttaa aaatgaatgt agaaaagttt atcaagatat gactcatcca    480
ttaaatgatt attttatttc atcttcacat aacacatatt tggtatctga tcaattattg    540
ggaccaagtg acctttgggg atatgtaagt gcccttgtga aaggatgccg ttgtttggag    600
attgactgct gggatggagc acaaaatgaa cctgttgtat atcatggcta cacactcaca    660
agcaaacttc tgtttaaaac tgttatccaa gctatacaca agtatgcatt catgacatct    720
gactacccag tggtgctctc tttagaaaat cactgctcca ctgcccaaca agaagtaatg    780
gcagacaatt gcaggctac ttttggagag tccttgcttt ctgatatgct tgatgatttt    840
cctgatactc taccatcacc agaggcacta aaattcaaaa tattagttaa aaataagaaa    900
ataggaacct taaaggaaac ccatgaaaga aaaggttctg ataagcgtgg agacaatcaa    960
gacaaggaaa cagggtaaa aaagttacct ggagtaatgc ttttcaagaa aaagaagacc   1020
aggaagctaa aaattgctct ggccttatct gatcttgtca tttatacgaa agctgagaaa   1080
ttcaaaagct tcaacattc aagattatat cagcaattta atgaaaataa ttctattggg   1140
gagacacaag cccgaaaact ttcaaaattg cgagtccatg agtttatttt tcacaccagg   1200
aagttcatta ccagaatata tcccaaagca acaagagcag actcttctaa ttttaatccc   1260
caagaatttt ggaatatagg ttgtcaaatg gtggctttaa atttccagac ccctggtctg   1320
cccatggatc tgcaaaatgg gaaattttg gataatggtg ttctggata tattttgaaa    1380 ccacatttct aagagagag taaatcatac tttaacccaa gtaacataaa agagggtatg   1440
ccaattacac ttcaataag gctcatcagt ggtatccagt tgcctcttac tcattcatca    1500
tctaacaaag gtgattcatt agtaattata gaagttttg gtgttccaaa tgatcaaatg   1560
aagcagcaga ctcgtgtaat taaaaaaaat gcttttagtc caagatggaa tgaaacattc   1620
acatttatta ttcatgtccc agaattggca ttgatacgtt tgttgttga aggtcaaggt   1680 ttaatagcag gaaatgaatt tcttgggcaa tatactttgc cacttctatg catgaacaaa   1740
ggttatcgtc gtattcctct gttttccaga atgggtgaga gccttgagcc tgcttcactg   1800
tttgtttatg tttggtacgt cagataa                                       1827
```

<210> SEQ ID NO 4
<211> LENGTH: 1944
<212> TYPE: DNA
<213> ORGANISM: Mouse

<400> SEQUENCE: 4

```
atggaaagcc aacttcatga gctcgcagaa gcaagatggt ttttgtcaaa ggttcaggat     60
gattttagag gtggaaaaat caacgttgaa attactcaca aactgcttga aaacttgat    120 ttcccatgcc actttgctca tgtgaaacat attttaagg aaaatgacag acagaaccaa    180
ggaagaatca ccattgaaga gtttagagcc atttaccggt gtattgtaca tagagaagaa    240
atcacggaga ttttcaacac gtatactgaa ataggaaaa ttctttctga aacagtctg    300 attgagtttc taacccaaga gcagtatgaa atggagatcg atcactctga ttcagtagag    360
atcatcaata gtatgagcc tattgaagaa gtaaaggtg agcgacagat gtcaattgaa    420
ggtttcgcaa gatacatgtt ttcatcagaa tgtctactgt ttaaagagaa ctgtaaaacc    480
gtgtaccaag atatgaatca tccattaagt gattatttta tttcatcatc tcacaacaca    540
tatttgatat ccgatcaaat attgggaccg agtgacattt ggggatatgt aagtgctctt    600
gtgaaaggct gccgctgtct ggaaattgac tgctgggatg atcccaaaa tgagcccatt    660 gtgtaccatg gttacacatt caccagcaag cttctcttca aaactgtggt ccaagcaata    720
```

```
aacaagtatg cctttgtgac atctgattac ccagtagtgc tgtccttaga aaatcactgc    780 tccctggtc   agcaggaagt gatggctagc attctgcaga gcacctttgg agacttcctg    840
ctttcggaca tgcttgagga gtttccagat acactaccgt ctccagaggc actaaaattc    900
aaaatattag tgaaaaacag gaaagtggga accttatctg aaacccacga gaggatagga    960
accgacaaaa gtggccaagt gctagaatgg aaagaagtca tctatgaaga tggtgatgaa   1020
gactcaggaa tggatccaga acatgggat gtcttcctat cacggatcaa ggaggagagg    1080
gaagcagatc cctcgacatt gagtggaata gcaggcgtca agaaaaggaa gaggaagatg   1140
aaaatagcca tggccttatc tgatcttgtc atttatacta aggctgagaa gttccgaaac   1200
ttccaatatt caagagtcta tcagcaattt aatgagacca attcgattgg agagtctcga   1260
gctcgaaaac tttccaaatt gagagtccat gagtttattt ccacaccgc ggcattcatc    1320 accagagtat accccaaaat gatgagagca gactcttcta actttaaccc tcaagagttt   1380
tggaatgtag gatgtcagat ggtggccttg aactttcaaa cccctggact gcctatggat   1440
ttgcaaaacg ggaatttttt ggataatgga ggctctggat atattttgaa gccagacatc   1500
cttagagata caaccctggg ctttaaccca atgaaccag aatatgacga ccatccagtt    1560
accctcacaa tccgaatcat cagtgggatc cagttgcctg ttagctcatc ctctaacacg   1620
cctgacatag tagtgatcat agaagtctac ggtgttccaa cgaccacgt gaagcagcag    1680 actcgtgttg ttaagaataa tgcttttagt ccaaagtgga tgaaacatt tacatttctt    1740 attcaagtgc cagaactggc attgatacgt tttgttgttg aaactcaaca aggcttatta   1800
tcaggaaatg aattactcgg gcagtacact ttaccagttc tttgcatgaa caaaggttat   1860
cgtcgtgttc ctctgttttc caaatccggt gcgaaccttg aaccttcctc actgtttatt   1920
tatgtttggt acttcagaga gtga                                          1944
```

<210> SEQ ID NO 5
<211> LENGTH: 2186
<212> TYPE: DNA
<213> ORGANISM: Mouse

<400> SEQUENCE: 5

```
cccccccggc aagccatgcc aactgtgaag gttttaagaa cttagcttct ggacaagttt     60
tcttcgaaag tgaaaagcag tagcagcgag aacagctgat gacggtcaca aaaagacagt    120
gttacttcta agacaagtga cacctttagac gaagagccct ctatgggagg acaagcggcc   180
cagatcatga atcatggaa agccaacttc atgagctcgc agaagcaaga tggttttttgt   240 caaaggttca ggatgatttt agaggtggaa aaatcaacgt tgaaattact cacaaactgc    300
ttgagaaact tgatttccca tgccactttg ctcatgtgaa acatattttt aaggaaaatg    360
acagacagaa ccaaggaaga atcaccattg aagagtttag agccatttac cggtgtattg    420
tacatagaga agaaatcacg gagattttca acacgtatac tgaaaatagg aaaattcttt    480
ctgagaacag tctgattgag tttctaaccc aagagcagta tgaaatggag atcgatcact    540
ctgattcagt agagatcatc aataagtatg agcctattga agaagtaaag ggtgagcgac    600
agatgtcaat tgaaggtttc gcaagataca tgttttcatc agaatgtcta ctgtttaaag    660
agaactgtaa aaccgtgtac caagatatga atcatccatt aagtgattat tttatttcat    720
catctcacaa cacatatttg atatccgatc aaatattggg accgagtgac atttggggat    780
atgtaagtgc tcttgtgaaa ggctgccgct gtctggaaat tgactgctgg gatggatccc    840
aaaatgagcc cattgtgtac catggttaca cattcaccag caagcttctc ttcaaaactg    900
```

```
tggtccaagc aataaacaag tatgcctttg tgacatctga ttacccagta gtgctgtcct      960
tagaaaatca ctgctcccct ggtcagcagg aagtgatggc tagcattctg cagagcacct     1020
ttggagactt cctgctttcg gacatgcttg aggagtttcc agatacacta ccgtctccag     1080
aggcactaaa attcaaaata ttagtgaaaa acaggaaagt gggaacctta tctgaaaccc     1140
acgagaggat aggaaccgac aaaagtggcc aagtgctaga atggaaagaa gtcatctatg     1200
aagatggtga tgaagactca ggaatggatc cagaaacatg ggatgtcttc ctatcacgga     1260
tcaaggagga gagggaagca gatccctcga cattgagtgg aatagcaggc gtcaagaaaa     1320
ggaagaggaa gatgaaaata gccatggcct tatctgatct tgtcatttat actaaggctg     1380
agaagttccg aaacttccaa tattcaagag tctatcagca atttaatgag accaattcga     1440
ttggagagtc tcgagctcga aaactttcca aattgagagt ccatgagttt attttccaca     1500
ccgcggcatt catcaccaga gtataccccca aaatgatgag agcagactct tctaacttta     1560
accctcaaga gttttggaat gtaggatgtc agatggtggc cttgaacttt caaacccctg     1620
gactgcctat ggatttgcaa aacgggaaat ttttggataa tggaggctct ggatatattt     1680
tgaagccaga catccttaga gatacaaccc tgggctttaa cccaaatgaa ccagaatatg     1740
acgaccatcc agttaccctc acaatccgaa tcatcagtgg gatccagttg cctgttagct     1800
catcctctaa cacgcctgac atagtagtga tcatagaagt ctacggtgtt ccaaacgacc     1860
acgtgaagca gcagactcgt gttgttaaga ataatgcttt tagtccaaag tggaatgaaa     1920
catttacatt tcttattcaa gtgccagaac tggcattgat acgttttgtt gttgaaactc     1980
aacaaggctt attatcagga aatgaattac tcgggcagta cactttacca gttctttgca     2040
tgaacaaagg ttatcgtcgt gttcctctgt tttccaaatc cggtgcgaac cttgaacctt     2100
cctcactgtt tatttatgtt tggtacttca gagagtgacg catgtaactg acgcgttagc     2160
tacacatcac agtaaacagt ccaaag                                          2186
```

<210> SEQ ID NO 6
<211> LENGTH: 1920
<212> TYPE: DNA
<213> ORGANISM: Monkey

<400> SEQUENCE: 6

```
atggaaatga atggttttt gtcgaagatt caggatgact ttagaggtgg aaaaattaat       60
ctagaaaaaa ctcagaggtt acttgaaaaa ttagatattc ggtgcagtta tattcatgtg      120
aaacggatat ttaaggacaa tgacaggctg aaacaaggaa gaatcaccat agaagaattt      180
agagcaattt atcgaattct cacgcacaga gaagaaattg ttgagatttt caacgcatat      240
tctgaaaacc ggaaaattct tttagaaaat aatctggttc aatttctgac acaagaacaa      300
tatacaactg agatgagtaa aactattgct tttgagatca ttcagaaaata tgaacctatc      360 gaagaagtta ggaaagcacg ccaaatgtca ttagaaggtt tacaagata tatggattca      420 cgtgaatgtc aactatttaa aaatgaatgt agaaaagttt atcaagatat gactcatcca      480
ttaaatgatt attttatttc atcttcacat aacacatatt tggtatctga tcaattagtg      540
ggaccaagtg acctttgggg atatgtaagt gcccttgtga aaggatgccg ttgtttggag      600
attgattgct gggatggagc acaaaatgaa cctgttgtat atcatggcta cacactcacc      660
agcaaacttc tgtttaaaac tgttatccaa gctatacaca agtacgcatt catgacatct      720
gactacccag tggtgctctc tttggaaaat cactgctccc ctgcccagca agaaataatg      780
gcagacaatt tgcagacgac ttttggagag tccttgcttt ctgatatgct tgctgatttt      840
```

```
cctgatactc taccatcacc agaggcacta aaattcaaag tattagttaa aaataagaaa    900
ataggaacct taaaggaaac ccatgaaaga aaaggttctg ataagcgtgg taaggtggag    960
gaatgggaag aagaagtggc agatctggag gaggaggagg aggaggagag attcaaagaa   1020
tcagaaatat tcgaatctgt tttaggagaa aatcaagaca aggaaacagg ggtaaaaaag   1080
ttatctggag taacgctttt caagaaaaag aagaccagga agctaaaaat tgctctggcc   1140
ttatctgatc ttgtcattta tactaaagct gagaagttca aaagctttca acattcaaga   1200
ttatatcagc aatttaatga aaataattct attggggaga cacaagcccg aaaactttca   1260
aaattgagag cccatgagtt tattttcac accaggaagt tcattaccag aatatatccc    1320
aaagcaacaa gagcagactc ttctaatttt aatccccaag aattttggaa ataggttgt    1380
caaatggtgg ctttaaattt ccagacccct ggtctgccta tggatctgca aaatgggaaa   1440
tttttggata tggtggttc tggatatatt ttgaaaccac atttcttaag agagagtgaa   1500
tcatacttta acccaagtga cataaaagac agtatgccaa ttacacttac aataaggctc   1560
atcagtggta tccagttgcc tcttactcat tcatcatcta acaaaggtga tacattagta   1620
attatagaag ttttggtgt tccaaatgat caaatgaagc agcagactcg tgtaattaaa   1680
aaaaatgctt ttagtccaag atggaatgaa acatttacat ttattattca tgtcccagaa   1740
ttggcattga tacgttttgt tgttgaaagt caaggtttaa tagcaggaaa tgaatttctt   1800
gggcaatata ctttgccact tctatgcatg aacaaaggct atcgtcgtgt tcctctgttt   1860
tcccgaatgg gtgagagcct tgagcctgct tcactgtttg tttatgtttg gtacgtcaga   1920
```

<210> SEQ ID NO 7
<211> LENGTH: 641
<212> TYPE: PRT
<213> ORGANISM: Monkey

<400> SEQUENCE: 7

```
Met Glu Met Lys Trp Phe Leu Ser Lys Ile Gln Asp Asp Phe Arg Gly
1               5                   10                  15

Gly Lys Ile Asn Leu Glu Lys Thr Gln Arg Leu Leu Glu Lys Leu Asp
            20                  25                  30

Ile Arg Cys Ser Tyr Ile His Val Lys Arg Ile Phe Lys Asp Asn Asp
        35                  40                  45

Arg Leu Lys Gln Gly Arg Ile Thr Ile Glu Glu Phe Arg Ala Ile Tyr
    50                  55                  60

Arg Ile Leu Thr His Arg Glu Glu Ile Val Glu Ile Phe Asn Ala Tyr
65                  70                  75                  80

Ser Glu Asn Arg Lys Ile Leu Leu Glu Asn Asn Leu Val Gln Phe Leu
                85                  90                  95

Thr Gln Glu Gln Tyr Thr Thr Glu Met Ser Lys Thr Ile Ala Phe Glu
            100                 105                 110

Ile Ile Gln Lys Tyr Glu Pro Ile Glu Glu Val Arg Lys Ala Arg Gln
        115                 120                 125

Met Ser Leu Glu Gly Phe Thr Arg Tyr Met Asp Ser Arg Glu Cys Gln
    130                 135                 140

Leu Phe Lys Asn Glu Cys Arg Lys Val Tyr Gln Asp Met Thr His Pro
145                 150                 155                 160

Leu Asn Asp Tyr Phe Ile Ser Ser His Asn Thr Tyr Leu Val Ser
                165                 170                 175

Asp Gln Leu Val Gly Pro Ser Asp Leu Trp Gly Tyr Val Ser Ala Leu
            180                 185                 190
```

-continued

Val Lys Gly Cys Arg Cys Leu Glu Ile Asp Cys Trp Asp Gly Ala Gln
          195                 200                 205

Asn Glu Pro Val Val Tyr His Gly Tyr Thr Leu Thr Ser Lys Leu Leu
          210                 215                 220

Phe Lys Thr Val Ile Gln Ala Ile His Lys Tyr Ala Phe Met Thr Ser
225                 230                 235                 240

Asp Tyr Pro Val Val Leu Ser Leu Glu Asn His Cys Ser Pro Ala Gln
              245                 250                 255

Gln Glu Ile Met Ala Asp Asn Leu Gln Thr Thr Phe Gly Glu Ser Leu
              260                 265                 270

Leu Ser Asp Met Leu Ala Asp Phe Pro Asp Thr Leu Pro Ser Pro Glu
        275                 280                 285

Ala Leu Lys Phe Lys Val Leu Val Lys Asn Lys Lys Ile Gly Thr Leu
        290                 295                 300

Lys Glu Thr His Glu Arg Lys Gly Ser Asp Lys Arg Gly Lys Val Glu
305                 310                 315                 320

Glu Trp Glu Glu Glu Val Ala Asp Leu Glu Glu Glu Glu Glu Glu Glu
                325                 330                 335

Glu Lys Phe Lys Glu Ser Glu Ile Phe Glu Ser Val Leu Gly Glu Asn
              340                 345                 350

Gln Asp Lys Glu Thr Gly Val Lys Lys Leu Ser Gly Val Thr Leu Phe
          355                 360                 365

Lys Lys Lys Lys Thr Arg Lys Leu Lys Ile Ala Leu Ala Leu Ser Asp
370                 375                 380

Leu Val Ile Tyr Thr Lys Ala Glu Lys Phe Lys Ser Phe Gln His Ser
385                 390                 395                 400

Arg Leu Tyr Gln Gln Phe Asn Glu Asn Asn Ser Ile Gly Glu Thr Gln
              405                 410                 415

Ala Arg Lys Leu Ser Lys Leu Arg Ala His Glu Phe Ile Phe His Thr
          420                 425                 430

Arg Lys Phe Ile Thr Arg Ile Tyr Pro Lys Ala Thr Arg Ala Asp Ser
        435                 440                 445

Ser Asn Phe Asn Pro Gln Glu Phe Trp Asn Ile Gly Cys Gln Met Val
    450                 455                 460

Ala Leu Asn Phe Gln Thr Pro Gly Leu Pro Met Asp Leu Gln Asn Gly
465                 470                 475                 480

Lys Phe Leu Asp Asn Gly Gly Ser Gly Tyr Ile Leu Lys Pro His Phe
              485                 490                 495

Leu Arg Glu Ser Glu Ser Tyr Phe Asn Pro Ser Asp Ile Lys Asp Ser
          500                 505                 510

Met Pro Ile Thr Leu Thr Ile Arg Leu Ile Ser Gly Ile Gln Leu Pro
        515                 520                 525

Leu Thr His Ser Ser Ser Asn Lys Gly Asp Thr Leu Val Ile Ile Glu
        530                 535                 540

Val Phe Gly Val Pro Asn Asp Gln Met Lys Gln Gln Thr Arg Val Ile
545                 550                 555                 560

Lys Lys Asn Ala Phe Ser Pro Arg Trp Asn Glu Thr Phe Thr Phe Ile
              565                 570                 575

Ile His Val Pro Glu Leu Ala Leu Ile Arg Phe Val Val Glu Ser Gln
          580                 585                 590

Gly Leu Ile Ala Gly Asn Glu Phe Leu Gly Gln Tyr Thr Leu Pro Leu
        595                 600                 605

Leu Cys Met Asn Lys Gly Tyr Arg Arg Val Pro Leu Phe Ser Arg Met

```
                    610                615              620
Gly Glu Ser Leu Glu Pro Ala Ser Leu Phe Val Tyr Val Trp Tyr Val
625                 630              635                 640

Arg

<210> SEQ ID NO 8
<211> LENGTH: 1923
<212> TYPE: DNA
<213> ORGANISM: Monkey

<400> SEQUENCE: 8
atggaaatga atggtttttt gtcgaagatt caggatgact ttagaggtgg aaaaattaat       60
ctagaaaaaa ctcagaggtt acttgaaaaa ttagatattc ggtgcagtta tattcatgtg      120
aaacggatat ttaaggacaa tgacaggctg aaacaaggaa gaatcaccat agaagaattt      180
agagcaattt atcgaattct cacgcacaga aagaaattg ttgagatttt caacgcatat       240
tctgaaaacc ggaaaattct tttagaaaat aatctggttc aatttctgac acaagaacaa      300
tatacaactg agatgagtaa aactattgct tttgagatca ttcagaaata tgaacctatc      360
gaagaagtta ggaaagcacg ccaaatgtca ttagaaggtt ttacaagata tatggattca      420
cgtgaatgtc aactatttaa aaatgaatgt agaaaagttt atcaagatat gactcatcca      480
ttaaatgatt attttatttc atcttcacat aacacatatt tggtatctga tcaattagtg      540
ggaccaagtg acctttgggg atatgtaagt gcccttgtga aggatgccg ttgtttggag       600 attgattgct gggatggagc acaaaatgaa cctgttgtat atcatggcta cacactcacc      660
agcaaacttc tgtttaaaac tgttatccaa gctatacaca agtacgcatt catgacatct      720
gactacccag tggtgctctc tttagaaaat cactgctccc ctgcccagca agaaataatg      780
gcagacaatt gcagacgac ttttggagag tccttgcttt ctgatatgct tgctgatttt       840
cctgatactc taccatcacc agaggcacta aaattcaaag tattagttaa aaataagaaa      900
ataggaacct taaggaaac ccatgaaaga aaaggttctg ataagcgtgg taaggtggag       960
gaatgggaag aagaagtggc agatctggag gaggaggagg aggaggagga gaaattcaaa     1020
gaatcagaaa tattcgaatc tgttttagga gaaaatcaag acaaggaaac aggggtaaaa     1080
aagttatctg gagtaacgct tttcaagaaa aagaagacca ggaagctaaa aattgctctg     1140
gccttatctg atcttgtcat ttatactaaa gctgagaagt tcaaaagctt tcaacattca     1200
agattatatc agcaatttaa tgaaaataat tctattgggg agacacaagc ccgaaaactt     1260
tcaaaattga gagcccatga gtttattttt cacaccagga agttcattac agaatatat      1320 cccaaagcaa caagagcaga ctcttctaat tttaatcccc aagaattttg gaatataggt     1380
tgtcaaatgg tggctttaaa tttccagacc cctggtctgc tatggatct gcaaaatggg     1440 aaattttgg ataatggtgg ttctggatat attttgaaac cacatttctt aagagagagt      1500
gaatcatact ttacccaag tgacataaaa gacagtatgc caattacact tacaataagg     1560
ctcatcagtg gtatccagtt gcctcttact cattcatcat ctaacaaagg tgatacatta     1620
gtaattatag aagttttgg tgttccaaat gatcaaatga agcagcagac tcgtgtaatt     1680
aaaaaaaatg cttttagtcc aagatggaat gaaacattta catttattat tcatgtccca     1740
gaattggcat tgatacgttt tgttgttgaa agtcaaggtt taatagcagg aaatgaattt     1800
cttgggcaat atactttgcc acttctatgc atgaacaaag gctatcgtcg tgttcctctg     1860
ttttcccgaa tgggtgagag ccttgagcct gcttcactgt ttgtttatgt ttggtacgtc     1920
aga                                                                   1923
```

<210> SEQ ID NO 9
<211> LENGTH: 640
<212> TYPE: PRT
<213> ORGANISM: Monkey

<400> SEQUENCE: 9

Met Glu Met Lys Trp Phe Leu Ser Lys Ile Gln Asp Asp Phe Arg Gly
1               5                   10                  15

Gly Lys Ile Asn Leu Glu Lys Thr Gln Arg Leu Leu Glu Lys Leu Asp
            20                  25                  30

Ile Arg Cys Ser Tyr Ile His Val Lys Arg Ile Phe Lys Asp Asn Asp
        35                  40                  45

Arg Leu Lys Gln Gly Arg Ile Thr Ile Glu Glu Phe Arg Ala Ile Tyr
    50                  55                  60

Arg Ile Leu Thr His Arg Glu Glu Ile Val Glu Ile Phe Asn Ala Tyr
65                  70                  75                  80

Ser Glu Asn Arg Lys Ile Leu Leu Glu Asn Asn Leu Val Gln Phe Leu
                85                  90                  95

Thr Gln Glu Gln Tyr Thr Thr Glu Met Ser Lys Thr Ile Ala Phe Glu
            100                 105                 110

Ile Ile Gln Lys Tyr Glu Pro Ile Glu Glu Val Arg Lys Ala Arg Gln
        115                 120                 125

Met Ser Leu Glu Gly Phe Thr Arg Tyr Met Asp Ser Arg Glu Cys Gln
    130                 135                 140

Leu Phe Lys Asn Glu Cys Arg Lys Val Tyr Gln Asp Met Thr His Pro
145                 150                 155                 160

Leu Asn Asp Tyr Phe Ile Ser Ser Ser His Asn Thr Tyr Leu Val Ser
                165                 170                 175

Asp Gln Leu Val Gly Pro Ser Asp Leu Trp Gly Tyr Val Ser Ala Leu
            180                 185                 190

Val Lys Gly Cys Arg Cys Leu Glu Ile Asp Cys Trp Asp Gly Ala Gln
        195                 200                 205

Asn Glu Pro Val Val Tyr His Gly Tyr Thr Leu Thr Ser Lys Leu Leu
    210                 215                 220

Phe Lys Thr Val Ile Gln Ala Ile His Lys Tyr Ala Phe Met Thr Ser
225                 230                 235                 240

Asp Tyr Pro Val Val Leu Ser Leu Glu Asn His Cys Ser Pro Ala Gln
                245                 250                 255

Gln Glu Ile Met Ala Asp Asn Leu Gln Thr Thr Phe Gly Glu Ser Leu
            260                 265                 270

Leu Ser Asp Met Leu Ala Asp Phe Pro Asp Thr Leu Pro Ser Pro Glu
    275                 280                 285

Ala Leu Lys Phe Lys Val Leu Val Lys Asn Lys Lys Ile Gly Thr Leu
290                 295                 300

Lys Glu Thr His Glu Arg Lys Gly Ser Asp Lys Arg Gly Lys Val Glu
305                 310                 315                 320

Glu Trp Glu Glu Glu Val Ala Asp Leu Glu Glu Glu Glu Glu Glu Glu
                325                 330                 335

Arg Phe Lys Glu Ser Glu Ile Phe Glu Ser Val Leu Gly Glu Asn Gln
            340                 345                 350

Asp Lys Glu Thr Gly Val Lys Lys Leu Ser Gly Val Thr Leu Phe Lys
    355                 360                 365

Lys Lys Lys Thr Arg Lys Leu Lys Ile Ala Leu Ala Leu Ser Asp Leu
370                 375                 380

Val Ile Tyr Thr Lys Ala Glu Lys Phe Lys Ser Phe Gln His Ser Arg
385                 390                 395                 400

Leu Tyr Gln Gln Phe Asn Glu Asn Asn Ser Ile Gly Glu Thr Gln Ala
            405                 410                 415

Arg Lys Leu Ser Lys Leu Arg Ala His Glu Phe Ile Phe His Thr Arg
        420                 425                 430

Lys Phe Ile Thr Arg Ile Tyr Pro Lys Ala Thr Arg Ala Asp Ser Ser
    435                 440                 445

Asn Phe Asn Pro Gln Glu Phe Trp Asn Ile Gly Cys Gln Met Val Ala
450                 455                 460

Leu Asn Phe Gln Thr Pro Gly Leu Pro Met Asp Leu Gln Asn Gly Lys
465                 470                 475                 480

Phe Leu Asp Asn Gly Gly Ser Gly Tyr Ile Leu Lys Pro His Phe Leu
                485                 490                 495

Arg Glu Ser Glu Ser Tyr Phe Asn Pro Ser Asp Ile Lys Asp Ser Met
            500                 505                 510

Pro Ile Thr Leu Thr Ile Arg Leu Ile Ser Gly Ile Gln Leu Pro Leu
        515                 520                 525

Thr His Ser Ser Ser Asn Lys Gly Asp Thr Leu Val Ile Ile Glu Val
    530                 535                 540

Phe Gly Val Pro Asn Asp Gln Met Lys Gln Gln Thr Arg Val Ile Lys
545                 550                 555                 560

Lys Asn Ala Phe Ser Pro Arg Trp Asn Glu Thr Phe Thr Phe Ile Ile
                565                 570                 575

His Val Pro Glu Leu Ala Leu Ile Arg Phe Val Val Glu Ser Gln Gly
            580                 585                 590

Leu Ile Ala Gly Asn Glu Phe Leu Gly Gln Tyr Thr Leu Pro Leu Leu
        595                 600                 605

Cys Met Asn Lys Gly Tyr Arg Arg Val Pro Leu Phe Ser Arg Met Gly
    610                 615                 620

Glu Ser Leu Glu Pro Ala Ser Leu Phe Val Tyr Val Trp Tyr Val Arg
625                 630                 635                 640

<210> SEQ ID NO 10
<211> LENGTH: 1938
<212> TYPE: DNA
<213> ORGANISM: Rat

<400> SEQUENCE: 10
atgcatgctc gagcggccgc cagtgtgatg gatatctgca gaattcgccc ttttcaggat      60
gatttcagag gtggaaaaat cagcgctgga attactcaca aactgctcga gaaacttgat     120
ttcccatgcc attttgctca gtgaaacgt attttaagg aaaatgacag acataaccaa       180
ggaagaatca ccaccgaaga ttttagaacc atctatcggt gtattgtaca tagagaagag     240
atcgttgaga ttttcaacac gtatactgaa acaggaaaaa ttctccccga ggacagtctg     300
attgaatttc taacccaaga gcagtatgaa atggagatgg atgagtccag ttcagtggag     360
atcatccaga agtacgagcc cattgcagaa gtaaagaacg agcggcagat gtcaattgaa     420
ggttttgcaa gatacatgtt ttcttcagaa tgtctactgt ttaaagagac gtgtaacaca     480
gtgtaccaag atatgaataa gccactaaat gattactata tttcatcgtc tcacaacaca     540
tatttgatat ctgatcaaat attgggacca agtgacattt ggggatatat aagtgccctc     600
gtgaaaggtt gccgctgtct ggaaattgac tgctgggatg agcacaaaaa tgaacccatt     660
gtgtaccatg gctacactct caccagcaag cttctcttca aaaccgttat ccaagcaata     720

```
aacaagtacg ccttcgtgac gtctgattac ccagtggtgc tgtccttaga gaatcactgc    780 tccccctggtc aacaggaagt gatgaccgac attctgcaga gtacctttgg agactttctg   840
ctctcagaca tacttgacga gtttccagac agtttgccat ctccagaggc actgaaattt    900
aaaatattag tgaaaaataa gaaagttgga accttatctg aaacccgcga gaggctgggg    960
actgacaaaa ggggcatagc gctagacttg gaagaagaaa tctatgaaaa tgaagacgaa   1020
gactcaggaa aggagccaga aacgtgggat gatttcctgt cacgggttaa ggaggagcag   1080
gaggcagacc cctcaacgtt gagcggaata gcagatgcca agaaaaagat caggaagcta   1140
agagtagctc tggccttatc tgatcttgtc atttatacca aagctgagaa gttccgaaac   1200
ttccaatatt caagagtcta tcagcagttt aatgagacca cttctatggg agagtctcga   1260
gctcgaaaac tttcaaaatt gagagcccat gagtttattt tccacactgc agcgttcatc   1320
accagagtgt accccaagtt cacgagagca gactcttcta attttaatcc tcaagagttt   1380
tggaatgtgg gctgtcagat ggtggccttg aatttttcaaa cccctggact gcctatggat   1440
ttgcaaaacg ggaaattttt ggataatgga ggctctggat atgttttgaa ccagactttt   1500
cttagagaca caactttggg ctttaaccca atgaaccag aaggagatgg ccatccggtt   1560
accctcacga tccgactcat cagtgggatc cagttgcctg ttaacgtgcc ctcaaataca    1620
tctgacataa tagtgatcat agaagtctac ggtgtcccaa acgaccacat gaagcagcag    1680
agtcgtgccg ttaagaacaa tgcttttagt ccaaggtgga atgaaacatt cacatttctt    1740
attcaagtgc cagaattggc actgatacgt ttcgttgttg aaactcaagg cttcctatcg    1800
ggaaatgaat tacttgggca gtacacttta cccgttcttt gcatgaacaa aggttatcgt    1860
cgtgttcctc tgttttccaa atccggtgcg aaccttgaac cttcctctct gtttatttac    1920
gtttggtact acagagag                                                   1938
```

<210> SEQ ID NO 11
<211> LENGTH: 646
<212> TYPE: PRT
<213> ORGANISM: Rat

<400> SEQUENCE: 11

```
Met His Ala Arg Ala Ala Ser Val Met Asp Ile Cys Arg Ile Arg
1               5                   10                  15

Pro Phe Gln Asp Asp Phe Arg Gly Gly Lys Ile Ser Ala Gly Ile Thr
                20                  25                  30

His Lys Leu Leu Glu Lys Leu Asp Phe Pro Cys His Phe Ala His Val
            35                  40                  45

Lys Arg Ile Phe Lys Glu Asn Asp Arg His Asn Gln Gly Arg Ile Thr
        50                  55                  60

Thr Glu Asp Phe Arg Thr Ile Tyr Arg Cys Ile Val His Arg Glu Glu
65                  70                  75                  80

Ile Val Glu Ile Phe Asn Thr Tyr Thr Glu Asn Arg Lys Ile Leu Pro
                85                  90                  95

Glu Asp Ser Leu Ile Glu Phe Leu Thr Gln Gln Tyr Glu Met Glu
                100                 105                 110

Met Asp Glu Ser Ser Ser Val Glu Ile Ile Gln Lys Tyr Glu Pro Ile
            115                 120                 125

Ala Glu Val Lys Asn Glu Arg Gln Met Ser Ile Glu Gly Phe Ala Arg
        130                 135                 140

Tyr Met Phe Ser Ser Glu Cys Leu Leu Phe Lys Glu Thr Cys Asn Thr
145                 150                 155                 160
```

```
Val Tyr Gln Asp Met Asn Lys Pro Leu Asn Asp Tyr Tyr Ile Ser Ser
                165                 170                 175

Ser His Asn Thr Tyr Leu Ile Ser Asp Gln Ile Leu Gly Pro Ser Asp
            180                 185                 190

Ile Trp Gly Tyr Ile Ser Ala Leu Val Lys Gly Cys Arg Cys Leu Glu
        195                 200                 205

Ile Asp Cys Trp Asp Gly Ala Gln Asn Glu Pro Ile Val Tyr His Gly
    210                 215                 220

Tyr Thr Leu Thr Ser Lys Leu Leu Phe Lys Thr Val Ile Gln Ala Ile
225                 230                 235                 240

Asn Lys Tyr Ala Phe Val Thr Ser Asp Tyr Pro Val Val Leu Ser Leu
                245                 250                 255

Glu Asn His Cys Ser Pro Gly Gln Gln Glu Val Met Thr Asp Ile Leu
            260                 265                 270

Gln Ser Thr Phe Gly Asp Phe Leu Leu Ser Asp Ile Leu Asp Glu Phe
        275                 280                 285

Pro Asp Ser Leu Pro Ser Pro Glu Ala Leu Lys Phe Lys Ile Leu Val
    290                 295                 300

Lys Asn Lys Lys Val Gly Thr Leu Ser Glu Thr Arg Glu Arg Leu Gly
305                 310                 315                 320

Thr Asp Lys Arg Gly Ile Ala Leu Asp Leu Glu Glu Ile Tyr Glu
                325                 330                 335

Asn Glu Asp Glu Asp Ser Gly Lys Glu Pro Glu Thr Trp Asp Phe
            340                 345                 350

Leu Ser Arg Val Lys Glu Gln Glu Ala Asp Pro Ser Thr Leu Ser
        355                 360                 365

Gly Ile Ala Asp Ala Lys Lys Lys Ile Arg Lys Leu Arg Val Ala Leu
    370                 375                 380

Ala Leu Ser Asp Leu Val Ile Tyr Thr Lys Ala Glu Lys Phe Arg Asn
385                 390                 395                 400

Phe Gln Tyr Ser Arg Val Tyr Gln Gln Phe Asn Glu Thr Thr Ser Met
                405                 410                 415

Gly Glu Ser Arg Ala Arg Lys Leu Ser Lys Leu Arg Ala His Glu Phe
            420                 425                 430

Ile Phe His Thr Ala Ala Phe Ile Thr Arg Val Tyr Pro Lys Phe Thr
        435                 440                 445

Arg Ala Asp Ser Ser Asn Phe Asn Pro Gln Glu Phe Trp Asn Val Gly
450                 455                 460

Cys Gln Met Val Ala Leu Asn Phe Gln Thr Pro Gly Leu Pro Met Asp
465                 470                 475                 480

Leu Gln Asn Gly Lys Phe Leu Asp Asn Gly Ser Gly Tyr Val Leu
                485                 490                 495

Lys Pro Asp Phe Leu Arg Asp Thr Thr Leu Gly Phe Asn Pro Asn Glu
            500                 505                 510

Pro Glu Gly Asp Gly His Pro Val Thr Leu Thr Ile Arg Leu Ile Ser
        515                 520                 525

Gly Ile Gln Leu Pro Val Asn Val Pro Ser Asn Thr Ser Asp Ile Ile
    530                 535                 540

Val Ile Ile Glu Val Tyr Gly Val Pro Asn Asp His Met Lys Gln Gln
545                 550                 555                 560

Ser Arg Ala Val Lys Asn Asn Ala Phe Ser Pro Arg Trp Asn Glu Thr
                565                 570                 575

Phe Thr Phe Leu Ile Gln Val Pro Glu Leu Ala Leu Ile Arg Phe Val
```

```
                580             585             590
Val Glu Thr Gln Gly Phe Leu Ser Gly Asn Glu Leu Leu Gly Gln Tyr
        595                 600                 605

Thr Leu Pro Val Leu Cys Met Asn Lys Gly Tyr Arg Arg Val Pro Leu
    610                 615                 620

Phe Ser Lys Ser Gly Ala Asn Leu Glu Pro Ser Ser Leu Phe Ile Tyr
625                 630                 635                 640

Val Trp Tyr Tyr Arg Glu
            645

<210> SEQ ID NO 12
<211> LENGTH: 27
<212> TYPE: DNA
<213> ORGANISM: artificial sequence
<220> FEATURE:
<223> OTHER INFORMATION: Forward human primer

<400> SEQUENCE: 12
cagcgagctc ttatctgacg taccaaa                                     27

<210> SEQ ID NO 13
<211> LENGTH: 26
<212> TYPE: DNA
<213> ORGANISM: artificial sequence
<220> FEATURE:
<223> OTHER INFORMATION: Reverse Trip1Ex primer

<400> SEQUENCE: 13
ctcgggaagc gcgccattgt gttggt                                      26

<210> SEQ ID NO 14
<211> LENGTH: 28
<212> TYPE: DNA
<213> ORGANISM: artificial sequence
<220> FEATURE:
<223> OTHER INFORMATION: Forward mouse primer

<400> SEQUENCE: 14
gctaacgcgt cagttacatg cgtcactc                                    28

<210> SEQ ID NO 15
<211> LENGTH: 22
<212> TYPE: DNA
<213> ORGANISM: artificial sequence
<220> FEATURE:
<223> OTHER INFORMATION: Reverse T7 primer

<400> SEQUENCE: 15
gtaatacgac tcactatagg gc                                          22

<210> SEQ ID NO 16
<211> LENGTH: 28
<212> TYPE: DNA
<213> ORGANISM: artificial sequence
<220> FEATURE:
<223> OTHER INFORMATION: Forward human primer

<400> SEQUENCE: 16
cagcgagctc ttatctgacg taccaaac                                    28

<210> SEQ ID NO 17
<211> LENGTH: 24
<212> TYPE: DNA
<213> ORGANISM: artificial sequence
<220> FEATURE:
```

```
<223> OTHER INFORMATION: Reverse human primer

<400> SEQUENCE: 17
atgaaactat ggaaatgaga tggt                                          24

<210> SEQ ID NO 18
<211> LENGTH: 28
<212> TYPE: DNA
<213> ORGANISM: artificial sequence
<220> FEATURE:
<223> OTHER INFORMATION: Forward mouse primer

<400> SEQUENCE: 18
gctaacgcgt cagttacatg cgtcactc                                      28

<210> SEQ ID NO 19
<211> LENGTH: 19
<212> TYPE: DNA
<213> ORGANISM: artificial sequence
<220> FEATURE:
<223> OTHER INFORMATION: Reverse mouse primer

<400> SEQUENCE: 19
atcatggaaa gccaacttc                                                19

<210> SEQ ID NO 20
<211> LENGTH: 9
<212> TYPE: PRT
<213> ORGANISM: Monkey

<400> SEQUENCE: 20

Gln Asp Asp Phe Arg Gly Gly Lys Ile
1               5

<210> SEQ ID NO 21
<211> LENGTH: 6
<212> TYPE: PRT
<213> ORGANISM: Monkey

<400> SEQUENCE: 21

Leu Leu Glu Lys Leu Asp
1               5

<210> SEQ ID NO 22
<211> LENGTH: 5
<212> TYPE: PRT
<213> ORGANISM: Monkey

<400> SEQUENCE: 22

Gln Gly Arg Ile Thr
1               5

<210> SEQ ID NO 23
<211> LENGTH: 6
<212> TYPE: PRT
<213> ORGANISM: Monkey

<400> SEQUENCE: 23

Glu Asn Arg Lys Ile Leu
1               5

<210> SEQ ID NO 24
<211> LENGTH: 7
<212> TYPE: PRT
<213> ORGANISM: Monkey
```

```
<400> SEQUENCE: 24

Phe Leu Thr Gln Glu Gln Tyr
1               5

<210> SEQ ID NO 25
<211> LENGTH: 6
<212> TYPE: PRT
<213> ORGANISM: Monkey

<400> SEQUENCE: 25

Tyr Gln Gln Phe Asn Glu
1               5

<210> SEQ ID NO 26
<211> LENGTH: 5
<212> TYPE: PRT
<213> ORGANISM: Monkey

<400> SEQUENCE: 26

Thr Leu Thr Ile Arg
1               5

<210> SEQ ID NO 27
<211> LENGTH: 7
<212> TYPE: PRT
<213> ORGANISM: Monkey

<400> SEQUENCE: 27

Ile Ser Gly Ile Gln Leu Pro
1               5

<210> SEQ ID NO 28
<211> LENGTH: 9
<212> TYPE: PRT
<213> ORGANISM: Monkey

<400> SEQUENCE: 28

Leu Cys Met Asn Lys Gly Tyr Arg Arg
1               5
```

SPERM FACTOR SEQUENCES

This application is a continuation-in-part of U.S. patent application Ser. No. 10/493,927, filed on Apr. 23, 2004, which in turn claims the benefit of priority in PCT Patent Application No. PCT/GB02/04739 filed on Oct. 18, 2002, British Patent Application No. 0125498.6 filed on Oct. 24, 2001, and British Patent Application No. 0214945.8 filed on Jun. 28, 2002. The disclosures of each of the above-listed references are incorporated herein in their entirety by reference.

TECHNICAL FIELD

This invention relates to the regulation and control of intracellular free calcium ion concentrations and more particularly to the control of cytoplasmic calcium oscillations (CCOs) in mammalian oocytes (eggs). In particular, it relates to phospho-inositide-specific phospholipase C proteins that trigger CCOs that are indistinguishable from those occurring at oocyte fertilization and nucleic acid sequences encoding such proteins, and the use thereof in biotechnology, diagnosis or medicine.

BACKGROUND OF THE INVENTION

Transient changes in the intracellular calcium ($Ca^{2+}$) concentration are known to be responsible for activating numerous physiological processes, including memory formation, muscle contraction, hormone secretion, fertilization, gene transcription and apoptosis. One striking phenomenon observed in numerous cell types, including cardiac myocytes, endothelial cells and eggs, is the generation of a series of regular calcium transients or oscillations in response to cellular stimuli. The best-studied example of this phenomenon is during mammalian fertilization, where calcium levels in the egg begin to oscillate in a regular fashion following fusion with the sperm.

These calcium oscillations occurring at fertilisation, sometimes referred to as the "calcium waves", are believed to be the trigger for egg activation and consequent embryo development. Studies carried out over many years have attempted to discover and isolate the causative agent of this phenomenon with a view to using it for research and for a variety of practical applications, including diagnosis.

This striking $Ca^{2+}$ signalling phenomenon in fertilized mammalian eggs arises from increases in inositol 1,4,5-tris-phosphate ($IP_3$) levels, which activates $IP_3$ receptor-mediated $Ca^{2+}$ release from intracellular stores in the egg. However, the basic mechanism involved in stimulation of phospho-inositide metabolism following sperm-egg interaction has not been determined in any species.

The 'sperm factor hypothesis' of signalling at fertilization proposes that spermatozoa contain a soluble $Ca^{2+}$-releasing factor that enters the egg after the gamete membranes fuse together and generates $Ca^{2+}$ oscillations. This is consistent with the finding that cytoplasmic fusion of sperm and egg is a prelude to $Ca^{2+}$ release. Direct support for this hypothesis comes from experiments where micro-injection into eggs of either single spermatozoa or soluble sperm extracts triggers $Ca^{2+}$ oscillations similar to those at fertilization in mammalian—and some non-mammalian—eggs. The mammalian sperm factor that generates $Ca^{2+}$ oscillations is protein-based; acts across species; and can cause $Ca^{2+}$ release in somatic cells as well as in cell-free systems, such as sea urchin egg homogenates. Sperm specifically express a $Ca^{2+}$ oscillation-inducing protein, because micro-injecting messenger RNA (mRNA) isolated from spermatogenic cells, but not mRNA from other tissues, elicits fertilization-like $Ca^{2+}$ oscillations in mouse eggs.

In intact eggs and egg homogenates, mammalian sperm extracts trigger $Ca^{2+}$ release via stimulating $IP_3$ production, indicating involvement of a phospho-inositide-specific phospholipase C (i.e. PI-PLC, usually referred to in short as PLC) in the signal transduction mechanism. The high level of PLC enzyme activity measured biochemically in sperm extracts has led some researchers to suggest that the sperm factor may itself be a PLC. However, the PLC-beta, gamma and delta (β, γ and δ) isoforms that exist in sperm are not detected in the chromatographic fractions of sperm extract that specifically cause $Ca^{2+}$ oscillations. Also, when purified, recombinant PLCβ2, γ1 or δ1 proteins are added to egg homogenates, they fail to cause $Ca^{2+}$ release. A PLCδ4 splice variant expressed in sperm has been shown to be involved in the acrosome reaction, rather than $Ca^{2+}$ release in eggs at fertilization. Previous research in this field has been described in international patent specification no. WO 96/25495, to which reference should be made for a full understanding of, and as background to, the present application. The contents of WO 96/25495 are therefore incorporated herein by reference.

Patent specification no. WO 96/25945 assigned the cause of the above-mentioned calcium oscillations to a substance (a sperm factor) present in the equatorial segment of sperm, which was believed to diffuse into the egg after fusion therewith. This substance was identified as a 33 kD (approx.) protein of specified amino acid sequence. The nucleic acid coding for this protein was also specified. However, after cloning the gene and undertaking subsequent expression studies, it was concluded that this sperm factor candidate was unable to reconstitute calcium oscillations. A truncated form of the c-kit receptor, has also previously been a sperm factor candidate. However, neither these two, nor any other sperm proteins, have been shown to generate $Ca^{2+}$ oscillations in eggs, the single-most distinctive feature of mammalian fertilization.

These observations have led some workers in the field to conclude, "sperm-derived PLC is not responsible for initiating $Ca^{2+}$ release at fertilization" (Mehlmann et al in Dev Biol 236 492-501 (2001)), whilst others have stated: "the identification of this protein remains a problem for the next century of fertilization research" (Runft et al in Dev Biol 245 237-54 (2002)).

SUMMARY OF THE INVENTION

On the contrary, these observations led us to investigate the possible existence of a distinct, uncharacterised sperm PLC isoform. The present invention relates to the presence of a new PLC isoform specifically expressed in mammalian sperm (hereinafter called PLC-zeta; PLCζ), which uniquely possesses all the essential properties of the sperm factor. The results of our studies are consistent with sperm PLCζ being the physiological trigger of egg activation, and thus an essential protein for mammalian fertilization and embryo development.

The amino acid sequences of both the human and mouse proteins are given hereinafter as SEQ ID NOS: 1 and 2, respectively, and their nucleic acid coding sequences as SEQ ID NOS: 3 and 4, respectively. Also given is the rat protein as SEQ ID NO: 11, and its nucleic acid coding sequence SEQ ID NO: 10.

Recently, the Genbank database disclosed various nucleic acid sequences of human and mouse testes, without attributing any function thereto and predicting an open reading frame (ORF; protein or polypeptide sequence) having a start position corresponding to a position being at least 100 amino acids from the start position of the SEQ ID NOS: 3 and 4. In particular, Genbank Accession No AK006672 (deposited 5 Jul. 2001) comprises 2227 base pairs of mouse testis sequence but predicts an ORF encoding 537 amino acids with a start position corresponding to position aa 111 (MEIDH) of the mouse sequence [SEQ ID NO: 4] (i.e. missing the first 110aa (amino acids));

Genbank Accession No XM029802 (deposited 16 Oct. 2001) comprises 2113 base pairs of human testis sequence, not identical to and predictive of an ORF encoding 504 amino acids with a start position corresponding to position aa 105 (MSKAI) of the human sequence [SEQ ID NO: 3] (i.e. missing the first 104aa);

Genbank Accession No NM033123 (deposited 21 Aug. 2001) comprises 2132 base pairs of human testis sequence in database, but predicts an ORF encoding 504 amino acids with a start position corresponding to position aa 105 (MSKAI) of the human sequence [SEQ ID NO: 3] (i.e. missing the first 104aa); and Genbank Accession No AY035866 (deposited 22 Jun. 2001) comprises 2132 base pairs of human testis sequence in database, but predicts an ORF encoding 504 amino acids with a start position corresponding to position aa 105 (MSKAI) of the human sequence [SEQ ID NO: 3] (i.e. missing the first 104aa).

Genbank Accession No. AB070108 (deposited 16 Aug. 2001) comprises 2219 base pairs of monkey testis sequence with an ORF of 1923 base pairs (nucleotides 220-2142) encoding 641 amino acids, without attributing any function thereto or connection with a putative sperm factor. [SEQ ID NOs: 6 and 7, respectively].

Similarly, Genbank Accession No. AB0070109 (deposited 16 Aug. 2001) comprises 2218 base pairs of monkey testis sequence with an ORF of 1920 base pairs (nucleotides 220-2139) encoding 640 amino acids, without attributing any function thereto or connection with a putative sperm factor. [SEQ ID NOs: 8 and 9, respectively].

The differences in the protein sequence between AB070108 and AB070109 are shown below:

| AB070108 (aa334-343): | E E E K F K E S E |
| AB070109 (aa334-342): | E E E - R F K E S E |

Accordingly, the present invention provides a PLC-zeta protein, characterised by exhibiting one or more of the following properties:
(a) An amino acid sequence comprising in the range of from 600 to 720, preferably 600 to 699, more preferably 600 to 650, amino acid residues;
(b) A domain sequence comprising the EF hand, X, Y, and C2 domains but absent the PH domain; and
(c) At, least five consecutive amino acid residues from a conserved region, which region is selected from:

| (i) | QDDFRGGKI | (SEQ ID NO: 20; 11-19); |
| (ii) | LLEKLD | (SEQ ID NO: 21; 27-32); and |
| (iii) | QGRIT | (SEQ ID NO: 22; 52-56) in the EF1 domain; |
| (iv) | ENRKIL | (SEQ ID NO: 23; 82-87); and |
| (v) | FLTQEQY | (SEQ ID NO: 24; 95-101) in the EF2 domain; |
| (vi) | YQQFNE | (SEQ ID NO: 25; 403-408) in the Y domain; and |
| (vii) | TLTIR | (SEQ ID NO: 26; 516-520); |
| (viii) | ISGIQLP | (SEQ ID NO: 27; 522-528); and |
| (ix) | LCMNKGYRR | (SEQ ID NO: 28; 609-617) in the C2 domain, | wherein the residues are denoted by their conventional single letter codes and the numbers in parentheses refer to the sequence co-ordinates within the 641 amino acid ORF of the monkey AB070108 (monkey A) sequence.

Below is a table (Table 1) showing a comparison between lengths of various PLCs (criterion (a)); FIG. 3 shows the domain comparison between the various PLCs (criterion (b)); and [SEQ ID NO: 12] illustrates the conserved regions of PLC-zeta cross-species, compared to other PLCs (criterion (c)). Comparison between the PLC sequence types was made using the Clustal W analysis program using the default settings.

TABLE 1

PLCs - Sequence Lengths

| PLC Types | Species | No. of amino acid residues |
|---|---|---|
| zeta | human | 608 |
| zeta | monkeyA | 641 |
| zeta | mouse | 647 |
| zeta | rat | 646 |
| beta 1 | human | 1211 |
| beta 2 | human | 1181 |
| beta 3 | mouse | 1234 |
| beta 4 | mouse | 1175 |
| gamma 1 | human | 1290 |
| gamma 2 | human | 1252 |
| delta 1 | human | 756 |
| delta 2 | bovine | 764 |
| delta 3 | human | 736 |
| delta 4 | rat | 772 |
| epsilon | human | 2302 |
| 1 | potato | 596 |
| 2 | potato | 565 |
| 3 | potato | 585 |

Accordingly, the present invention provides an isolated, purified or recombinant nucleic acid molecule comprising a nucleic acid molecule encoding a PLC-zeta, PLCζ, polypeptide, capable of triggering calcium oscillations in oocytes.

The nucleic acid molecule of the invention is identified by virtue of the sequences disclosed herein and further includes sequences substantially homologous thereto or sequences that hybridize thereto under stringent conditions. In discussing stringency conditions for hybridization of nucleic acid sequences as set forth in the present disclosure, it is understood that the terms "hybridize under stringent conditions" or "hybridizes under stringent conditions" means hybridization conditions regarded as stringent, as set forth in "Molecular Cloning: A Laboratory Manual (Third Edition), 2001, Joseph Sambrook and David Russell, Cold Spring Harbor Laboratory Press, the disclosure of which is incorporated by reference in its entirety as if fully set forth herein.

In particular, as used herein "hybridize under stringent conditions" or "hybridizes under stringent conditions" describes conditions known in the art for hybridization and washing. A number of methods are set forth in the referenced Sambrook and Russell publication satisfying hybridization under stringent conditions, and use of any is contemplated. In one preferred process using aqueous solvents, stringent hybridization is conducted in 6x sodium chloride/sodium citrate (SSC) or 6× saline-sodium phosphate-EDTA (SSPE) with 5×Denhardt's reagent, 0.5% w/v SDS, 1 µg poly(A), and 100 µg/ml salmon sperm DNA at 68° C. followed by one or more washes with 2×SSC and 0.1% SDS at room temperature and one or more washes with 0.1×SSC with 0.1% SDS at 65° C., and a final wash with 0.1×SSC at room temperature.

Another contemplated procedure for hybridization under stringent conditions using solvents containing 50% formamide conducts hybridization in 6× sodium chloride/sodium citrate (SSC) or 6× saline-sodium phosphate-EDTA (SSPE) with 5×Denhardt's reagent, 0.5% w/v SDS, 1 µg poly(A), 100 µg/ml salmon sperm DNA, and 50% v/v formamide at 42° C., followed by the washing steps set forth above.

Yet another contemplated procedure for hybridization under stringent conditions using phosphate-SDS solvents conducts hybridization in 0.5 M sodium phosphate pH 7.2, 0.1×1 mM EDTA pH 8.0, 7% w/v SDS, and 1% w/v bovine serum albumin at 65° C., followed by eight washes in Phosphate-SDS washing solution (40 mM sodium phosphate buffer pH 7.2, 1 mM EDTA pH 8.0, 1% w/v SDS) at 65° C.

Still yet another contemplated procedure for hybridization in roller bottles under stringent conditions using phosphate-SDS solvents conducts hybridization in 6× sodium chloride/sodium citrate (SSC) or 6× saline-sodium phosphate-EDTA (SSPE) at 65° C., followed by two washes in Phosphate-SDS washing solution (40 mM sodium phosphate buffer pH 7.2, 1 mM EDTA pH 8.0, 5% w/v SDS, and 0.5% w/v Fraction-V-grade bovine serum albumin) at 65° C., followed by eight washes in Phosphate-SDS washing solution (40 mM sodium phosphate buffer pH 7.2, 1 mM EDTA pH 8.0, 1% w/v SDS) at 65° C.

In a further aspect of the invention there is provided at least one oligonucleotide specific for a part of the aforementioned sequences. Preferably, said oligonucleotide includes the primers described herein and more specifically the following:

```
Forward human primer:
5' CAG CGA GCT CTT ATC TGA CGT ACC AAA C 3'
(SEQ ID NO: 12; 28mer).

Reverse TriplEx primer:
5' CTC GGG AAG CGC GCC ATT GTG TTG GT 3'
(SEQ ID NO: 13; 26mer).

Forward mouse primer:
5' GCT AAC GCG TCA GTT ACA TGC GTC ACT C 3'
(SEQ ID NO: 14; 28mer)

Reverse T7 primer:
5' GTA ATA CGA CTC ACT ATA GGG C 3'
(SEQ ID NO: 15; 22mer)

Forward human primer:
5' CAG CGA GCT CTT ATC TGA CGT ACC AAA C 3'
(SEQ ID NO: 16; 28mer)

Reverse human primer:
5' ATG AAA CTA TGG AAA TGA GAT GGT 3'
(SEQ ID NO: 17; 24mer)

Forward mouse primer:
5' GCT AAC GCG TCA GTT ACA TGC GTC ACT C 3'
(SEQ ID NO: 18; 28mer)

Reverse mouse primer:
5' ATC ATG GAA AGC CAA CTT C 3' (SEQ ID NO: 19;
19mer)
```

By "substantially homologous" herein is meant that the nucleic acid sequence has at least 70% identity of its nucleotide bases with those of sequence (a), in matching positions in the sequence. A further 10% of its nucleotide bases may comprise conservative substitutions (with similar bases), and therefore the sequence has at least 80% overall homology. More preferred are sequences having at least 80% identity with the sequence (a) and about 90% overall homology. Such homologous sequences encode a protein having substantially the same biological activity as the proteins of the invention.

Oligonucleotides "specific for" any of these nucleic acid sequences (a) to (c) above are useful for identifying and isolating the biologically active peptides of this invention, and comprise a unique sequence encoding a unique fragment of the amino acid sequence of the peptide.

In particular, the present invention provides a nucleic acid sequence as defined above, wherein the sequence is a DNA or RNA sequence, such as cDNA, cRNA or mRNA. More particularly, the present invention provides:

a DNA sequence identified herein by [SEQ ID NO: 3], which sequence (being the human PLC-zeta; PLCζ nucleotide sequence, 1827 nucleotides) corresponds with the polypeptide identified herein as [SEQ ID NO: 1];

a DNA sequence identified herein by [SEQ ID NO: 4], which sequence (being the mouse PLC-zeta; PLCζ nucleotide sequence, 1944 nucleotides) corresponds with the polypeptide identified herein as [SEQ ID NO: 2]; and a DNA sequence identified herein by [SEQ ID NO: 10], which sequence (being the rat PLC-zeta; PLCζ nucleotide sequence, 1938 nucleotides) corresponds with the polypeptide identified herein as [SEQ ID NO: 11].

The mouse sequence has been deposited under Genbank Accession No AF 435950, which comprises 1941 nucleotides of the protein-coding region plus the stop codon (3 nucleotides) (these, together, consist of the [SEQ ID NO: 4]) plus the untranslated region (totaling 2-187 nucleotides) identified herein as [SEQ ID NO: 5].

Therefore, the present invention further provides a polypeptide of:

[SEQ ID NO: 1], being the human PLC-zeta; PLCζ amino acid sequence, 608 residues;

[SEQ ID NO: 2], being the mouse PLC-zeta; PLCζ amino acid sequence, total 647 residues; and

[SEQ ID NO: 11], being the rat PLC-zeta; PLCζ amino acid sequence, total 646 residues, in which amino acids are represented by their conventional single letter codes.

Furthermore, the invention provides for the use of certain known sequences to which a function has not previously been assigned as a PLC-zeta, PLCζ or sperm factor. In particular, the invention provides for such use of the monkey proteins [SEQ ID NOs: 7 and 9].

The deduced human and mouse proteins of SEQ ID NOS: 1 and 2 differ by 39 amino acids in length and their cDNA sequences differ correspondingly. It will be appreciated that similarly active proteins and corresponding nucleic acid sequences encoding them will be present in the sperm of other mammalian species, including species of farm animals e.g. sheep and pigs, and other animal species e.g. fish. All such proteins and nucleic acid sequences have a high degree of sequence homology with one another, and can be readily isolated using the newly discovered DNA sequences or parts thereof to probe the appropriate cDNA libraries of other species. It is expected that the molecular weight of the proteins will be in the range of from 65 to 80 kD, preferably in the range of from 70 to 75 kD, especially about 70 kD, as determined by mass spectrometry.

Derivatives of the proteins disclosed herein (i.e. of [SEQ ID NOS: 1, 2 and 11], and homologous sequences) having substantially similar biological activity are also encompassed. For example, one or more of which derivatives may comprise post-translational modifications, such as glycosylation at asparagine, serine or threonine; and/or sulphato- or phospho-groups on tyrosine, such as are commonly found in polypeptides; polymorphisms, such as single nucleotide polymorphisms (SNPs); and those further comprising a leader/signal sequence.

The invention further provides a tagged derivative of a PLC-zeta, such as a tagged derivative of any polypeptide sequence specifically identified herein, including [SEQ ID NOs: 1, 2, 7, 9 and 11], for use in identifying the PLC-zeta in diagnostic tests, other assays or otherwise as a research or clinical tool. Suitably, the PLC-zeta is tagged with c-Myc as described in Example 6 hereinbelow, antibodies to which are commercially available (e.g. from Santa Cruz Biotechnology).

A polypeptide encompassed by this invention can also be prepared by providing or culturing a host, transformed with an expression vector comprising a DNA sequence encoding the polypeptide under such conditions that the polypeptide is expressed therein, and optionally isolating the polypeptide thus obtained. This approach is typically based on obtaining a nucleotide sequence encoding the polypeptide it is wished to express, and expressing the polypeptide in a recombinant organism. The cultivation of the genetically modified organism leads to the production of the desired product displaying full biological activity. The present invention therefore also comprises a polypeptide produced by a recombinant DNA technique, which polypeptide is one encompassed above. The invention further comprises a synthetic, or protein-engineered, polypeptide encompassed above.

The present invention therefore further provides: a recombinant construct comprising any nucleic acid sequence according to the invention; a vector comprising such a construct; and a host transformed or transfected by such a vector.

The present invention therefore still further provides a cultured or non-human cell, plasmid, virus, live organism or other vehicle that has been genetically- or protein-engineered to produce a polypeptide according to the present invention, said cell, plasmid, virus, live organism or other vehicle having incorporated expressibly therein a sequence as disclosed herein. Such cells may include animal, such as mammal, for example human or humanised cells, for use in gene therapy to treat or prevent conditions such as those mentioned herein. Such cells particularly include stem cells derived by cell nuclear transfer in accordance with the present invention. The present invention therefore also further provides animal clones derived from nuclear transfer techniques enhanced by using the PLC-zeta of this invention.

Therefore, the present invention further provides a method for the preparation of a polypeptide according to the present invention, which method comprises:
(a) isolation and/or purification from mammalian sperm; or
(b) expression of a nucleic acid sequence encoding the polypeptide and, optionally, isolation and/or purification of the resulting polypeptide.

The present invention therefore comprises inter alia the human, mouse, rat or other mammalian protein PLC-zeta, or non-mammalian (e.g. fish) PLC-zeta, the nucleic acid sequence coding therefor, cells transfected with the nucleic acid sequence, and a process for producing PLC-zeta by cultivation of the transfected cells and recovery of the expressed product.

The recombinant proteins, especially the mouse (including the c-Myc-tagged mouse), monkey (both AB 070108 and AB070109) and human PLC-zeta, have been shown to generate cytoplasmic calcium oscillations (CCOs) when introduced into mammalian cells. Furthermore, the injection of complementary RNA (cRNA) encoding PLC-zeta into mouse eggs also generates identical CCOs to those observed when they are fertilized by sperm. It has also been found that PLC-zeta is capable of producing embryo development to the blastocyst stage (i.e. the stage at which stem cells are found).

Accordingly, the invention also provides a variety of applications and/or uses of the proteins and nucleic acid sequences of this invention, including the following:

1. Treatment of Mammalian Infertility:

The human PLC-zeta; PLCζ protein we have identified may be used in treating human male infertility. This PLC-zeta; PLCζ protein triggers calcium changes upon sperm fusion with egg, the physiological process which results in egg activation and consequent embryo development. Absence or significant reduction of the level of active PLC-zeta; PLCζ in sperm would be expected to result in infertile males. That the PLC-zeta; PLCζ protein is highly expressed in mammalian testis is supported by the following:
(a) the cDNA has been isolated from testis cDNA libraries (human testis and mouse spermatid); and
(b) search of the EST database using our PLC-zeta; PLCζ sequences human and mouse reveals sequence matches found in testis-derived cDNA libraries.

Assay of the PLC-zeta; PLCζ protein in human sperm samples may therefore be used to identify males who have less than normal levels of the active protein (i.e. protein having the ability to cause cell calcium oscillations) and are infertile for this reason. This assay may be achieved by the use of antibodies to the protein prepared by methods well known to those skilled in the art.

To correct such deficiencies, the addition of active PLC-zeta; PLCζ to sperm lacking an active PLC-zeta; PLCζ can be carried out in conjunction with the clinical IVF (in vitro fertilization) technique of intra-cytoplasmic sperm injection, ICSI (Intra-Cytoplasmic Sperm Injection, comprising introduction of a single sperm directly into the egg). The ICSI procedure has been successfully used by major IVF clinics to produce thousands of live human births.

2. Improvement in Stem Cell Production:

The ethical use of 'spare' embryo-derived stem cells in therapy of human degenerative diseases has been of great public debate recently. The generation of stem cells directly from a patient would remove the need for use of donated embryos. Cloning of cells, tissues and animals (e.g. 'Dolly', the sheep) have been achieved by fusing a somatic cell with an enucleated egg. Activation of the fused egg to trigger development of the hybrid cell to form a blastocyst, from which stem cells can be harvested, is a very low efficiency process with <1% success rate. Thus, the application of a native protein with a physiologically relevant activity, that is, to trigger egg activation, following the fusion process occurring between the somatic cell and the egg cell, would enhance the success rate of fused cells in proceeding to develop further.

Stem cells derived from nuclear transfer techniques enhanced by using PLC-zeta have potential application to a variety of human diseases and conditions, including Parkinsonism, Alzheimer's disease, heart failure and diabetes, to which stem cell therapy could be applied.

3. Animal Cloning:

An extension of the application 2, above, is to implant the successfully developing blastocyst into a pregnant female host to produce full development to term and live birth of clones derived from a single adult animal cell. This process is currently being developed for the production of biomedicines in transgenic animals, e.g. sheep and pigs, as well as for the potential use of animal cells and organs for transplantation into humans but the current success rate for this procedure, as mentioned above is very low, <1%, due to the difficulties in achieving viable hybrid cells upon fusion.

In another aspect, the present invention provides a method for the treatment or prevention of a condition or disorder mentioned herein, wherein the polypeptide is administered by means of being expressed in the cells of the patient, which cells have incorporated expressibly therein a nucleic acid sequence coding for the polypeptide. Alternatively, cRNA may be administered to a cell to be treated. Alternative to gene therapy, the polypeptides of the invention may be administered as a pharmaceutical formulation.

However, we have surprisingly found there is a precise range of concentrations in which PLCζ can effectively trigger both egg activation and, importantly, embryo development.

According to another aspect of the invention there is therefore provided an effective amount of human PLCζ to enable development after fertilisation of a human oocyte characterised in that said effective amount of human PLCζ is between 150 and 450 femtograms per human oocyte.

According to a further aspect of the invention there is provided a fertilisation fluid for injecting into a human oocyte wherein said fluid is characterised in that the injected volume contains between 150 and 450 femtograms of human PLCζ.

According to a further aspect of the invention there is provided the use of human PLCζ in the manufacture of a medicament to treat infertility wherein the medicament is formulated so that the amount of human PLCζ, when transferred to an oocyte, is between 150 and 450 femtograms.

Accordingly, the present invention provides the use of a polypeptide described herein or a nucleic acid sequence coding for the polypeptide in medicine, including gene therapy; and also the use of such a polypeptide in the manufacture of a medicament.

Therefore, according to a further aspect of the present invention, there is provided a pharmaceutical formulation comprising a polypeptide according to the invention (as described above) and a pharmaceutically acceptable carrier therefor. The term "pharmaceutically acceptable carrier" as used herein should be taken to mean any inert, non-toxic, solid or liquid filler, diluent or encapsulating material, or other excipient, which does not react adversely with the active ingredient(s) or with a patient.

Such formulations and carriers are well known in the art and include pharmaceutical formulations that may be, for example, administered to a patient systemically, such as parenterally, or orally or topically.

The term 'parenteral' as used here includes subcutaneous, intravenous, intramuscular, intra-arterial and intra-tracheal injection, and infusion techniques. Parenteral formulations are preferably administered intravenously, either in bolus form or as a continuous infusion, or subcutaneously, according to known procedures. Preferred liquid carriers, which are well known for parenteral use, include sterile water, saline, aqueous dextrose, sugar solutions, ethanol, glycols and oils.

Tablets and capsules for oral administration may contain conventional excipients such as binding agents, fillers, lubricants, wetting agents, and the like. Oral liquid preparations may be in the form of aqueous or oily suspensions, solutions, emulsions, syrups, elixirs or the like, or may be presented as a dry product for reconstitution with water or other suitable vehicle for use. Such liquid preparations may contain conventional additives, such as suspending agents, emulsifying agents, non-aqueous vehicles and preservatives.

Formulations suitable for topical application may be in the form of aqueous or oily suspensions, solutions, emulsions, gels or, preferably, emulsion-based ointments.

Unit doses of the pharmaceutical formulations according to the invention may contain daily-required amounts of the polypeptides, or sub-multiples thereof to make a desired dose. The optimum therapeutically-acceptable dosage and dose rate for a given patient (which may be a mammal, such as a human) depend on a variety of factors, such as the potency of the active ingredient(s); the age, body weight, general health, sex and diet of the patient; the time and route of administration; rate of clearance; the object of the treatment (for example, treatment or prophylaxis); and the nature of the disease to be treated.

It is expected that systemic doses in the range of from 0.005 to 50 mg/kg body weight, preferably of from 0.005 to 10 mg/kg and more preferably 0.01 to 1 mg/kg, will be effective. According to the nature of the disease being treated, one single dose may comprise in the range of from 0.005 to 10 mg/kg body weight active ingredient, whether applied systemically or topically.

The present invention therefore further provides:
(a) the use of a polypeptide of this invention in therapy;
(b) the use of a polypeptide of this invention in the preparation of a medicament;
(c) a method for the treatment or prevention of a condition in a patient, which condition involves suppression, inhibition or inactivation of the generation of CCOs, which method comprises administration to said patient of a non-toxic, inhibitory amount of a polypeptide of the invention;
(d) the use of a polypeptide of this invention in the generation of CCOs in mammalian cells;
(e) a method of treating male infertility in a mammal, which method comprises adding the polypeptide of this invention to the sperm of the mammal; and
(f) a method of improving oocyte-somatic cell nuclear transfer efficiency in cell cloning, which method comprises adding a polypeptide according to this invention, or nucleic acid encoding the polypeptide, to an oocyte before or after fusion with the contents of a somatic cell.

Furthermore, the protein or nucleic acid sequence coding therefor according to this invention may be used in a diagnostic method to determine the state of fertility (e.g. whether fertile or infertile) of a respective mammal, such as a human.

Accordingly, the present invention further provides a diagnostic method for determining the fertility status of a mammal, which method comprises determining the amount of a protein according to this invention, or nucleic acid sequence coding therefore, present or absent in a test sample obtained from the mammal, which amount is indicative of the level of fertility of the mammal.

According to a further aspect of the invention there is provided a diagnostic or screening method for determining the fertility status of a human male comprising.
a) using a sample of sperm obtained from said human male to determine the concentration of human PLCζ contained therein by:
b) measuring the amount of human PLCζ in each sperm cell and where the concentration is less than 150 femtograms;
c) concluding that the male is likely to be infertile.

According to a yet further aspect of the invention there is provided a method for treating male infertility comprising:
a) using a sample of sperm obtained from a human male wherein the concentration of human PLCζ per sperm cell has been determined to be less than 150 femtograms;
b) supplementing the amount of human PLCζ so that it falls within a range of between 150 and 450 femtograms;
c) using the supplemented sperm cell to activate or fertilise a selected oocyte.

Reference herein to the term activate includes reference to the enablement of development following fertilisation.

In a preferred method of the invention supplementing the sperm cell to increase the amount of human PLCζ may be undertaken by directly injecting or inserting a suitable amount of PLCζ protein therein or, alternatively, genetic manipulation may be performed such that the sperm cell expresses an increased amount of human PLCζ (over the above that it would normally express without genetic manipulation), or RNA may be administered to the cell so that the total amount of human PLCζ expressed by the sperm cell is between 150 and 450 femtograms.

According to a further aspect of the invention there is provided a diagnostic or screening method for determining the fertility status of a human male comprising:
a) using a sample of sperm obtained from said human male to determine the concentration of human PLCζ contained therein by:
b) measuring the amount of human PLCζ in each sperm cell and where the concentration is more than 450 femtograms;
c) concluding that the male is likely to be infertile.

According to a yet further aspect of the invention there is provided a method for treating male infertility comprising:
a) using a sample of sperm obtained from a human male wherein the concentration of human PLCζ per sperm cell has been determined to be more than 450 femtograms;
b) blocking the activity of a fraction of said PLCζ so that the active amount of PLCζ able to promote development of a female oocyte to the blastocyst stage and beyond is between 150 and 450 femtograms;
c) using the blocked sperm cell to activate or fertilise a selected oocyte.

According to a further aspect of the invention there is provided a method of contraception for safeguarding against human fertilisation comprising:
a) using a sample of sperm obtained from a human male wherein the concentration of human PLCζ has been determined to be less than 450 femtograms; and
b) supplementing the amount of human PLCζ so that the concentration per sperm cell is in excess of 450 femtograms.

In a preferred embodiment of the invention supplementing the sperm cell to increase the amount of human or PLCζ is undertaken by genetic manipulation such that the sperm cell expresses an increased amount of human PLCζ (over the above that it would normally express without genetic manipulation), or RNA may be administered to the cell so that the total amount of human PLCζ expressed by the sperm cell is greater than 450 femtograms.

In all the above aspects of the invention the range of PLCζ is expressed as 150-450 femtograms, but more ideally 170-410 femtograms are preferred.

A further diagnostic or screening method comprises:
(a) obtaining a test sample comprising a nucleotide sequence of the mammalian PLCζ gene from the individual; and
(b) comparing a region of the sequence obtained from the test sample with the corresponding region of a wild type mammalian PLCζ sequence, such as [SEQ ID NO: 3, 4, 5, 6, 8 or 10]
whereby a variation in the sample sequence relative to the predetermined sequence is indicative of a condition, such as lowered fertility or infertility, associated with disruption in calcium oscillation patterns that are a prerequisite to normal biological function absent the condition.

Preferably, the test sample comprises genomic DNA.

A particularly preferred screening method is one for screening an individual suspected of a fertility problem, which screening method comprises the steps of:
(a) obtaining a test sample comprising a nucleotide sequence of the human PLCζ gene or an amino acid sequence encoded thereby from the individual; and
(b) analysing the test sample for the presence of a variant of the human PLCζ gene or an amino acid sequence encoded thereby or for the presence of one or more surrogate markers that are indicative of or correlated to the presence of a variant of the human PLCζ gene or an amino acid sequence encoded thereby,
wherein the variant of the human PLCζ, gene or an amino acid sequence encoded thereby exhibits at least one variation when compared to the wild type PLCζ sequence.

It will be evident to the person skilled in the art that the above methods apply equally to other mammals than humans and to other animals than mammals.

The analysis step (b) may be selected from one or more of: conventional protein sequencing methods (such as mass spectroscopy, micro-array analysis, pyrosequencing, etc), and/or antibody-based methods of detection (e.g. ELISA). In any of the methods according to the invention, antibodies to the protein may be raised. Therefore, in a method of testing for male infertility, which method comprises assaying the protein PLCζ in a sperm sample, the method could be carried out using an antibody to the protein, in particular, a monoclonal antibody to the protein PLCζ. Alternatively, the PLC-zeta gene sequence may be determined in a sample comprising genomic DNA, using methods known to those skilled in the art, such as PCR amplification, restriction enzyme analysis and DNA sequencing.

Accordingly, the present invention still further provides an antibody raised to a polypeptide according to the invention, particularly a monoclonal antibody thereto.

The screening method may comprise the use of simultaneous screens for multiple, known variations or for all possible variations by hybridization of a labelled sample of DNA (cDNA or genomic DNA derived from the individual) to micro-arrays of variation-specific oligonucleotide probes immobilised on a solid support. For example, chip technology may be used, wherein the chip is a miniature parallel analytical device.

The methods of the invention may be carried out using a kit, which kit may comprise:
(a) an oligonucleotide comprising a nucleic acid sequence corresponding to a region of a PLCζ variant, which region incorporates at least one variation from the corresponding wild-type PLCζ gene sequence; and/or
(b) an oligonucleotide comprising a nucleic acid sequence corresponding to the wild-type PLCζ gene sequence in the region specified in (a); and/or
(c) an oligonucleotide comprising a nucleic acid sequence corresponding to a specific region of the wild-type PLCζ gene sequence, which specific region comprises a sequence not otherwise present in the genomic DNA of the mammal; and/or
(d) antibodies, such as monoclonal antibodies, raised to any peptide sequence corresponding to an oligonucleotide specific to any one of (a) to (c) above; and, optionally,
(e) one or more reagent(s) suitable for amplifying (e.g. by carrying out PCR) desired regions of the individual's DNA.

Preferably, any of kit components (a) to (c) comprise(s) a plurality of said oligonucleotides immobilised on a solid support.

In a further aspect, the present invention provides an inhibitor or antagonist of PLC-zeta for use in reducing, suppressing or preventing cytoplasmic calcium oscillations in oocytes and/or for reducing or inhibiting fertility. Such PLC-zeta inhibitors or antagonists may comprise known chemical compounds, biological material or other agents, or may comprise new active agents. Accordingly, the invention further provides an active agent suitable for reducing, suppressing or preventing cytoplasmic calcium oscillations in oocytes and/or for reducing or inhibiting fertility, which active agent is an inhibitor or antagonist of PLC-zeta. Such active agents may be provided in the form of a pharmaceutical formulation in association with a pharmaceutically acceptable carrier therefore, as described above, and may be suitable for use as a male contraceptive.

BRIEF DESCRIPTION OF THE DRAWINGS

The accompanying drawings incorporated in and forming a part of the specification serve to illustrate several aspects of the present invention, and together with the description serve to explain the principles of the invention. The invention will now be further described in the following, non-limiting, Examples, with reference to the accompanying FIGS. 1 to 20, in which

FIG. 4a: is a graph of the percentage of mouse eggs reaching 2-cell stage after 24 hours and morula/blastocyst stage after 96 hours, following micro-injection with PLC-zeta cRNA (0.02 mg/ml) or pathogenically activated with strontium (5 mM, 4 hours) or fertilised with sperm in vivo and placing in a 5% $CO_2$ incubator at 37 C;

FIG. 4b: comprises two micrographs illustrating mouse embryos at the 2-cell stage and blastocyst stage, respectively, following the treatment illustrated in FIG. 4a;

Figure 1:
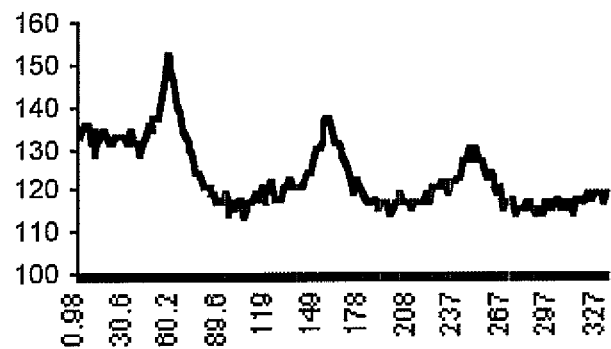
FIG. 1: is a plot of calcium concentration (nM; ordinate) with time (secs; abscissa), showing expression of mouse PLC-zeta plasmid DNA by transfection in CHO cells.

Table 2 shows the genomic organization of the human PLC-zeta gene. The gene is localized to chromosome 12p12.3.

DETAILED DESCRIPTION OF THE ILLUSTRATED EMBODIMENTS

Example 1

Isolation of the Nucleic Acid/Protein by PCR Cloning (Human)

The human expressed sequence tag (EST) database at NCBI (National Center for Biotechnology Information, National Library of Medicine, National Institutes of Health, Bethesda, Md. 20891, U.S.A.) was searched using the BLAST algorithm for phospho-inositide-specific phospholipaSe C-related sequences using the published sequence of the rat phospholipase C delta 4 isoform (NCBI accession number U16655-). Of the numerous positive 'hits' that were obtained, a class of novel ESTs was observed to be derived from human testis cDNA (eg accession numbers AI217888; AA707583; AA861064; AA609626).

Using the same approach for database searching as above, the mouse EST database at NCBI gave a related class of novel ESTs derived from mouse testis cDNA (e.g. accession numbers AV257260, AV277909, AV273316, and AV277562).

All these ESTs represent partial testis cDNA sequences (comprising fewer than 400 base pairs), as a complete open reading frame (ORF) was not identified in any of them.

Using polymerase chain reaction (PCR) cloning techniques with specific oligonucleotides designed to amplify sequences related to those ESTs described above, the complete protein coding sequence of the human and mouse phospholipase C-zeta; PLCζ were obtained as follows:

The primers used for PCR from a human testis cDNA library (Clontech Laboratories 1020 East Meadow Circle, Palo Alto, Calif. 94303-4230, U.S.A. #HL5503u) were:

```
Forward human primer:
5' CAG CGA GCT CTT ATC TGA CGT ACC AAA C 3'
(SEQ ID NO: 12; 28mer)

Reverse TriplEx primer:
5' CTC GGG AAG CGC GCC ATT GTG TTG GT 3'
(SEQ ID NO: 13; 26mer)
```

The forward primer was derived from the human EST sequences and included the predicted stop codon TGA, underlined. The reverse primer encoded the Clontech lambda TriplEx2 vector sequence. PCR was performed in a 50 uL reaction volume with initial denaturation at 96° C. for 3 minutes, followed by 30 cycles of 94° C. for 30 seconds, 60° C. for 30 seconds and 72° C. for 3 minutes, and a final extension at 72° C. for 5 minutes. The single ~2 kilobase product amplified using these primers with Pfu DNA polymerase, according to manufacturer's instructions (Promega Corporation catalogue # M7745, Promega UK Ltd, Delta House, Chilworth Research Centre, Southampton SO16 7NS, U.K.), was cloned into the commercial vector pTOPO-Blunt and plasmids transformed into competent *E. coli* for plasmid DNA preparation according to manufacturer's instructions (Invitrogen Inc. catalogue no. K2800-20, Invitrogen BV, PO Box 2312, 9704 CH Groningen, The Netherlands). Plasmid DNA was isolated from *E. coli* cultures using Qiagen miniprep purification columns according to manufacturer's instructions (Qiagen cat. no. 12125, QIAGEN Ltd.—UK, Boundary Court, Gatwick Road, Crawley, West Sussex, RH10 9AX, U.K.).

The primers used for PCR from a mouse spermatid cDNA library (made using the lambda ZAP II vector (available from Stratagene Inc. 11011 North Torrey Pines Road, La Jolla, Calif. 92037, U.S.A.), provided by Dr. Paul Burgoyne, National Institute for Medical Research, London) were:

```
Forward mouse primer:
5' GCT AAC GCG TCA GTT ACA TGC GTC ACT C 3'
(SEQ ID NO: 14; 28mer)

Reverse T7 primer:
5' GTA ATA CGA CTC ACT ATA GGG C 3'
(SEQ ID NO: 15; 22mer)
```

The forward primer was derived from the mouse EST sequences and included the predicted stop codon TCA, underlined. The reverse primer encoded Stratagene lambda ZAP II vector sequence (T7 sequence). PCR was performed in a 50 uL reaction volume with initial denaturation at 96° C. for 3 minutes followed by 30 cycles of 94° C. for 30 seconds, 60° C. for 30 seconds and 72° C. for 3 minutes, and a final extension at 72° C. for 5 minutes. The single ~2 kilobase product amplified using these primers with Pfu DNA polymerase, according to manufacturer's instructions (Promega Corp.), was cloned into the commercial vector pTOPO-Blunt and plasmids transformed into competent *E. coli* for plasmid DNA preparation according to manufacturer's instructions (invitrogen Inc.). Plasmid DNA was isolated from *E. coli* cultures using Qiagen Miniprep™ purification columns according to manufacturer's instructions (Qiagen).

Nucleotide sequence analysis of the amplified and cloned human and mouse DNAs was determined by standard dideoxy sequencing performed on an Applied Biosystems ABI377 automated DNA sequencer using the dRhodamine dye terminator kit (PE Applied Biosystems, Kelvin Close, Birchwood Science Park North, Warrington, WA3 7PB, U.K.). Open reading frame (ORF) analysis of the complete human and mouse nucleotide sequences using MacVector sequence analysis software (Oxford Molecular, The Medawar Centre, Oxford Science Park, Oxford, OX4 4GA, U.K.) revealed the complete protein coding sequence of the human and mouse PLC-zeta; PLC□ proteins. The human sequence revealed an ORF of 1824 base pairs encoding a 608 amino acid sequence (SEQ ID NO: 1). The mouse sequence revealed an ORF of 1941 base pairs encoding a 647 amino acid sequence (SEQ ID NO: 2).

Identification and Cloning of Simian PLC-Zeta

A cynomolgus monkey cDNA library was prepared from size-selected, adult *Macaca fascicularis* testes cDNAs of >1.5 kb, and a number of novel, full-length insert DNA sequences were determined. Blast searching with the hPLC-zeta sequence revealed two homologous simian sequences derived from the adult *M. fascicularis* testis cDNA library (Accession numbers, AB070108 and AB070109). The ORF within these two cynomolgus monkey cDNA clones were amplified by PCR with Pfu DNA polymerase, as described above, cloned into pcDNA3.1-V5-His-TOPO (Invitrogen) (pcDNA-zeta) and the insert DNA sequenced along both strands, as described above. Homology sequence analysis and alignment was performed using ClustalW (www.clustal-w.genome.ad.jp) and domain structure by RPS-Blast (www.ncbi.nlm.nih.gov/structure/cdd).

Example 2

Preparation of Recombinant Vectors for Expression in Mammalian Cells

The complete ORF of both human and mouse PLC-zeta; PLCζ sequences were sub-cloned into the mammalian expression vector, pTargeT (Promega, Delta House, Chilworth Research Centre, Southampton SO16 7NS, U.K.). The full-length sequences were amplified by PCR with Pfu polymerase (Promega) as described above, using specific oligonucleotides designed to the start and stop codons as follows:

The human primers used were:

```
Forward human primer:
5' CAG CGA GCT CTT ATC TGA CGT ACC AAA C 3'
(SEQ ID NO: 16; 28mer)

Reverse human primer:
5' ATG AAA CTA TGG AAA TGA GAT GGT 3'
(SEQ ID NO: 17; 24mer)
```

The reverse human primer included the start codon, ATG, underlined, and the forward human primer included the stop codon as used in the original PCR cloning steps described above. PCR was performed as described above. The ~1.8 kilobase product was cloned into pTOPO-Blunt and the DNA insert was sequenced as described above. The ~1.8 kilobase human DNA insert was excised from the pTOPO-Blunt vector by digestion with the restriction enzyme EcoR1, the restricted fragment was separated by agarose gel electrophoresis, purified using the Qiagen DNA gel extraction kit and ligated into the EcoR1 pre-digested mammalian vector, pTarget. Ligation was performed at 12° C. overnight in the presence of 10 units of T4 DNA ligase (Promega), and ligated plasmid was transformed into competent *E. coli* XL-1 Blue (Stratagene), and plasmid DNA purified using Qiagen columns as described above. Restriction enzyme digestion of plasmid DNA revealed the clones containing the correct orientation of the human PLC-zeta; PLCζ insert.

The mouse primers used were:

```
Forward mouse primer:
5' GCT AAC GCG TCA GTT ACA TGC GTC ACT C 3'
(SEQ ID NO: 18; 28mer)

Reverse mouse primer:
5' ATC ATG GAA AGC CAA CTT C 3'
(SEQ ID NO: 19; 19mer)
```

The reverse mouse primer included the start codon, ATG, underlined, and the forward mouse primer included the stop codon as used in the original PCR cloning steps described above. PCR was performed as described above. The ~1.9 kilobase product was cloned into pTOPO-Blunt and the DNA insert was sequenced as described above. The ~1.9 kilobase mouse DNA insert was excised from the pTOPO-Blunt vector by digestion with the restriction enzyme EcoR1, the restricted fragment was separated by agarose gel electrophoresis, purified using the Qiagen DNA gel extraction kit and ligated into the EcoR1 pre-digested mammalian vector, pTargeT. Ligation was performed at 12° C. overnight in the presence of 10 units of T4 DNA ligase (Promega), and ligated plasmid was transformed into competent *E. coli* XL-1 Blue (Stratagene), and plasmid DNA purified using Qiagen columns as described above. Restriction enzyme digestion of plasmid DNA revealed the clones containing the correct orientation of the mouse PLC-zeta; PLCζ insert.

Example 3

Transfection of Human and Mouse Expression Plasmids into CHO Cells

The human and mouse pTargeT/PLCζ expression plasmid DNAs prepared as described in Example 2 were separately introduced, by a lipid-mediated transfection procedure, into the Chinese hamster ovary (CHO) cell line grown in tissue culture. CHO cells cultured in serum-containing media, DMEM, (Dulbecco's Modified Eagle Medium) to a density of 500,000 cells per culture dish, were transfected with 40 μg plasmid DNA plus 40 uL of Lipofectamine2000 (Life Technologies Ltd, 3 Fountain Drive, Inchinnan Business Park, Paisley, U.K.) in serum-free DMEM. After 15 hours, the CHO cells were returned to serum-containing DMEM.

In parallel, control experiments, identical CHO cells were treated in the same way with Lipofectamine but in the absence of plasmid DNA.

Example 4

Demonstration of Effectiveness—PLC4 in CHO Cells

Transfected cells prepared according to Example 3 were washed with culture medium 30 minutes after transfection, then incubated with the calcium-sensitive fluorescent indicator, fura-2-AM for 60 minutes. After further washing with medium, the cells were then placed on a microscope stage and the changes in cell calcium levels, as detected by the fluorescence of the fura-2, were monitored. Only in cells transfected with the PLCζ expression plasmid, the cell calcium level was observed to change periodically. This specific temporal behaviour of cell calcium, lie to produce calcium oscillations, is the same as that observed in eggs when fused with sperm at fertilization, and when soluble sperm proteins are injected directly into eggs. FIG. 1 demonstrates this with respect to mouse PLCζ. This indicates that the novel PLCζ proteins we have identified in human and mouse testis may be used to specifically control cell calcium levels in mammalian cells.

Example 5

Demonstration of Effectiveness—PLCζ in Oocytes

The open reading frame of human and mouse PLCζ cloned into the pTargeT vector as described in Example 2, were linearised by restriction, and complementary RNA (cRNA) encoding PLCζ was synthesized with a Ribomax RNA synthesis kit (Promega) then re-suspended in 120 mM KCl, 20 mM HEPES, pH 7.4. Mouse oocytes arrested at MII stage were harvested from female mice and loaded with fura 2-AM for 10 minutes, washed in H-KSOM and placed on a Nikon Diaphot stage. cRNA was micro-injected to 3-5% of egg volume and calcium was monitored as described by Swann, K in *Development* 110 1295-1302 (1990).

Figure 2:
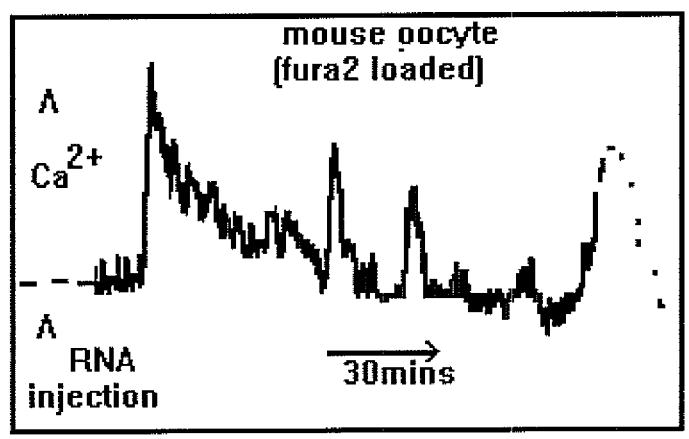
FIG. 2: is a plot of calcium concentration (nM; ordinate) with time (secs; abscissa), showing expression of mouse PLC-zeta complementary RNA by micro-injection into mouse eggs.
Figure 3:
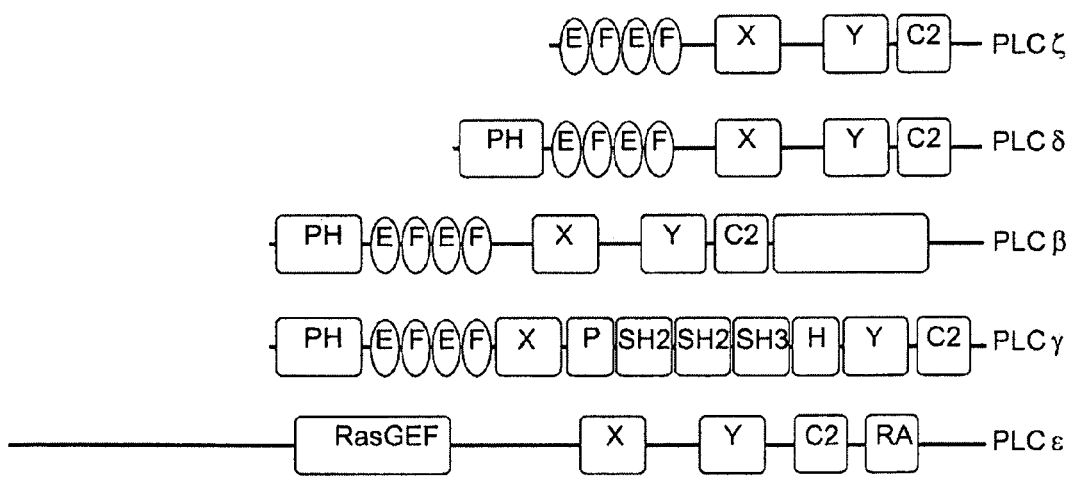
FIG. 3: is a schematic alignment of PLC regions, showing similarities and differences between PLC-zeta and other PLCs.

FIG. 2 demonstrates that mouse PLCζ in mouse eggs causes calcium oscillations. The data from the experiments of Examples 4 and 5 clearly show that PLCζ should have the effect of causing calcium oscillations in any cell type.

Example 6

Further Evidence that PLC-Zeta is Sperm Factor

Complementary RNA Synthesis and In Vitro Translation

The 1941 bp open reading frame of mouse PLCζ was cloned into pCR-Blunt II-TOPO, sequenced, and subcloned (pTarget, Promega) to generate pTarget-mPLCζ. Complementary RNA (cRNA) was synthesized from linearised pTarget-mPLCζ (Ribomax RNA synthesis, Promega) in the presence of 3 mM m$^7$G(5')ppp(5')G, isopropanol precipitated and resuspended in DEPC-treated water containing 4 U/ul RNasin (Promega). Mutagenesis of $^{210}$Asp to $^{210}$Arg in PLCζ to produce $^{D210R}$PLCζ was achieved using the QuikChange Site-Directed Mutagenesis Kit (Stratagene). Constructs and cRNAs for rat PLCδ1 and $^{ΔPH}$PLC δ1, which encoded the full-length (756 amino acids) and PH domain-deleted PLCδ1 (Δ1-132), respectively, and $^{D210R}$PLCζ were produced in pTarget as above. cRNA (2 ug) was expressed in vitro (Reticulocyte lysate system, Promega) in the presence of [$^{35}$S]methionine (Amersham Pharmacia). Radiolabelled protein, analysed by SDS-PAGE and autoradiography, was displayed using QuantityOne software (BioRad).

c-Myc-Epitope Tagging, Bacterial Expression and PLCζ Quantitation

The 1941 bp open reading frame of mouse PLCζ was subcloned into pGBK-T7 (Clontech) with an in-frame c-Myc epitope tag at the 5'-end (Lopez et al J Biol Chem 276 2758-2765 (2001)). The c-Myc-PLCζ was further subcloned into pcDNA3.1 and sequence-verified before cRNA synthesis from the T7 site (Ribomax) for egg micro-injection, as described above. For bacterial expression, c-Myc-PLCζ was subcloned into pBAD (Invitrogen) with an in-frame hexahistidine tag at the 3' end. The c-Myc-PLCζ-Histag protein was produced in 0.2% w/v arabinose-induced, BL21(DE3)pLysS *E. coli*, after extraction of the pelleted bacteria by five freeze-thaw and ultrasonication cycles, then purified by nickel affinity chromatography (ProBond, Invitrogen). Protein Quantitation was Performed Using the BCA Protein Assay (Pierce) Densitometric analysis of the c-Myc-PLCζ band expressed in eggs micro-injected with different cRNA concentrations, c-Myc-PLCζ-Histag protein purified from *E. coli*, and calibrated sperm extract PLCζ derived from $10^4$-$10^6$ mouse sperm, employed a c-Myc monoclonal antibody (1:2000, Santa Cruz Biotechnology) and rabbit anti-PLCζ antiserum (1:1000), respectively, using QuantityOne software (Bio-Rad). A calibration standard plot, from analysis by immunoblot densitometry (Malek et al Biotechniques 6 1150-1153 (1997)) using the c-Myc antibody, was constructed using defined amounts of c-Myc-PLCζ-Histag protein, purified from *E. coli*, to enable the calculation of the relative c-Myc-PLCζ content in batches of 100 micro-injected eggs. For the quantitation analysis, expression of the c-Myc-PLCζ protein was assumed to be linear with time after cRNA micro-injection, as has been shown for micro-injected EGFP cRNA expressed in mouse eggs. This assumption was necessary because the c-Myc-PLCζ protein was below the detection limit within 3 hours of cRNA micro-injection. Hence, for a single mouse egg, the calculated 440-750 fg of c-Myc-PLC protein expressed 5 hours after micro-injection with 0.02 mg/ml cRNA, was equivalent to 44-75 fg expressed at 0.5 hours) (the time when the first Ca$^{2+}$ transient is normally observed). A separate calibration plot using the anti-PLCζ antibody was constructed with different c-Myc-PLCζ-Histag protein concentrations to enable estimation of the relative PLCζ content in defined numbers of mouse sperm.

Results are given in sections (a) to (c) below.

Immunodepletion of PLCζ from Sperm Extracts

Soluble extracts (Parrington et al Biochem J 341 1-4 (1999)) prepared from hamster sperm were incubated for 1 hour at 4° C. with control IgG or anti-PLCζ antibody that had been covalently attached to Protein G beads (1 mg/ml, Seize X Kit, Pierce). The PLCζ content of the supernatant and precipitated beads was determined by immunoblot analysis with anti-PLCζ antibody. Antibody-treated sperm supernatants were also analysed for $Ca^{2+}$ release activity by fluo-3 fluorometry with sea urchin egg homogenates, monitored using a Perkin-Elmer LS50B fluorimeter (as described by Jones et al in FEBS Letts 437 297-300 (1998)). They were also analysed for ability to generate CCOs by micro-injection into mouse eggs, as described below. Maximal immunodepletion of the sperm PLCζ protein was achieved by using an optimised ratio of antibody beads to sperm extract for each experiment (n=4). The optimal ratio was empirically determined for each sperm extract preparation as the minimum concentration of sperm extract (0.3-0.8 mg/ml) that still retains $Ca^{2+}$ release activity after treatment with the control IgG beads.

Results are given in section (d), below.

Preparation and Handling of Gametes

Mouse egg procedures were carried out either in HEPES-buffered KSOM or amino acid supplemented KSOM (Summers et al Human Reprod 15 1791-1801 (2000)). Female MF1 mice were super-ovulated by injection with 5 IU of PMSG followed 48 hours later by HCG (Intervet). Eggs were collected 13.5-14.5 hours after HCG, maintained in 100 µl droplets of H-KSOM under mineral oil at 37° C. and cRNA micro-injections performed within 1 hour. Expression of c-Myc-PLCζ in eggs was examined 5 hours after cRNA micro-injection, by adding SDS sample buffer to pelleted eggs and incubating at 95° C. for 5 minutes prior to SDS-PAGE, immunoblot then densitometric analysis with the c-Myc monoclonal antibody, as described above. Calibrated mouse sperm pellets were re-suspended in 10 mM Tris-HCl pH 7.5, 15 mM dithiothreitol (Perry et al Biol Reprod 60 747-755 (1999)), then subjected to 5 freeze-thaw cycles in liquid $N_2$ and centrifuged at 20,000×g at 4° C. for 10 minutes, before densitometric analysis of the soluble extract with PLCζ antibody, as described above. For in vitro fertilization studies, sperm were capacitated for 2-3 hours before adding to eggs. Egg activation and development studies were in H-KSOM containing 2 µM cytochalasin D for 4 hours. Further development to 2-cell stage, morula and blastocyst stage was carried out in 50 µl droplets of KSOM under mineral oil at 37° C. in a 5% $CO_2$ incubator.

Measurement of Intracellular $Ca^{2+}$ in MII-Arrested Mouse Eggs

Eggs loaded with 4 µM Fura red-AM (Molecular Probes) for 10 minutes were washed in H-KSOM and placed on a Nikon Diaphot stage. Loading media included sulfinpyrazone to prevent dye compartmentalisation and extrusion (Lawrence et al Development 124 223-241 (1997)). cRNA solutions in 120 mM KCl, 20 mM HEPES, pH 7.4, were micro-injected to 3-5% of egg volume as previously described (Swann 1990, ibid, Example 5). Protein synthesis was inhibited in control experiments where eggs were pre-incubated in solution containing 10 µM cycloheximide for 30 minutes prior to micro-injection with PLCζ cRNA (0.02 mg/ml; n=9). Injection volume was estimated from the displacement caused by bolus injection. $Ca^{2+}$ measurements were performed on a CCD-based imaging system as previously described (Lawrence et al, 1997; ibid), or a Zeiss Axiovert 100 with illumination from a monochromator (Photonics) controlled by MetaFluor v4.0 (Universal Imaging Corp).

Handling and Microinjection of Oocytes to Determine Physiologically Active Levels of PLC-Zeta MF1 female mice about 4-6 weeks were superovulated as described previously (Saunders et al., 2002; Larman et al., 2004). Oocytes were released from the oviduct ampulae into M2 medium (Sigma-Aldrich, Poole, Dorset, UK) with a needle 13-15 hr post-hCG followed by removal of the cumulus mass by 0.3 mg/ml hyaluronidase. Complementary RNA encoding the 608-residue human PLC, tagged via the C-terminus with firefly luciferase (hPLCζ-luc), was prepared as described previously (Nomikos et. al. 2005). Microinjection procedures were carried out as previously described (Saunders et al., 2002). Oocytes were injected to 3-5% egg volume with a solution containing different concentrations of hPLCζ-luc cRNA (0.05-0.5 µg/µl) and 1 mM Oregon Green BAPTA dextran (Invitrogen Ltd, Paisley, UK). In the control experiment, 0.5 µg/µl luciferase RNA was injected into oocytes before they were activated by $SrCl_2$ or hPLCζ-luc cRNA injection.

Measurement of Intracellular $Ca^{2+}$ and Luciferase Expression to Determine Physiologically Active Levels of PLC-Zeta Some of the injected oocytes were placed in a chamber with M2 medium (Sigma Aldrich, Poole, Dorset, UK) containing 1 mM luciferin, on the temperature-controlled stage of an inverted microscope. $Ca^{2+}$ oscillations were monitored by measuring the fluorescence of Oregon Green BAPTA dextran and luciferase expression was monitored by the luminescence. These measurements were both carried out on the same sets of oocytes using a Zeiss Axiovert S100 microscope with light from the stage directed towards a cooled intensified CCD camera (ICCD) with a bialkali-type photocathode-based intensifier cooled to 10° C. The microscope and ICCD camera were placed inside a custom-made dark box. This photon counting camera, dark box, and associated software was supplied by Photek Ltd (St Leonards on Sea, East Sussex, UK). In most experiments, the fluorescence was recorded first by exposing oocytes to excitation light (450-490 nm) and reducing the sensitivity of the ICCD camera to 10%, and then the luminescence was recorded by removing the excitation light and switching the ICCD camera to maximum sensitivity. The luminescence values in experiments represent the absolute number of measured photon counts per second, whereas the intensity of fluorescence is displayed in arbitrary units of intensity. The levels of luciferase protein corresponding to a level of luminescence was estimated by injecting oocytes with known amounts of recombinant luciferase protein (Sigma Aldrich, Poole, Dorset, UK) and then measuring the luminescence of these oocytes under the same conditions as those injected with hPLCζ-luc cRNA.

Culture and Analysis of Embryos to Determine Physiologically Active Levels of PLC-Zeta On each experimental day, some of the hPLCζ-luc-injected oocytes were imaged and some from the same batch were put into KSOM media (Summers et al., 2000), containing 5 µg/ml cytochalasin B for 6 hr. A separate batch of oocytes that were not injected with hPLCζ-luc were activated by 10 mM $SrCl_2$ in $Ca^{2+}$-free KSOM medium for 4 hr. After the pronuclei formation was checked, both types of activated oocytes were cultured in KSOM medium at 37° C. in a 5% $CO_2$ incubator for 96 hr. All the resulting blastocysts were incubated in 0.5% pronase to remove the zona pellucida. After washing in MS medium, blastocysts were incubated in 10% rabbit anti-mouse whole serum for 30 min, washed again with M2 medium, and then incubated in M2 medium containing 20% guinea pig complement, 30 μg/ml propidium iodide and 10 μg/ml Hoechst 33342 for 15 min. The embryos were rinsed quickly and mounted in glycerol onto a glass slide. The data were expressed as means±SE. To evaluate the statistical significance of differences between groups, we applied the Student's t-test to test for mean comparisons. A P level of 0.05 was considered statistically significant. All chemicals not otherwise specified were obtained from Sigma-Aldrich (Poole, Dorset, UK).

Microinjection of Human Oocytes to Determine Physiologically Active Levels of PLC-Zeta Human oocytes were obtained from the local IVF clinic. The oocytes were of two types. So called 'fresh' human oocytes were collected from women undergoing follicle reduction that is sometimes necessary as a result of an over-response to hormonal stimulation for interuterine insemination. So called 'aged' human oocytes were oocytes that had failed to show any signs of fertilization after normal IVF procedures and those collected from the IVF clinic>16 hours after initial insemination. Full consent was obtained from the patients for the use of oocytes. The research project was approved by the local research ethics committees and by the Human Fertilization and Embryology Authority (research license number R0161). Oocytes were microinjected with hPLCζ-luc RNA in the same way as described for mouse eggs (Yu et al. 2007). The luminescence from all injected oocytes was measured for 30 mins at 15-18 hours post-injection, by incubating eggs in M2 media containing 1 mM luciferin and placing them on the stage of a Nikon TE2000 microscope equipped with a photon counting camera (Photek ICCD). The amount of luciferase expressed was calibrated by injection of known amounts of recombinant luciferase protein (Sigma-Aldrich) into mouse eggs. After hPLCζ-luc injection of the human oocytes, they were placed in drops of Sidney IVF cleavage medium for 3 days followed by transfer to Sidney IVF blastocyst medium (COOK), both in a 6% $CO_2$ incubator. Their development was observed intermittently over 5 days. Activation was defined as the appearance of pronuclei. In some cases, oocytes were also injected with the $Ca^{2+}$-sensitive dye, Oregon Green BAPTA dextran, and then the fluorescence (reporting changes in $Ca^{2+}$) and the luminescence was monitored for 15-18 hours by switching between fluorescence and luminescence imaging modes (Campbell and Swann, 2006).

Results (a) PLCζ Triggers $Ca^{2+}$ Oscillations in Eggs

The defining character of the mammalian sperm factor is the ability to elicit CCOs that mimic the fertilization-associated transients displayed by mammalian eggs. To examine whether sperm PLCζ could trigger such CCOs, we introduced PLCζ complementary RNA (cRNA) by micro-injection into MII-arrested mouse eggs, as described previously for spermatogenic cell mRNA. Eggs micro-injected with a pipette concentration of 2 mg/ml PLCζ cRNA, corresponding to <0.1 mg/ml in the egg after a 3-5% injection volume, underwent a prolonged series of CCOs, similar to those shown in FIG. 2, that commence within 15-20 minutes. The high oscillation frequency is similar to that observed upon micro-injection of concentrated sperm extracts into mouse eggs. CCOs of similar amplitude, but lower frequency, were obtained with a 1000-fold dilution to 0.002 mg/ml PLCζ cRNA (FIG. 6a, middle trace; 0.0001 mg/ml in egg). None of the eggs treated with cycloheximide to block protein synthesis showed any $Ca^{2+}$ transients after PLCζ cRNA-micro-injection (0.02 mg/ml, n=9; FIG. 6a, bottom trace). Robust CCOs were observed in 100% of the eggs micro-injected with the four different PLCζ cRNA concentrations tested, ranging from 0.002-2 mg/ml (FIG. 6b). Importantly, the frequency, but not the amplitude, of CCOs varied with PLCζ cRNA concentration, directly matching the same phenomenon observed with different concentrations of sperm extract. The highest pipette concentration used, 2 mg/ml, produced CCOs with a mean interspike interval of 7.3±3.2 minutes (FIG. 6b). The lowest pipette concentration of PLCζ cRNA that gives oscillations within 2 hours of injection (0.002 mg/ml), displayed a mean interspike interval of 20.1±5.4 minutes (FIG. 6b). Both of these values are significantly different to the mean interspike interval produced with in vitro fertilization (IVF) of mouse eggs (12.1±5.8 minutes). However, the interspike intervals for 0.2 and 0.02 mg/ml PLCζ cRNA (13.6±3.2 and 12.7±6.0 minutes, respectively) are not significantly different from IVF.

(b) Fertilization-Like $Ca^{2+}$ Signals Via PLCζ

The CCOs at fertilization display some unique features. The first $Ca^{2+}$ transient invariably lasts longer than subsequent oscillations, and exhibits a set of intriguing, smaller sinusoidal increases on top of the main peak. Microinjection of a pipette concentration of PLCζ cRNA that produces an interspike interval matching IVF (i.e. 0.02 mg/ml; FIG. 6b), resulted not only in the same, longer initial $Ca^{2+}$ transient, but also displayed a similar pattern of smaller sinusoidal increases. The first $Ca^{2+}$ increase after 0.02 mg/ml PLCζ cRNA micro-injection matches the first IVF transient in both average duration (PLC; 2.8±0.6 minutes, n=39 versus IVF 3.0±0.7 minutes, n=16), and also in reproducibly producing the cluster of smaller $Ca^{2+}$ increases superimposed on the first transient. A concentration of 0.02 mg/ml PLCζ cRNA was used for subsequent micro-injection experiments, unless stated otherwise, to provide the precise $Ca^{2+}$ signaling conditions that are stereotypical of fertilization.

(c) Physiological Level of PLCζ in a Single Sperm

Figure 6:
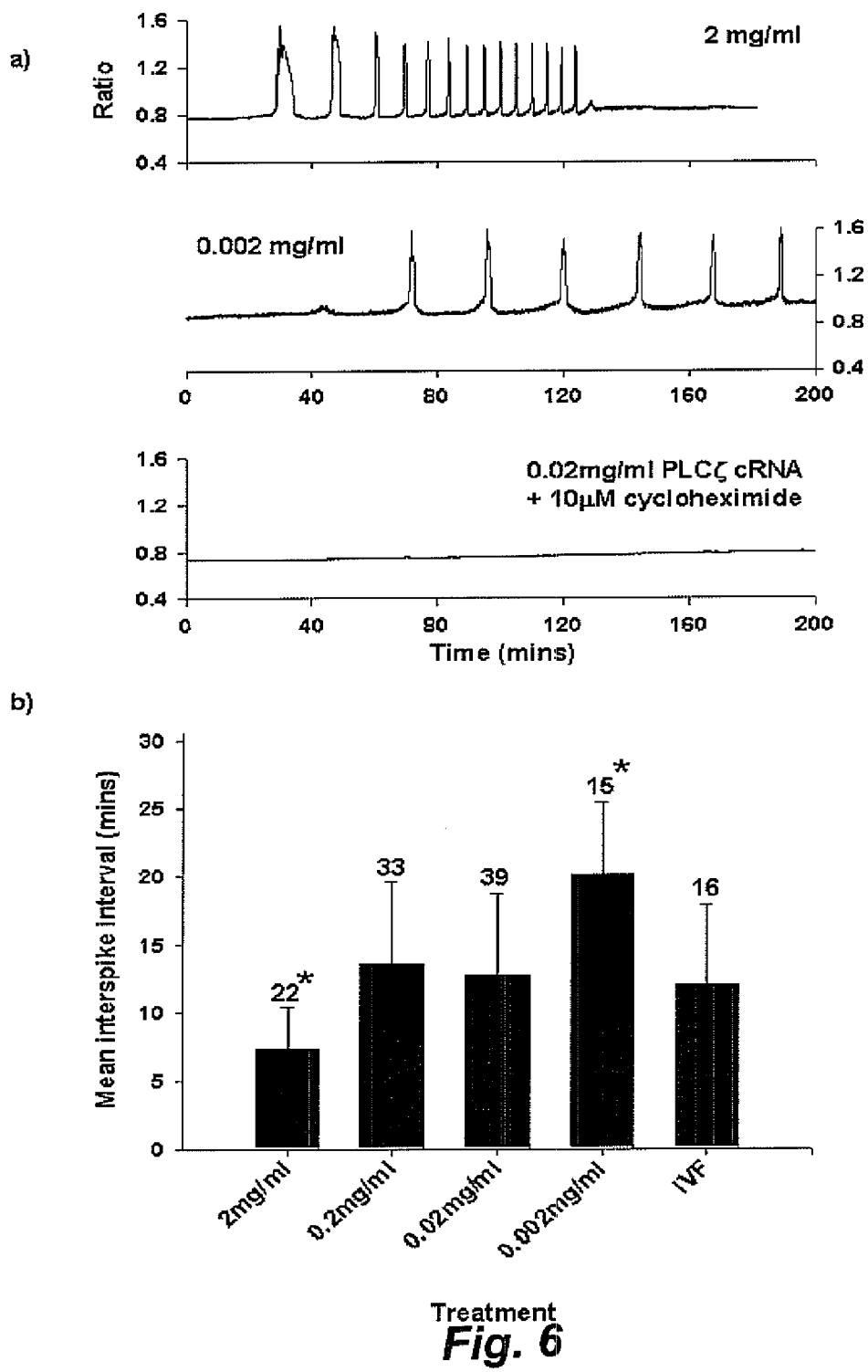
FIG. 6a: shows dose-dependent calcium oscillations in fura-red loaded mouse eggs, triggered by micro-injection of cRNA encoding mouse sperm PLC-zeta (2 and 0.002 mg/ml, top and middle travces, respectively) and after pre-incubation with 10 uM cycloheximide (0.02 mg/ml, bottom trace)
FIG. 6b: illustrates the mean interspike interval of calcium oscillations in eggs, following micro-injection of various PLC-zeta cRNA concentrations. Compared with the interval observed upon in vitro fertilisation (IVF). * indicates statistically significant (Student's unpaired t-test) from IVF at the 5% level.
Figure 7:
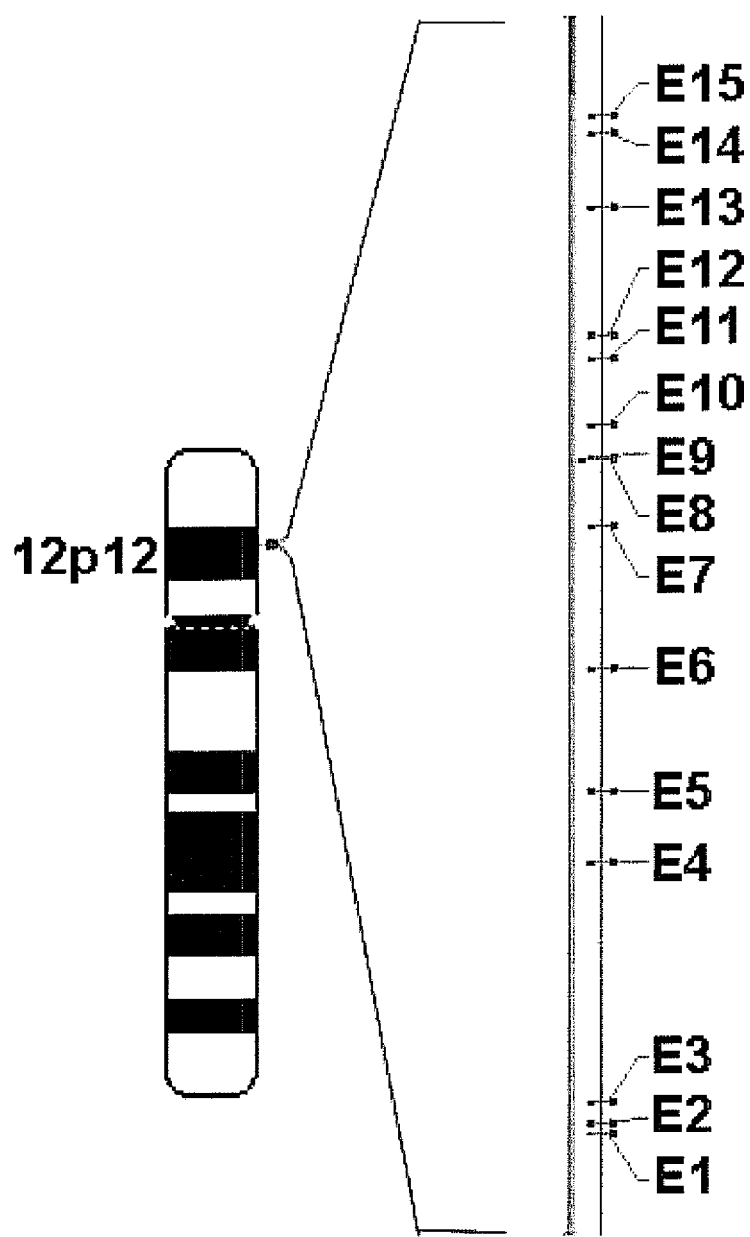
FIG. 7: Structure of the human plc-zeta gene. The genomic organisation of the fifteen plc-zeta exons identified within the 179456 bp contig (Accession number AC023940) are shown aligned to a 54.8 kb region of chromosome 12 (12p12.3). Exons are labelled E1 to E15. The start and stop codons for hPLCæ are located within E2 and E15, respectively. Solid line between exons represent the introns (see Table 2).

In order to quantitate the PLCζ expressed in micro-injected eggs, a c-Myc epitope tag was introduced at the N-terminus of PLCζ, as described above. Micro-injected c-Myc-PLCζ cRNA at different concentrations was as effective at generating $Ca^{2+}$ oscillations in eggs as the untagged PLC4, indicating that the N-terminal attachment of the c-Myc tag is not deleterious to PLC activity, as was shown for c-Myc-PLCζ. Furthermore, the c-Myc-PLCζ protein expressed in eggs was readily detected in immunoblots using an anti-c-Myc monoclonal antibody, as a single band with the predicted mass of 78 kDa, whereas uninjected eggs exhibited no immunoreactivity. Comparison of the relative mobility of native mouse sperm PLC4 (74 kDa) and recombinant c-Myc-PLCζ protein (78 kDa [74 kDa PLCζ+4 kDa c-Myc tag]) indicated that the deduced ORF of the PLCζ cDNA clone ([SEQ ID NO: 2], 74 kDa) represents the complete sperm PLCζ sequence. Densitometric analysis of the immunoreactive 78 kDa c-Myc-PLCζ protein expressed in eggs, compared with calibrated amounts of purified recombinant c-Myc-PLCζ protein produced in bacteria, enabled the determination of 44-75 fg/egg (n=4) as the amount of PLCζ protein that triggers $Ca^{2+}$ oscillations using 0.02 mg/ml cRNA. This cRNA concentration is the one that most closely mimics the IVF response, though ten-fold lower levels (i.e. 4-8 fg PLCζ protein/egg using 0.002 mg/ml cRNA) are also able to cause $Ca^{2+}$ oscillations (FIG. 6).

The PLCζ content of sperm was also determined by densitometry with a PLCζ polyclonal antibody using a defined number of mouse sperm and compared with calibrated amounts of recombinant PLCζ protein. Using densitometric values within the recombinant PLCζ protein calibration plot, obtained from samples comprising $10^4$-$10^6$ mouse sperm, a single mouse sperm was calculated to contain 20-50 fg PLCζ protein (n=4). The level of PLCζ able to produce $Ca^{2+}$ oscillations in a single egg similar to fertilization (4-75 fg, i.e. with 0.002-0.02 mg/ml cRNA) is therefore in the same range as the single sperm content of PLCζ (20-50 fg). The observed quantitative correlation indicates that the PLCζ from a single sperm is sufficient to produce the $Ca^{2+}$ oscillations observed upon sperm-egg fusion.

(d) Sperm PLCζ Depletion Abrogates $Ca^{2+}$ Oscillations

To address whether the PLCζ in sperm is uniquely responsible for $Ca^{2+}$ mobilisation in eggs, the PLCζ content of sperm extracts was specifically depleted using an anti-PLCζ antibody, as described above. Immunoblot analysis indicated that sperm extract supernatant retains the PLCζ protein after control antibody treatment, in contrast to PLCζ antibody-treated supernatant where the PLCζ is absent. Analysis of the corresponding precipitated antibody samples revealed that the sperm PLC4 is effectively removed by PLCζ antibody, but not by the control antibody. Assessment of $Ca^{2+}$ release activity in antibody-treated sperm extracts using sea urchin egg homogenate assays showed that PLCζ-depleted samples lack any $Ca^{2+}$ mobilising activity, whereas a robust $Ca^{2+}$ release was observed with the control antibody-treated sperm extract containing PLC4 protein. Moreover, micro-injection of antibody-treated sperm extracts into mouse eggs illustrated that the ability of untreated samples to generate IVF-like $Ca^{2+}$ oscillations is fully preserved in control antibody-treated samples, while PLCζ-depletion effectively abrogates $Ca^{2+}$ release activity.

These PLCζ antibody depletion experiments (n=4) suggest that PLCζ is the sole component of sperm extracts possessing the ability to cause $Ca^{2+}$ release in mouse eggs. Taken together with evidence that the PLCζ level in a single mouse sperm is sufficient to trigger IVF-like $Ca^{2+}$ oscillations in a single mouse egg, the immunodepletion data provides compelling evidence that PLCζ is synonymous with the previously described mammalian sperm factor.

(e) PLCζ Activates Normal Embryo Development

Since eggs that were micro-injected with PLCζ cRNA (0.02 mg/ml) displayed all the properties of $Ca^{2+}$ oscillations indistinguishable from those of IVF (Results (a) and (b) above) and is equivalent to the PLC4 content of a single sperm ((c) above), their ongoing development was monitored for several days after PLCζ-micro-injection.

PLCζ-micro-injected eggs underwent activation (FIG. 4a) because normal development proceeded to the 2-cell stage within 24 hours (78%, n=147), and many reached the morula or blastocyst stages by 4-5 days (62%, n=76). None of the eggs micro-injected with buffer control reached the 2-cell stage, indicating activation as an artifact of micro-injection procedure did not occur. The proportion of PLCζ-induced embryos that developed to either the 2-cell, or morula and blastocyst stages, was the same as for eggs that are either parthenogenetically activated by strontium ions (n=75), or when embryos are collected at the 1-cell stage from female mice after in vivo fertilization (n=101) upon mating with males (FIG. 4a).

Figure 4:
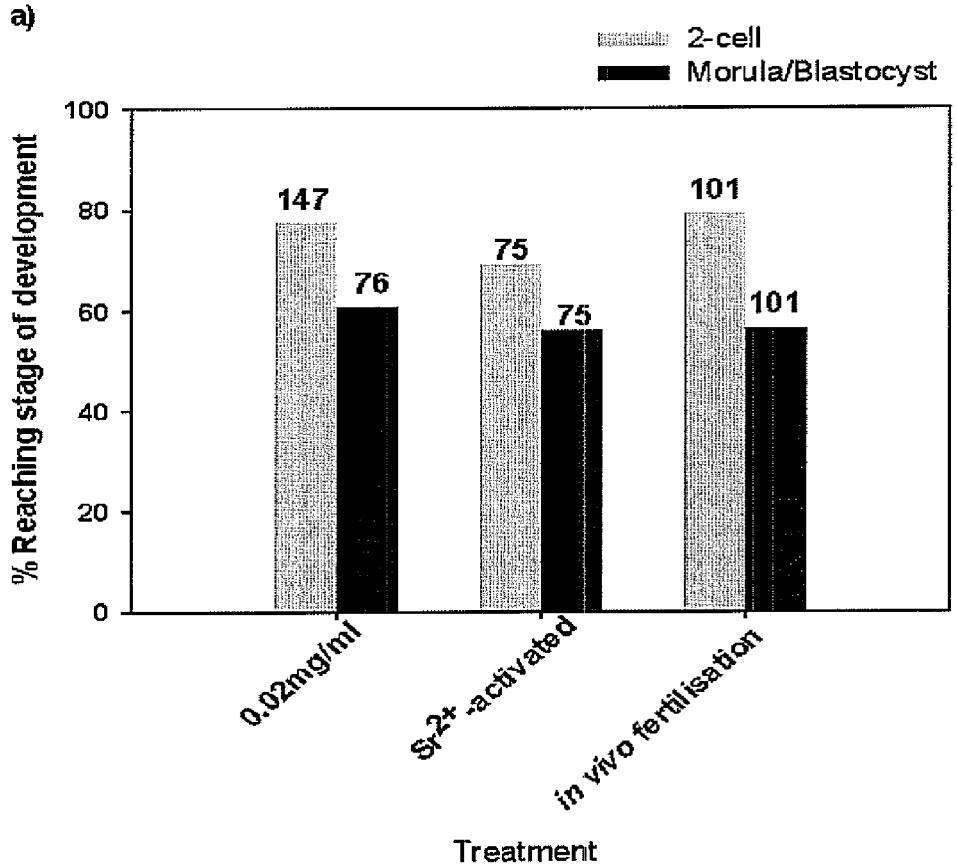
Figure 4:
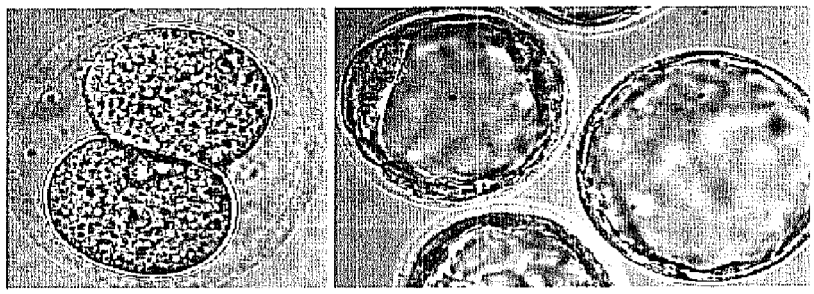

Photomicrographs taken at 24 hours and 5 days after PLCζ-micro-injection into mouse eggs show the appearance of normal embryo development to the 2-cell stage and blastocyst stage (left and right panel, respectively, FIG. 4b). There were no morphological differences to embryos obtained after fertilization with sperm. Thus, after inducing $Ca^{2+}$ oscillations in the egg, sperm PLCζ-micro-injection also triggered the entire cascade of events required for activation and embryo development, in the same manner as sperm at fertilization.

Figure 5:
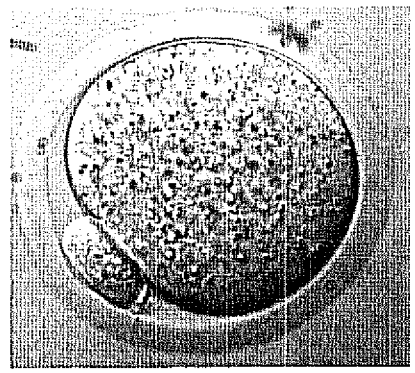
FIG. 5: is a micrograph illustrating mouse egg 24 hours following micro-injection with $^{D210R}$PLC-zeta, illustrating lack of development to 2-cell stage.

The possibility remained that a novel action of PLCζ other than $PIP_2$ hydrolysis is responsible for egg activation, such as a protein-protein interaction with a distinct egg molecule. To test whether an enzymatically active PLCζ is required for egg activation and embryo development, the $^{D210R}$PLCζ cRNA (0.02 mg/ml), which was shown to be defective in triggering $Ca^{2+}$ oscillations, was micro-injected, and egg activation assessed after 24 hours. None of the $^{D210R}$PLCζ cRNA-micro-injected eggs were found to proceed to the pronuclear or 2-cell stage (FIG. 5, n=20), suggesting that the enzymatic function of sperm PLCζ is critical for egg activation.

Human PLC-Zeta Triggers Ca Oscillations in Mouse Oocytes

Figure 8A:
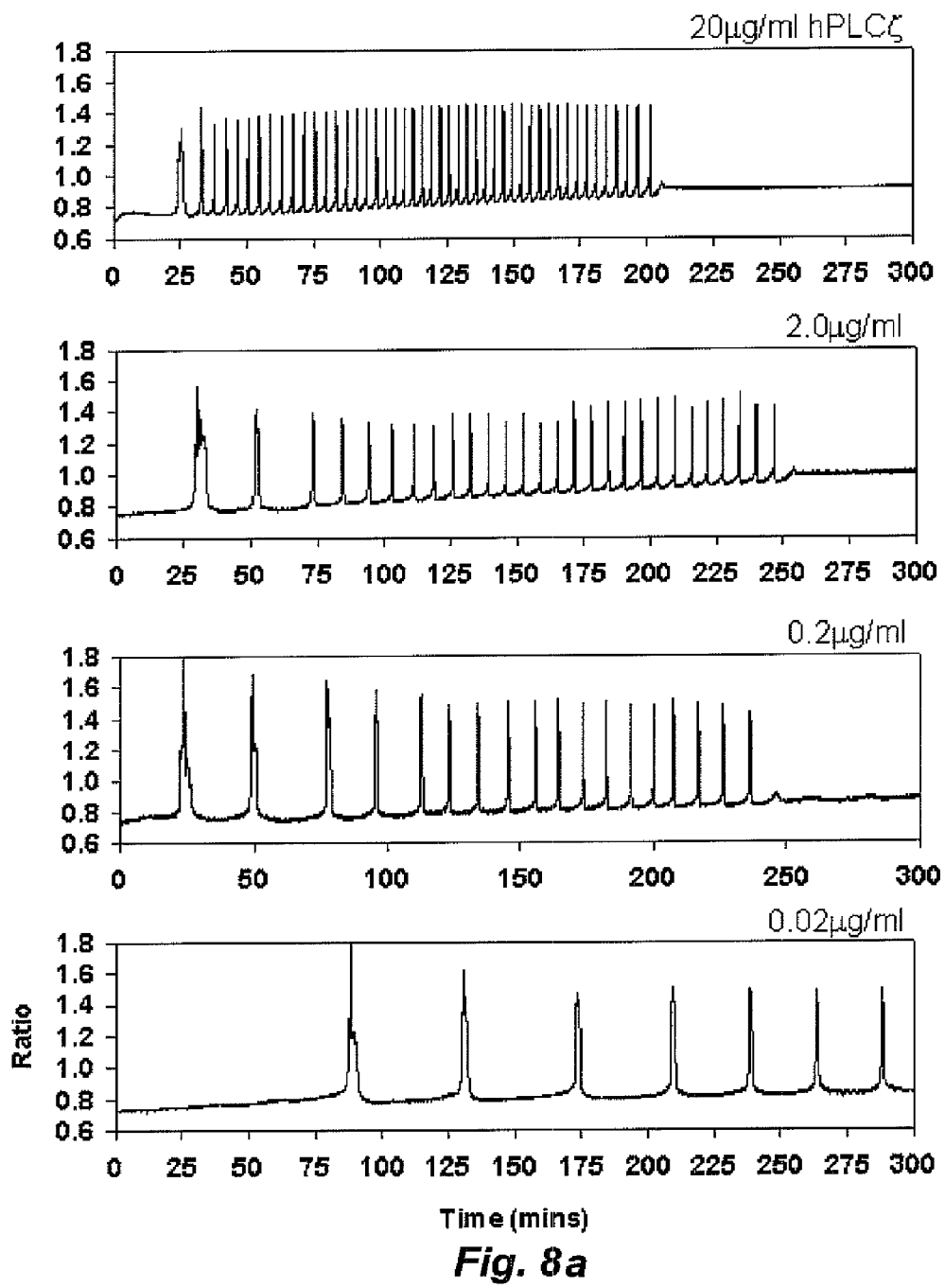
FIG. 8: Ca2+ oscillations in mouse oocytes microinjected with human PLC-zeta cRNA. A. Dose-dependent Ca2+ oscillations in MII-arrested mouse oocytes after microinjection of hPLC-zeta cRNA. The four traces show the cytoplasmic Ca2+ oscillations observed upon microinjection with cRNA at the indicated pipette concentration, from 20 to 0.02 μg/ml. B. Mean interspike interval of Ca2+ oscillations in mouse oocytes triggered by the various hPLC-zeta cRNA concentrations. The number of microinjected oocytes is shown above each dose. The mean interspike interval at each dose is statistically different from each other using a students paired t-test, p=<0.0001 (20 μg/ml, 4.21±1.79; 2.0 μg/ml, 9.26±7.14; 0.2 μg/ml, 16.0±6.40; 0.02 μg/ml, 24.34±7.68).
Figure 8B:
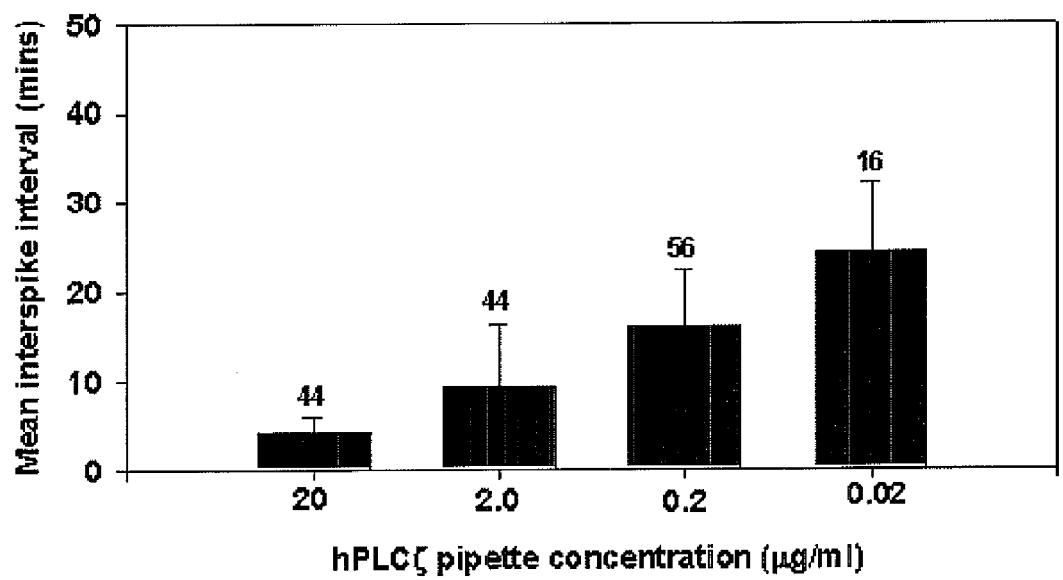

To examine the ability of hPLC-zeta to cause Ca2+ changes, cRNA for hPLC-zeta was microinjected into MII-arrested mouse oocytes with a pipette concentration of 20 µg/ml hPLC-zeta cRNA, which corresponds to 0.001 mg/ml in the oocyte after a 3-5% injection volume. FIG. 8A shows a representative example Ca2+ recording for each of the four different concentrations of hPLC-zeta cRNA that were microinjected. At 20 µg/ml hPLC-zeta cRNA triggered high frequency Ca2+ oscillations within 10-15 minutes of microinjection (mean interspike interval: 4.21±1.79 mins). As was observed with mouse PLC-zeta cRNA and hamster sperm extract microinjection, Ca2+ oscillations of lower frequency were obtained with lower concentrations of stimulus (Swann, 1990; Saunders et al, 2002). It was notable that even at pipette concentrations of 0.02 µg/ml, hPLC-zeta cRNA could still induce Ca2+ oscillations within two hours of microinjection. Although a wide range of cRNA concentrations from 20-0.02 µg/ml were used, the Ca2+ oscillations observed at each concentration lasted for a similar period of 3-4 hours (FIG. 8A). The mean interspike interval data showing the dose-response relationship with hPLC-zeta cRNA is summarised in the histogram in FIG. 8B.

Embryo Development with hPLC-Zeta

Figure 9A:
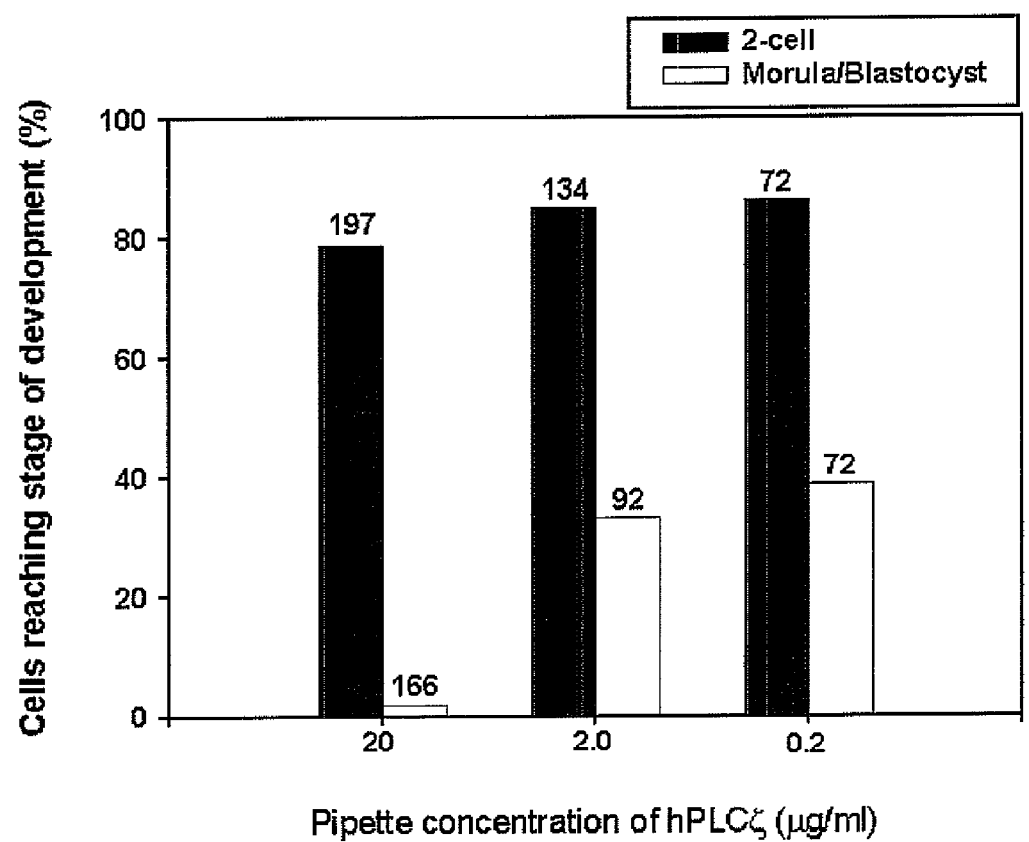
FIG. 9: Embryonic development of mouse oocytes microinjected with human PLC-zeta cRNA.
A. Mouse oocytes were microinjected with different hPLC-zeta cRNA concentrations (20-0.2 μg/ml). The percentage of oocytes reaching the 2-cell stage after 24 hours and morula/blastocyst after 96 hours were recorded.
B. Micrographs showing development of mouse embryos at the 2-cell stage (left) and blastocyst stage (right) following microinjection of unfertilized oocytes with hPLC-zeta cRNA (0.2 μg/ml).
Figure 9B:
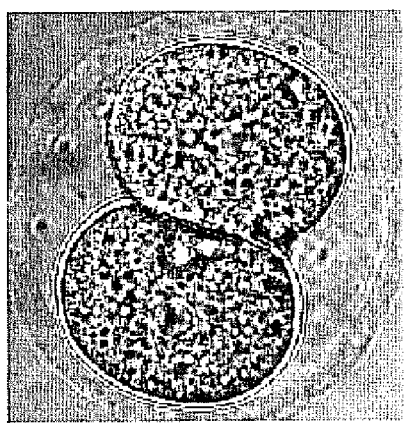
Figure 9B:
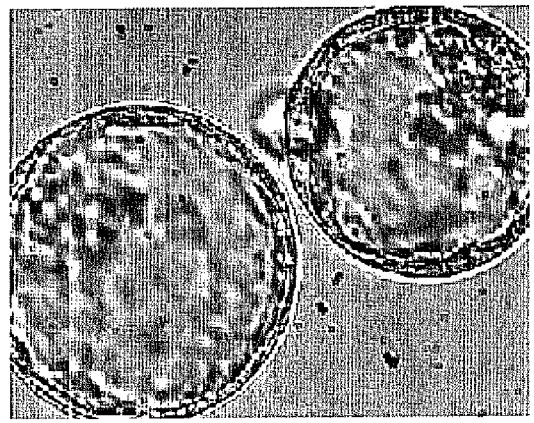

The microinjection of 20 µg/ml mPLC-zeta into mouse oocytes was previously demonstrated to induce $Ca^{2+}$ oscillations and development to the blastocyst stage at rates comparable to that of in vitro fertilization. To examine if hPLC-zeta is also able to support development, and what effect the oscillation frequency might have on embryo development, MII-arrested oocytes were injected with 20, 2.0 and 0.2 µg/ml hPLC-zeta cRNA and monitored after 24 h and 96 h. All three concentrations were affective at activating the oocytes and enabling development to the 2-cell stage (FIG. 9). Using 2.0 and 0.2 µg/ml hPLC-zeta cRNA, mouse embryo development to morula/blastocyst was 33.3 and 38.9%, respectively (FIG. 9A). This compares with developmental rates with in vivo fertilization and parthenogenetic activation of 55-60% under our conditions using outbred mouse strains. It was conspicuous, however, that the high Ca2+ oscillation frequency (low mean interspike interval) produced with 20 µg/ml was ineffective at supporting development to morula/blastocyst stages (1.8% of oocytes reaching morula/blastocyst) and most of these embryos arrested at the 2-cell stage.

Micrographs of the mouse embryos produced by hPLC-zeta cRNA microinjection show they are morphologically similar to those following in vitro fertilization (FIG. 9B), analogous to the observations with mPLC-zeta, though blastocyst cell numbers have not been determined. These data suggest that microinjection of hPLC-zeta cRNA into unfertilized eggs alone can trigger early embryonic development to blastocyst stages in mouse embryos, but it appears that the high frequency of Ca2+ oscillations caused by the higher doses of hPLC-zeta is detrimental to development beyond the 2-cell stage.

Simian PLC-Zeta Triggers Ca$^{2+}$ Oscillations in Mouse Oocytes

Figure 10A:
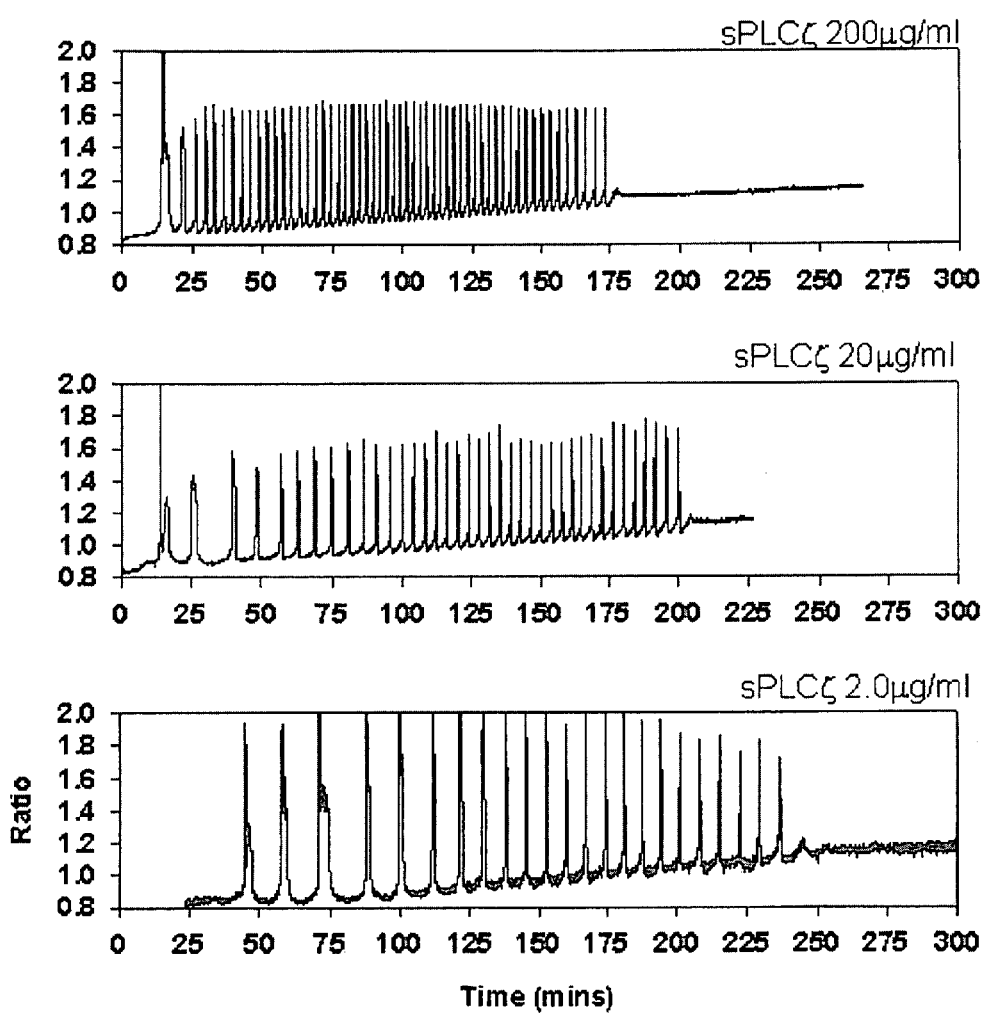
FIG. 10: Ca2+ oscillations in mouse oocytes with simian PLC-zeta cRNA.
A. Dose-dependent Ca2+ oscillations in MII-arrested mouse oocytes after microinjection of sPLC-zeta cRNA. The three traces show the cytoplasmic Ca2+ oscillations observed upon microinjection with cRNA at the indicated pipette concentration, from 200 to 2 μg/ml.
B. Mean interspike interval of $Ca^{2+}$ oscillations in mouse oocytes triggered by the various sPLC-zeta cRNA concentrations. The number of microinjected oocytes is shown above each dose. The mean interspike interval at each dose is statistically different from each other using a students paired t-test, p=<0.0001 (200 μg/ml, 3.18±0.55; 20 μg/ml, 7.35±2.69; 2.0 μg/ml, 15.77±5.20).
Figure 10B:
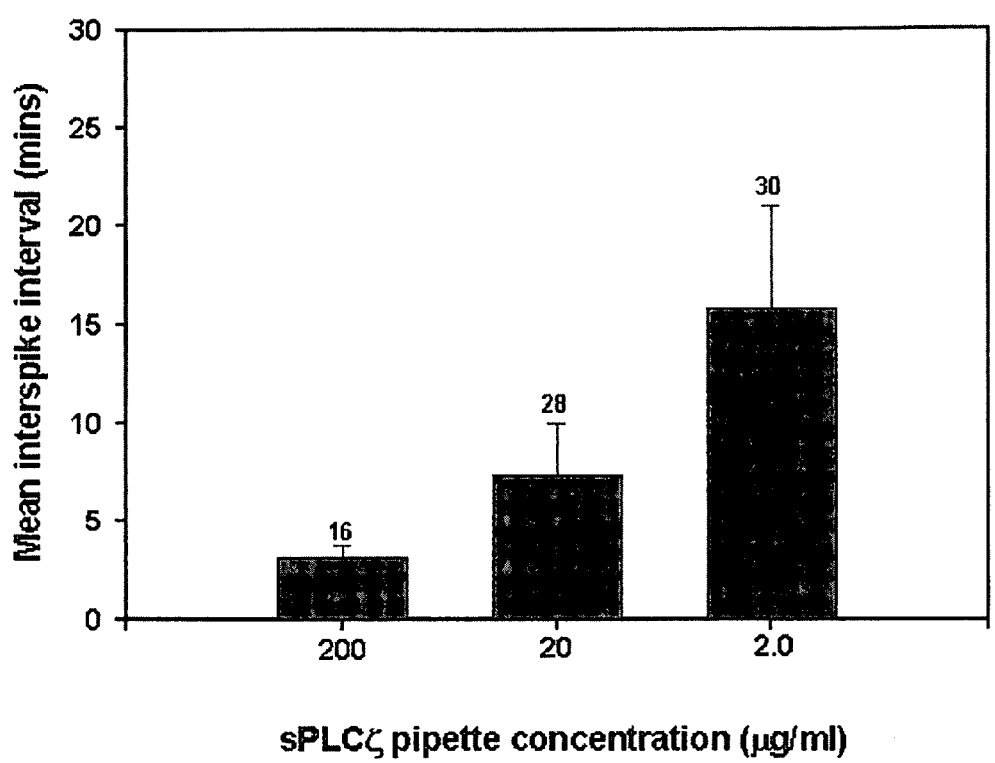
Figure 11:
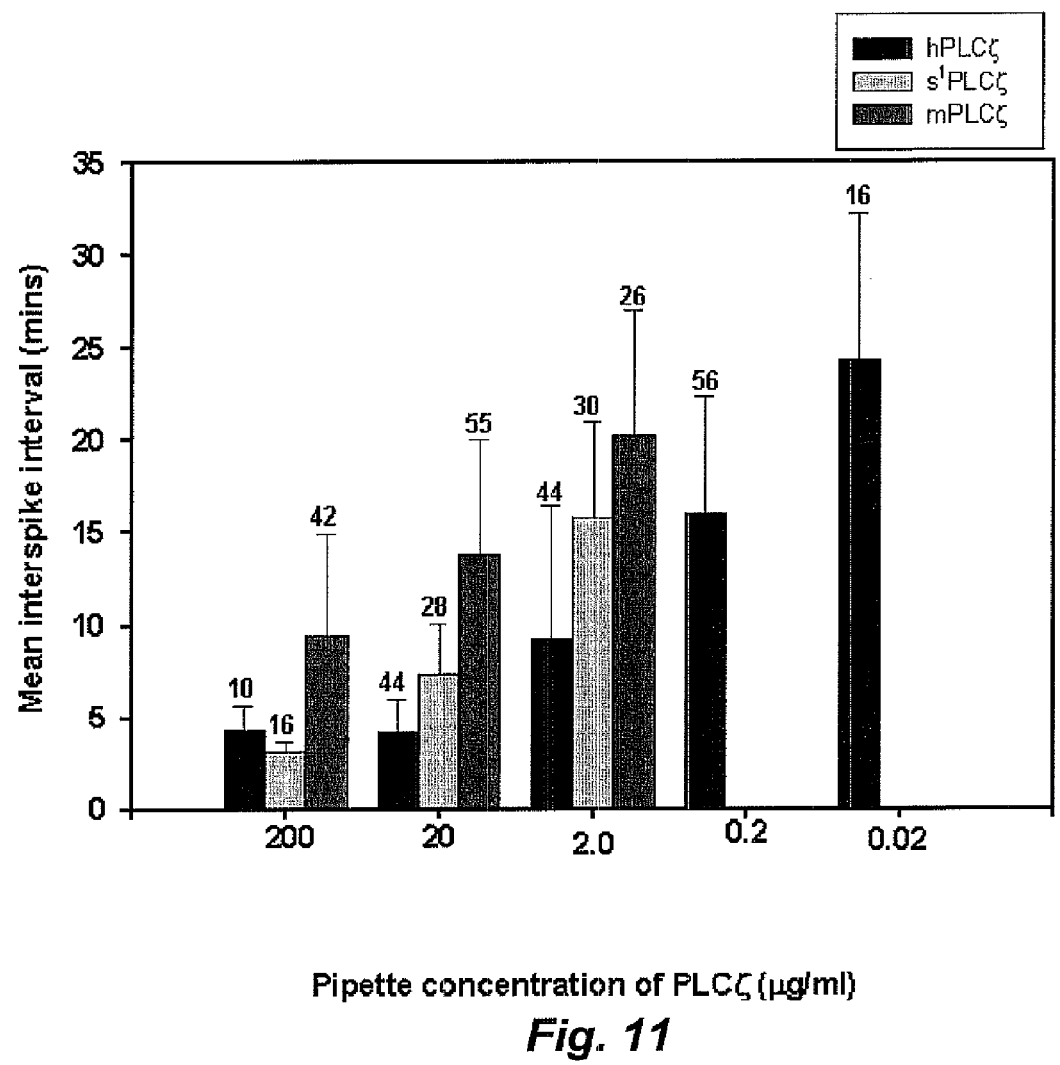
FIG. 11: Mean interpike intervals observed with human, simian and mouse PLC-zeta cRNA. Comparison of the mean interspike interval of $Ca^{2+}$ oscillations in mouse oocytes triggered by the three species of PLC-zeta cRNA. Human, simian and mouse PLC-zeta cRNAs each triggered Ca2+ oscillations within 2 hours of microinjection of 200-2.0 μg/ml PLC-zeta cRNA. Only hPLC-zeta was effective at the lower doses of 0.2 and 0.02 μg/ml. The number of oocytes microinjected is shown above each dose. The mean interspike interval at each dose for human, simian and mouse is statistically different from each other using a students paired t-test (p=<0.005).

The observations described above (FIGS. 8 and 9), show that the human and mouse PLC-zeta can cause fertilization-like Ca2+ oscillations that initiates activation and development of mouse oocytes. The identification of two related, testis-specific cDNA sequences of 2.3 kb from *M. fascicularis*, and the high degree of similarity of their ORF with the human and mouse PLC-zeta, enabled the prediction that these were simian PLC-zeta homologues. We therefore compared the ability of cRNA prepared from the two forms of sPLC-zeta, designated s1PLC-zeta and s2PLC-zeta (AB070108 and AB070109, respectively), to generate Ca2+ oscillations in mouse oocytes. Both forms were able to trigger Ca2+ oscillations and no functional difference was detected upon microinjecting either s1PLC-zeta or s2PLC-zeta cRNA (data not shown). For all subsequent experiments s1PLC-zeta was used (AB070108). FIG. 10A shows that s1PLC-zeta cRNA triggered dose-dependent Ca2+ oscillations in mouse oocytes comparable to those seen with human and mouse PLC-zeta, at each of the three doses tested (0.2, 0.02, 0.002 mg/ml). Similar to the data with human PLC-zeta, (FIG. 8A), the period over which Ca2+ oscillations occurred was 3-4 hours for each of the three s1PLC-zeta cRNA concentrations microinjected. However, the frequency of Ca2+ spikes was different for each cRNA concentration, with the mean interspike interval decreasing with higher level of the stimulus (FIG. 10B). This data suggests that PLC-zeta, derived from the sperm/testis of various mammals lacks any species-specificity and, once introduced by microinjection, is able to trigger Ca2+ oscillations in heterologous mammalian oocytes. This finding is fully consistent with earlier observations of sperm extracts derived from various sources, including non-mammalian species, each causing Ca2+ oscillations in different mammalian oocytes. FIG. 11 compares the mean interspike intervals for the three different mammalian forms of PLC-zeta at various pipette cRNA concentrations. Microinjecting cRNA for mPLC-zeta, hPLC-zeta and sPLC-zeta all gave rise to Ca2+ oscillations over a range of concentrations from 200 to 2 µg/ml. However, hPLC-zeta was distinct in being able to cause Ca2+ oscillations at the lower concentrations of 0.2-0.02 µg/ml (FIG. 11). This suggests that under the same experimental conditions, the human form of PLC-zeta is more effective at generating Ca2+ oscillations in mouse oocytes than the PLC-zeta from mouse and monkey.

In addition to demonstrating that hPLC-zeta and sPLC-zeta are able to cause Ca2+ oscillations in mouse oocytes (FIGS. 8 and 10), we obtained empirical evidence that hPLC-zeta is more effective at causing Ca$^{2+}$ oscillations than sPLC-zeta and mPLC-zeta (FIG. 11). The minimal amount of hPLC-zeta cRNA required to trigger Ca2+ oscillations was 1-2 orders of magnitude lower (0.2-0.02 g/ml) than the minimally effective dose of mouse or simian PLC-zeta cRNA (2 g/ml). These differences were observed as a consistent feature with different batches of cRNA that were each tested for expression in vitro (data not shown). The superior potency of hPLC-zeta cRNA is therefore likely to represent a genuine feature of the hPLC-zeta protein. Thus, we could predict that there is at least an order of magnitude difference in the sensitivity of mouse oocytes to hPLC-zeta compared with mPLC-zeta. It is not clear why hPLC-zeta exhibits greater virility than mPLC-zeta or sPLC-zeta. Subsequent to stimulating Ca2+ oscillations in mouse oocytes, the human PLC-zeta was also able to trigger development of embryos to the blastocyst stage (FIG. 8). This suggests that hPLC-zeta is able to produce all of the normal events of oocyte activation. However, one feature of the greater efficacy of hPLC-zeta is that high cRNA levels caused very high frequency Ca2+ oscillations in mouse oocytes (FIG. 8A, top trace). At concentrations of cRNA that resulted in Ca2+ oscillations of ~1 spike every 5 minutes, hPLC-zeta was able to effect oocyte activation, but the embryos arrested at the 2-cell stage (FIG. 9A). Previous studies have shown that high frequency Ca2+ oscillations may either lead to apoptosis of oocytes, or to developmental changes in postimplantation embryos. Our data provides the first indication that high frequency Ca$^{2+}$ oscillations can also activate an oocyte, but this non-physiological stimulus leads to arrest during the early cleavage stages.

Expression of hPLCζ-Luciferase and Generation of Ca$^{2+}$ Oscillations in Mouse Oocytes.

Figure 12:
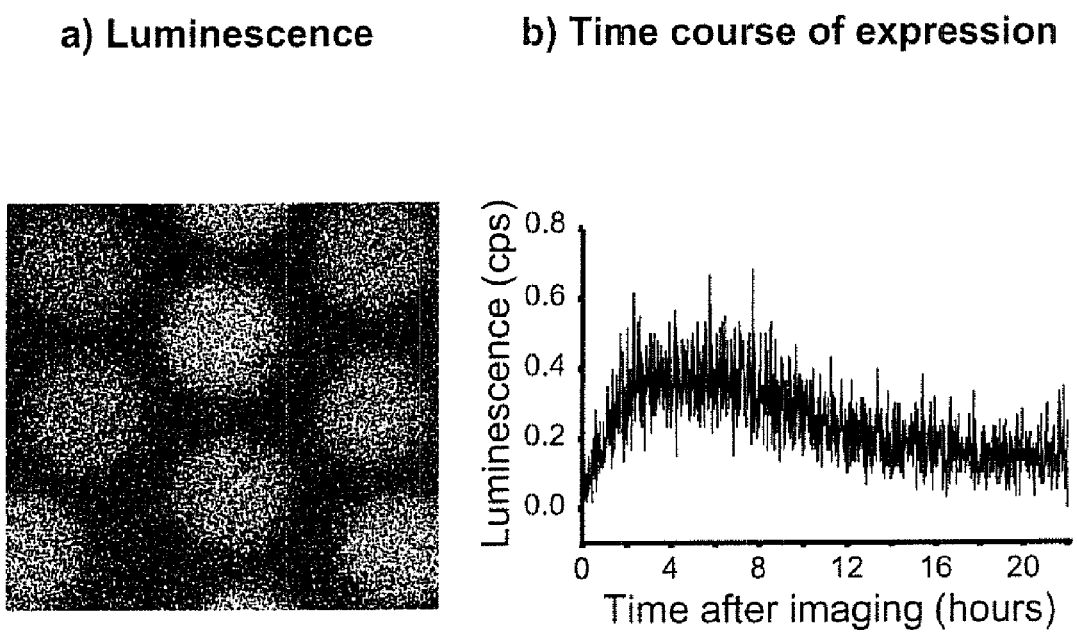
FIG. 12: in a) is shown a luminescence image of typical group of mouse oocytes that had been injected with hPLCζ-luc cRNA and placed in luciferin containing media. The image consists of the integrated photon counts accumulated over a period of 20 hours. In b) the trace illustrates an example of the luminescence (in photon counts per second) from one of mouse oocytes in part (a)

When mouse oocytes were microinjected with hPLCζ-luc cRNA, the luminescence, level (an indicator of luciferase protein concentration) as measured in photon counts per second, started to increase within the first hour and detection of luminescence continued for over a 20 hr period (FIG. 12). FIG. 12*b* shows that the luminescence level gradually accumulated until ~3 hours after cRNA injection when a plateau level of about 0.4 cps was achieved for about 6 hours, after which there was a gradual decline over ~3 hr to a luminescence level of ~0.1 cps. Since Ca$^{2+}$ signaling and oocyte activation generally occurs within 6 hours of injection, in subsequent experiments we measured Ca$^{2+}$ changes in the first 6 hour period post-injection followed by determination of luminescence from the same oocytes for 30 mins in the presence of luciferin to obtain the level of PLCζ-luc protein.

Figure 13:
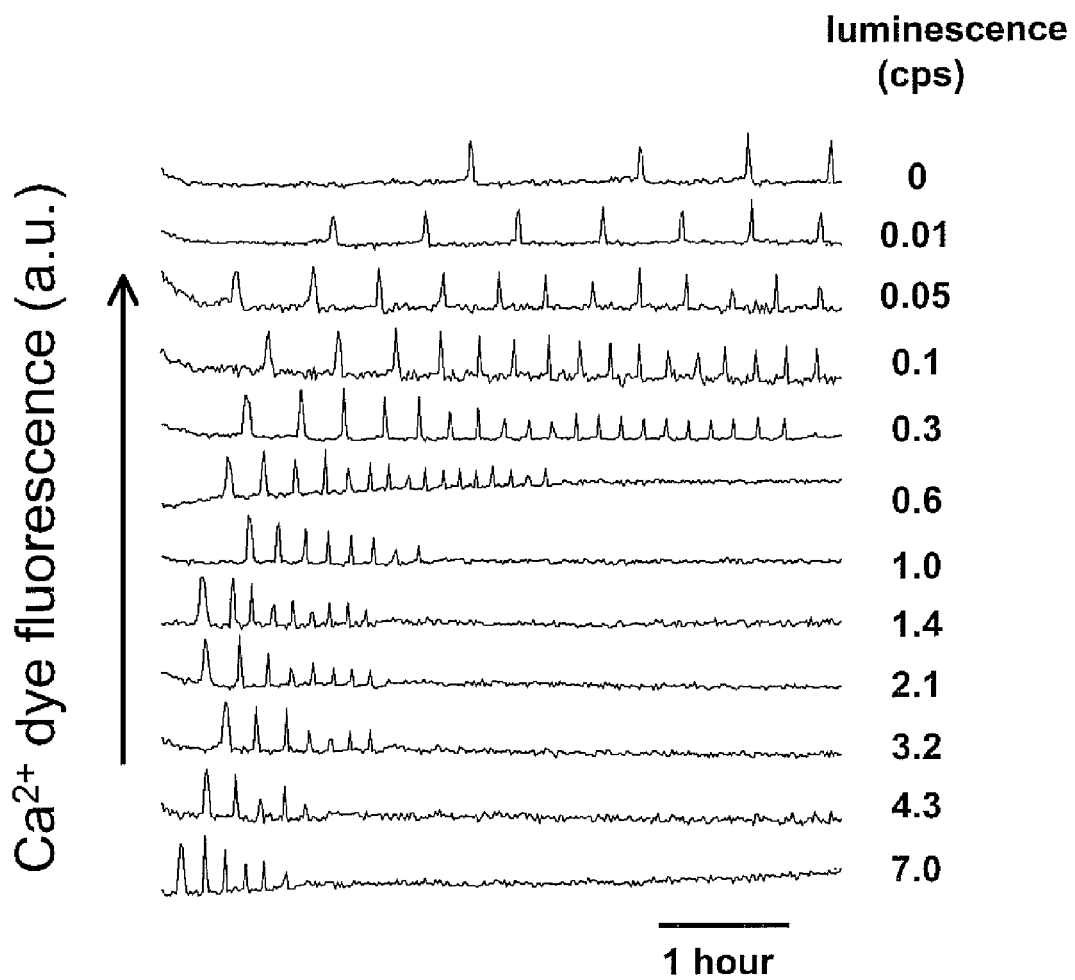
FIG. 13: The pattern of $Ca^{2+}$ oscillations caused by different amounts of hPLCζ-luc expression in individual mouse oocytes. The fluorescence of the $Ca^{2+}$ sensitive dye Oregon Green BAPTA is shown on the y-axis in arbitrary units (a.u.). The $Ca^{2+}$ oscillation pattern is then shown with 12 traces for 12 different oocytes, each with a different level of hPLCζ-luc expression. The luminescence expression levels in counts per second (cps) are indicated for each associated fluorescence trace that indicates the $Ca^{2+}$ levels.
Figure 14:
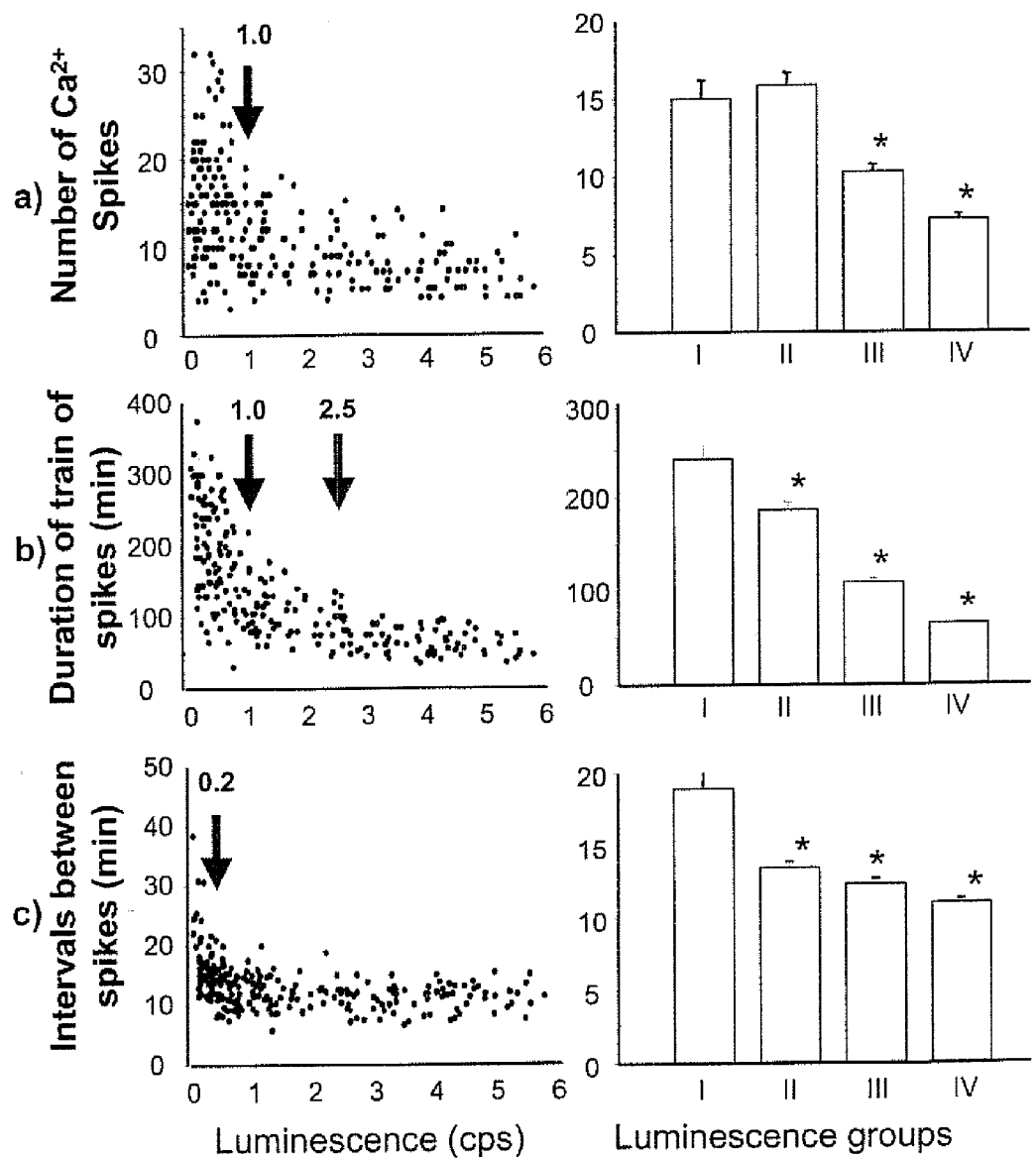
FIG. 14: The relationship $Ca^{2+}$ oscillations and hPLCζ-luc expression. A total of 233 oocytes were imaged, analyzed and plotted as a scatter of dots which show that there were distinct trends in the number, duration and intervals of $Ca^{2+}$ increases that correlated with the hPLCζ-luc expression levels in individual oocytes. According to the changes of calcium oscillation pattern (left), cps 0.2, 1.0 and 2.5 (arrows) were thought to be the transition points and then the levels of hPLC-luc expression were classified into four different ranges; I (0-0.2 cps), II (0.2-1.0 cps), III (1.0-2.5 cps) and IV (2.5-6 cps). (Range I, II, III, IV. right). The bar charts on the right hand side show that there are statistically significant differences pattern of $Ca^{2+}$ oscillations (number of spikes, duration of train, or the intervals between spikes) as the expression levels of hPLCζ-luc increases (the * indicates a significant difference with $P<0.05$)

The effects of different amounts of PLCζ-luc protein on activation are shown in FIG. 13. Various pipette concentrations of 0.05-0.5 µg/µl of hPLCζ-luc cRNA were injected into groups of mouse oocytes. A total of 233 oocytes were microinjected with cRNA and subsequently monitored for Ca$^{2+}$ oscillations and luciferase expression. FIG. 13 shows some typical examples of the distinct patterns of Ca$^{2+}$ oscillations occurring in oocytes due to different levels of hPLCζ-luc expression. Increasing expression levels from 0.01 to 0.3 cps resulted in an enhanced frequency of spikes that was maintained for over 5 hr. However, surprisingly higher expression levels of >0.3 cps caused a cessation of the spikes after 1-3 hr. preceded by a gradual decrease in spike amplitude. The scatter plots in FIG. 14 (left column) illustrate the relationship between the pattern of Ca$^{2+}$ oscillations, as indicated by the number, duration and interval of responses, and the level of luciferase expression. FIG. 14 also presents a histogram analysis (right column) where patterns of oscillations (number, duration and interval) are grouped according to the increasing level (I-IV) of luciferase expression. FIG. 14*a* identifies expression levels I and II as optimal for spike number, whereas the higher levels III and IV cause a reduction. The duration of the train of the spikes also decreases with increasing expression levels, with maximal duration occurring with I (FIG. 14*b*). From FIG. 14*c* it can be seen that interspike interval also is reduced with increasing hPLCζ-luc expression, and hence there is an increase in the frequency of Ca$^{2+}$ oscillations. Since the duration of the whole train of Ca$^{2+}$ oscillations decreases as the frequency increases there is only a small increase in the number of Ca$^{2+}$ spikes in oocytes with high hPLCζ-luc concentrations. Moreover, with high concentrations of hPLCζ-luc, it is evident that the cessation of Ca$^{2+}$ oscillations at high expression levels (e.g. after 1-2 hr in the 1.0 to 7.0 cps traces in FIG. 13) occurs well before the peak of protein expression has occurred (after 3-4 hr in FIG. 12*b*). These data support previous studies suggesting that the pattern of Ca$^{2+}$ oscillations is affected by the amount of PLCζ cRNA injected into each oocyte (Saunders et al., 2002; Cox et al., 2002), but it is now evident that the variation in the pattern of Ca$^{2+}$ oscillations is seen over a relatively small range of PLCζ protein concentrations.

We estimated the protein expression level in these hPLCζ-luc-injected oocytes by comparing the amount of light emitted from embryos on the imaging system with that from oocytes injected with known amounts of luciferase protein. We found that 1 cps of luminescence corresponded to about 250 fg of luciferase protein. Since Ca$^{2+}$ oscillations were triggered with expression levels as low as 0.01 cps, we can estimate that as little as 2.5 fg of hPLCζ-luc protein at 6 hours is associated with Ca$^{2+}$ release. However, since we also know that Ca$^{2+}$ oscillations in these cases started about 1-2 hours after injection (FIG. 13) we can estimate that levels of around 1 fg of hPLCζ-luc are sufficient to trigger Ca$^{2+}$ release in mouse oocytes.

Developmental potential of embryos activated by different levels of hPLCζ-luc. The imaging experiments described above were carried out on a small group of oocytes taken from a larger cohort. For the remaining oocytes we assessed their developmental potential by placing them in KSOM media with cytochalasin B for 6 hours, followed by sustained culture in normal KSOM media. To evaluate the potential of hPLCζ-luc to activate mouse eggs and trigger subsequent development we monitored both pronuclei and blastocyst formation at 6 hours and 96 hours after injection, respectively. We also compared the results from hPLCζ-luc-injected oocytes to the developmental potential of a group of Sr$^{2+}$-activated oocytes that had been collected from the same set of mice on the same day.

Figure 15:
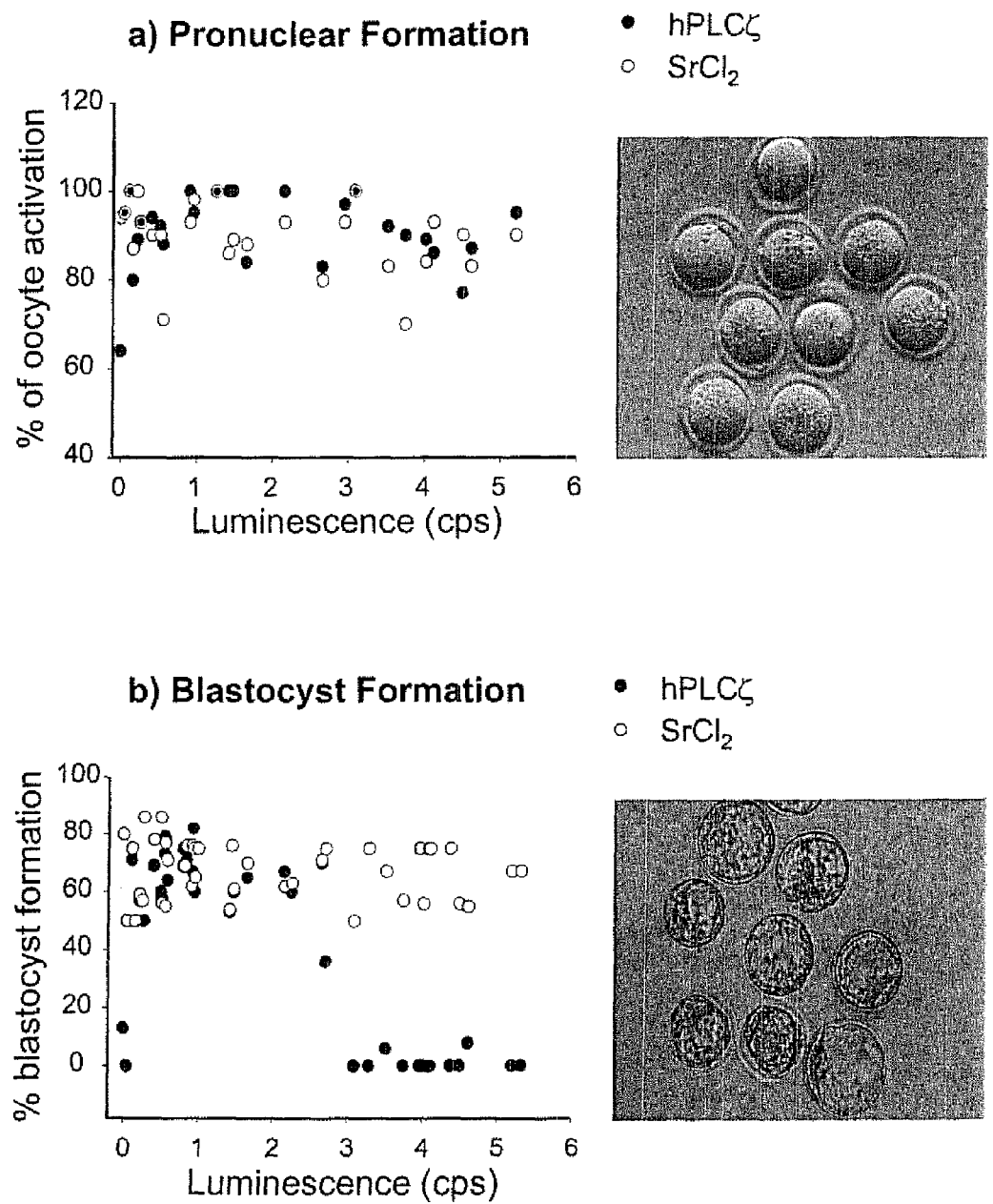
FIG. 15: The effects of hPLCζ-luc cRNA injection on oocyte activation and development. In a) the rate of oocyte activation is scored as pronuclear formation rate divided by the number of injected oocytes. The luminescence level is plotted for each group of oocytes injected with hPLCζ-luc (closed circles). The open circles represent the activation rates for groups of $Sr^{2+}$ treated oocytes that were not luminescent but that were treated in parallel on the same day. In b) the development rate is plotted as the number of blastocysts formed divided by the number of activated oocytes. As with a) this is done for hPLCζ-luc activated embryos at the range of luminescence values plotted on the x-axis (closed circles), and for a parallel group of (non-luminescent) $Sr^{2+}$ activated embryos (open circles). The right hand panels for a) and b) show examples of hPLCζ-luc activated oocytes and blastocysts respectively.

FIG. 15a shows that at a very low level of PLCζ-luc expression (0.05 cps) mouse oocytes can be effectively activated to form pronuclei. Furthermore, over a large range of expression levels (0.05-6 cps) nearly all oocytes formed pronuclei at 6 hr after hPLCζ-luc injection (95.9%). This is comparable to the pronuclei formation efficiency observed for SrCl$_2$ activation (85.7±2.4%), and is also consistent with previous observations showing mouse oocyte activation upon microinjection of various cRNA concentrations of the untagged hPLCζ (Cox et al., 2002). However, we found that the further development of hPLCζ-luc-injected oocytes beyond pronuclei formation at 6 hr was markedly dependent upon the precise level of PLCζ-luc expression.

FIG. 15b shows the rate of development to the blastocyst stage for PLCζ-luc-injected oocytes was >50% (i.e. similar to Sr$^{2+}$-activated oocytes) only when the level of hPLCζ-luc expression was between narrowly defined limits of 0.12 to 2.7 cps. Most notably, when the expression of hPLCζ-luc was greater than 2.7 cps, the embryos all failed to develop into blastocysts. Most of these high hPLCζ-luc expression embryos (>2.7 cps) arrested at the 2-cell stage with only 38% reaching the 4-cell stage. These data show that there is a wide range of concentrations where hPLCζ-luc can fully activate oocytes (i.e. induce pronuclei formation), but that ability to activate in itself does not guarantee that embryos will develop into blastocysts. These observations suggest that only a specific, narrow window of hPLCζ levels is consistent with successful pre-implantation development.

Assessments of Blastocysts Obtained after hPLCζ-luc Injection.

Figure 16:
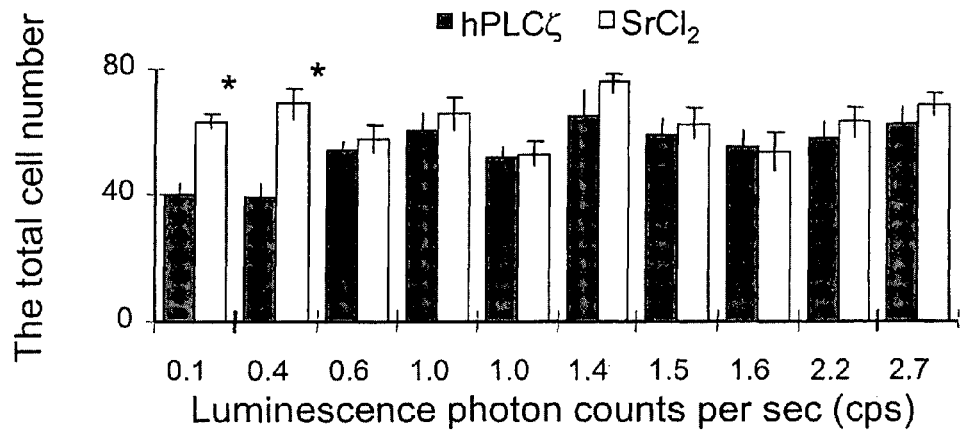
FIG. 16: The distribution of cells in blastocysts analyzed by differentiation staining. The plots in a) show the total cell number of in b) the ratio of ICM cells to trophoblastic cells in blastocyst activated by hPLCζ-luc. Each bar represents a group of embryos that had been activated by a different expression level of hPLCζ-luc as plotted on the x-axis. The number of distribution of cells for each group of $Sr^{2+}$-activated embryos is shown alongside is the parallel PLCζ group. In each experiment, at least 10 blastocysts were analyzed, and the * indicates a significant difference with $P<0.05$. In c) a typical image is show for an hPLCζ-luc activated blastocyst with the ICM cells and trophoblastic cells stained in blue and pink respectively.
Figure 16:
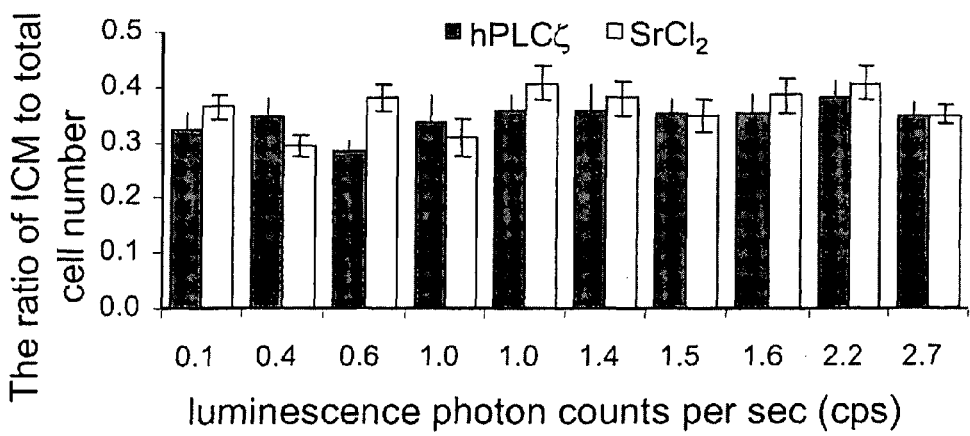
Figure 16:
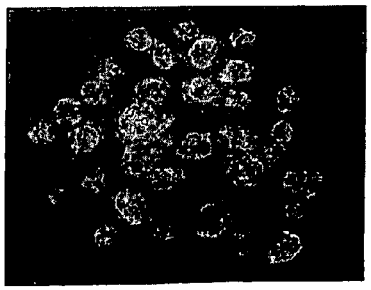

We evaluated the blastocyst embryos obtained from hPLCζ-luc injection by analysis of the total cell number, and the cell number ratio between ICM cells and trophoblast cells within the blastocysts. This was done by differential staining (FIG. 16), which has been widely used to evaluate the quality of blastocysts (Van Soom et al., 2001). We examined blastocysts derived from ten separate experiments in which the expression levels of hPLCζ-luc ranged between 0.1 and 2.7 cps. The data shown in FIG. 16 demonstrates that all blastocysts obtained after PLCζ-luc injection have a similar ratio of cells allocated between the ICM and the trophectoderm, and this ratio is similar to that seen after Sr$^{2+}$-induced oocyte activation (FIG. 16b). However, the total cell number in the blastocysts does show some dependency upon hPLCζ-luc level. With lower levels of expression (0.1 to 0.4 cps), the total cell number is significant lower than that in blastocysts activated by SrCl$_2$ (39.8±3.6 versus 63.6±2.5 for 0.1 cps and 40.4±7.4 versus 68.4±2.6 for 0.4 cps; FIG. 16a). In contrast, blastocysts induced with higher level of hPLCζ-luc expression (cps 0.6-2.7) have the same cell number as that activated with SrCl$_2$ (FIG. 16a). These data suggest that a specific level of PLCζ-luc expression may be required to achieve an optimal number of cells in a blastocyst.

The Effects of Luciferase cRNA Injection.

Figure 17:
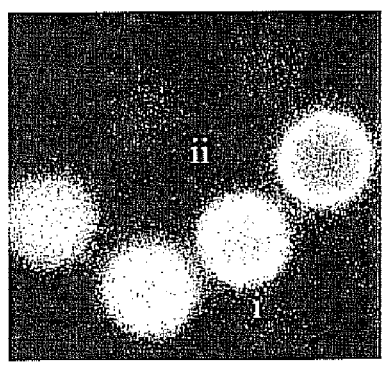
FIG. 17: The development of embryos injected with control luciferase cRNA. The panel a) shows an image of some oocytes eggs injected luciferase RNA (i) that has 23 cps, and with a typical amount of hPLCζ-luc cRNA (ii) which showed 0.83 cps. The image is from integrated counts over 20 minutes. In b) are shown the development rates of embryos activated by either $Sr^{2+}$ or by hPLCζ-luc cRNA (open boxes). In each case development was compared with embryos that had also been injected with excess of luciferase cRNA (filled boxes)
Figure 17:
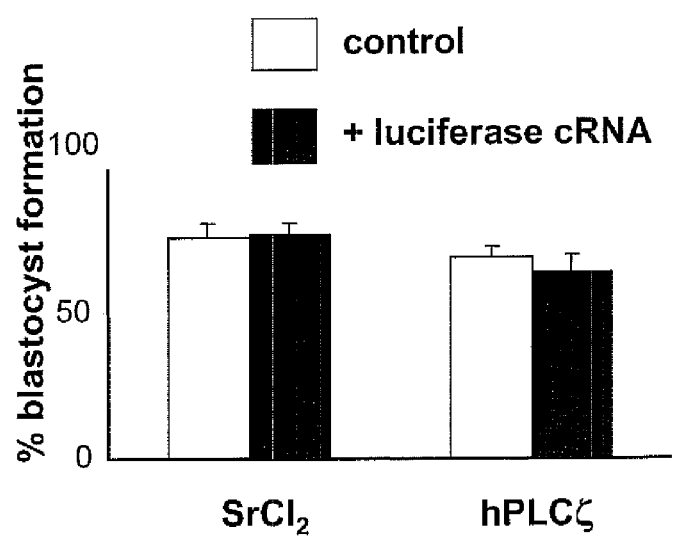

From the experiments described above, it is clear that injection of hPLCζ-luc cRNA can readily activate oocytes but hPLCζ-luc expression can also have a detrimental effect on further development at higher concentrations. In order to establish that these effects are not due to non-specific effects associated with the over-expression of luciferase, or with the injection of exogenous cRNA, we injected mouse oocytes with a control cRNA encoding luciferase protein alone. Mouse oocytes were injected with luciferase cRNA at the same maximal concentration that we used for hPLCζ-luciferase (0.5 μg/μl). These luciferase-injected oocytes were then subsequently activated either by incubation with SrCl$_2$ or by hPLCζ-luc injection (0.1 μg/μl) and cultured in KSOM medium. As shown in FIG. 17a, the average luminescence from these luciferase-injected oocytes was 19±5.2 cps, which is much greater than the maximal signals we obtained with hPLCζ-luc injection alone (FIG. 12). Despite the high level of luciferase expression, we found that the blastocyst formation rate of these oocytes was not different from the control oocytes activated by either SrCl$_2$, or by a single injection of 0.1 μg/μl hPLCζ-luc (FIG. 17b). These results indicate that neither luciferase, nor exogenous RNA injection, can account for any attenuation of development potential of hPLCζ-luc-activated oocytes.

The Effects of hPLCζ-luc in Human Oocytes.

Figure 18:
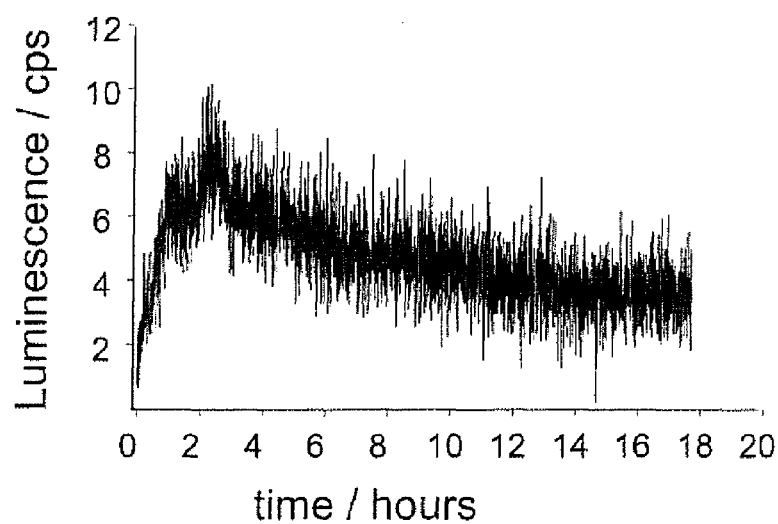
FIG. 18: The Figure shows luminescence (in photon counts per second) following the injection of human PLCζ, tagged with luciferase, in human ooycytes. The difference traces in FIGS. 7A and 7B illustrate that the pattern of expression of human PLCζ was somewhat variable.
Figure 18:
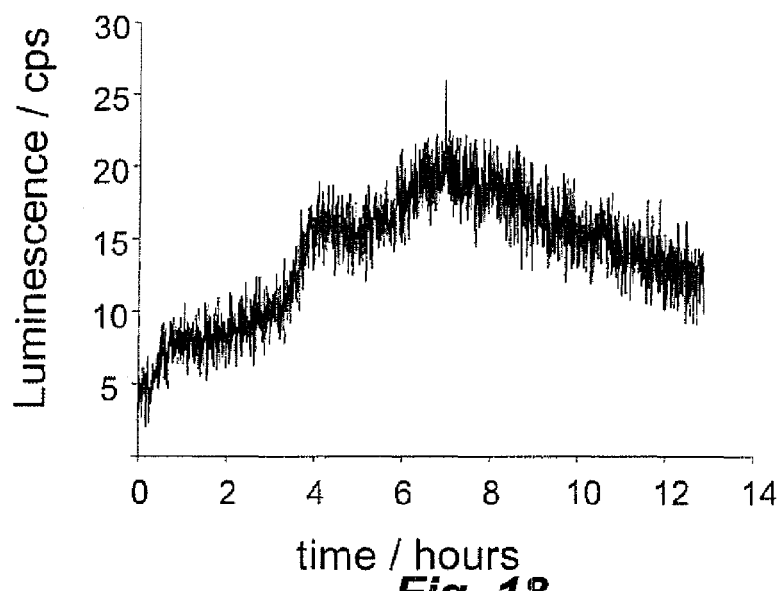
Figure 19:
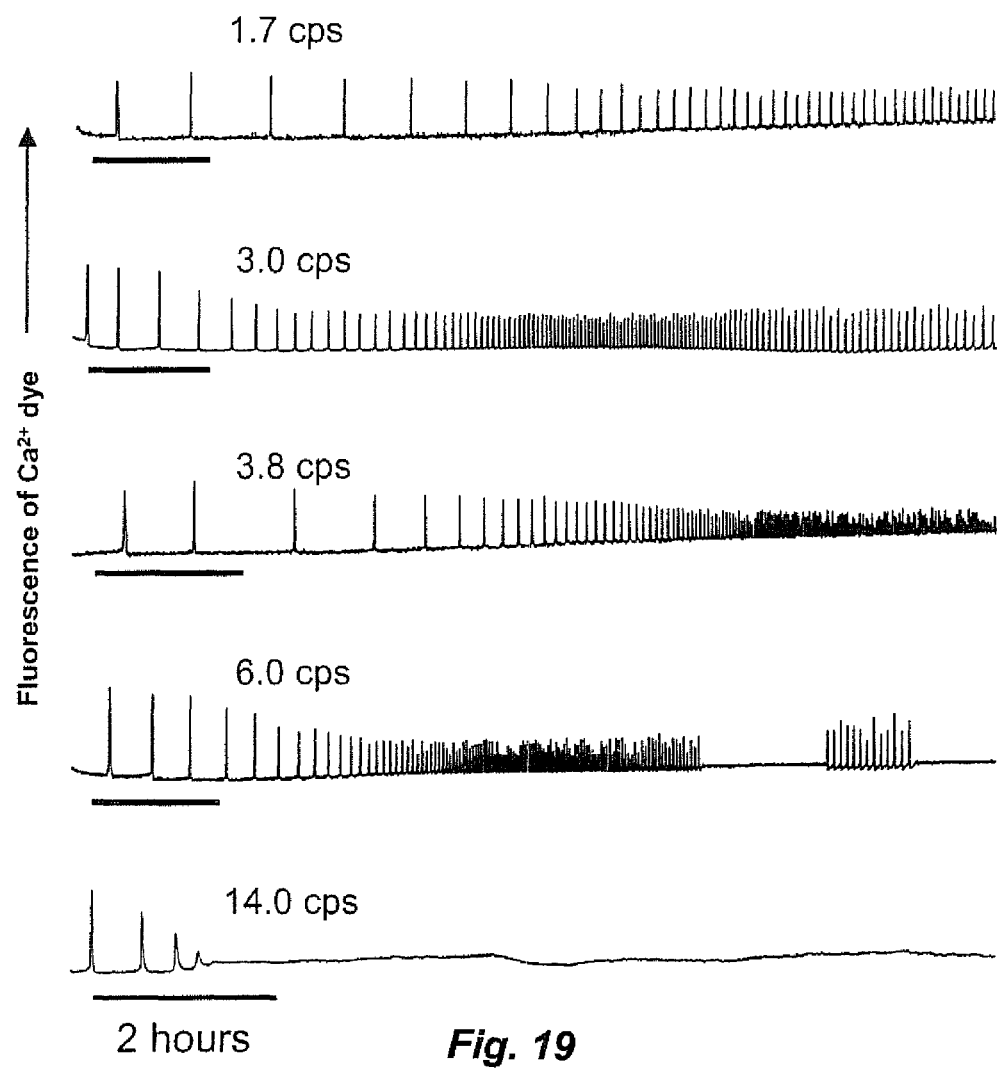
FIG. 19: This shows the pattern of calcium oscillations caused by different amounts of hPLCζ-luc expression in individual human oocytes. The fluorescence of the calcium sensitive dye is shown on the Y-axis. The calcium oscillation pattern is shown in 5 traces for 5 difference human oocytes displaying different levels of hPLCζ-luc expression.
Figure 20:
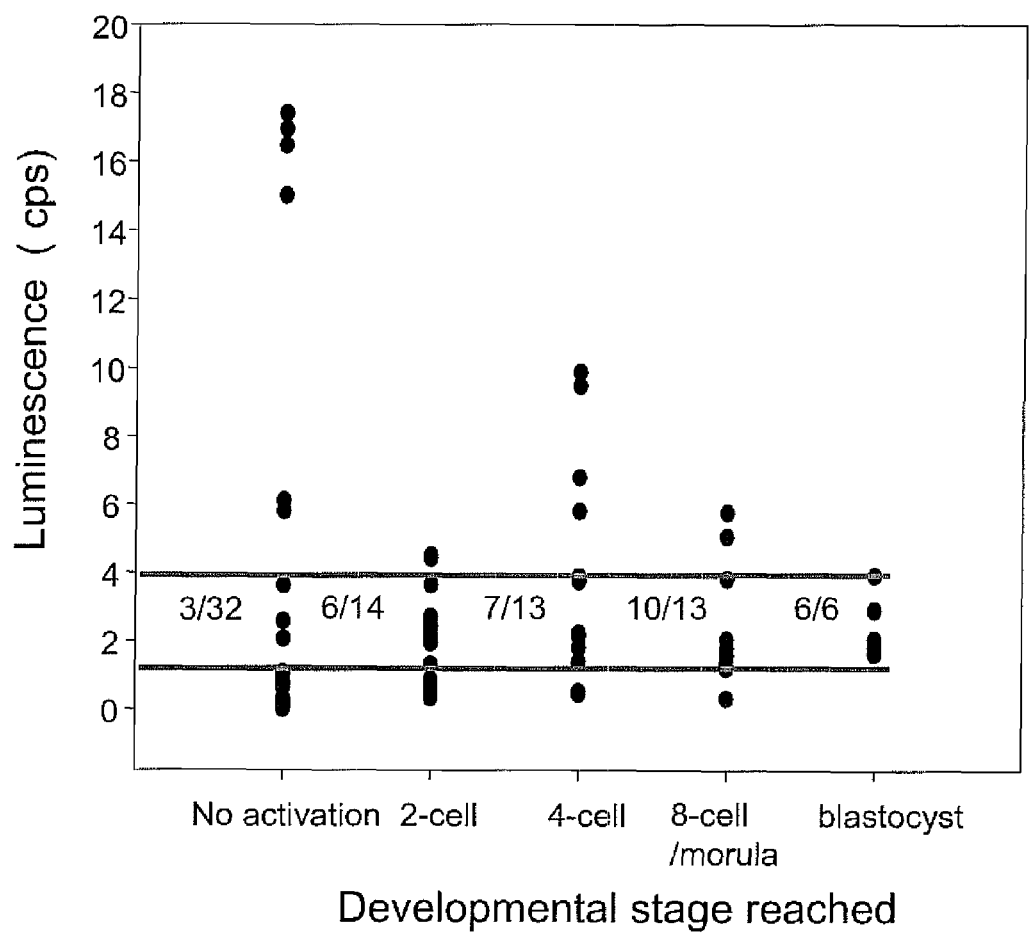
FIG. 20: This shows the development of human eggs expressing different levels of human PLCζ. The development stages are recorded along the X-axis for a range of human eggs each expressing a different level of human PLCζ. In a range of expression level of human PLCζ of 1.2-4 the cleavage, 4 cell, 8 cell and blastocyst rate is 29/32, 23/32, 16/32 and 6/29.

As reported previously for hPLC, injection hPLCζ-luc cRNA leads to the functional expression of hPLCζ-luc protein in human oocytes (FIG. 18). The expression profile of hPLCζ-luc protein was monitored over ~15 hours and it can be seen that there was a steady increase in luminescence suggesting that hPLCζ-luc is progressively synthesized in human oocytes in a similar way to that shown in mouse oocytes. These data suggest that human oocytes behave in a similar manner to model mouse oocytes with regards to the expression of hPLCζ-luc. However, the different traces in FIGS. 18a and 18b illustrate that the pattern of expression was somewhat more variable than that we have seen in mouse oocytes. FIG. 19 illustrates that injection of hPLC-luc cRNA also causes the induction of Ca$^{2+}$ oscillations in human oocytes. The pattern of Ca$^{2+}$ oscillations is shown for 5 different human oocytes displaying different levels of hPLCζ-luc expression. The expression level is indicated in terms of the luminescence level (in counts per second) from each oocyte. As was observed with mouse oocytes, there is a tendency for human oocytes to show higher frequency Ca$^{2+}$ oscillations with higher levels of hPLCζ-luc, as well as a tendency for Ca$^{2+}$ oscillations to stop prematurely when hPLCζ-luc levels were very high (FIG. 19). Again, we noted that there is more variability with human oocytes in the pattern of Ca$^{2+}$ oscillations when compared to mouse oocytes (FIG. 19). Nevertheless, the overall response of human oocytes is consistent with parallel studies in mouse oocytes.

The activation and developmental progression rate of human embryos injected with hPLCζ-luc RNA was monitored in a total of 78 human oocytes (26 fresh, 52 aged oocytes) that were obtained from the IVF clinic over a period of 9 months. The expression level in all embryos was monitored at 15-189 hours after injection of hPLCζ-luc by measuring the luminescence. Only a small proportion of embryos develop past the first few cleavage divisions and progressed to the morula or blastocyst stages (FIG. 19). However, a small number of human embryos activated by hPLCζ-luc did develop up to the blastocyst stage (FIG. 19). It was noticeable that the expression level of hPLCζ-luc determined in these embryos, following activation, was within a narrow range of 1.6-3.9 cps. We have calibrated the levels of luciferase protein in oocytes by injecting known amounts of recombinant luciferase protein. With the microscope and camera system we used, and with 1 mM luciferin, we have determined that 1 cps of luminescence corresponds to about 106 fg of injected luciferase protein in an oocyte. This implies that the amount of human PLCζ protein that is consistent with development to the blastocyst stage is in the range of 170-410 fg (1.6-3.9 cps). Our data, therefore, suggests that this restricted range of hPLCζ expression is a necessary condition for effective development of human embryos to the blastocyst stage. This conclusion is consistent with the extensive studies on mouse oocytes, where we also noted that there was about a 4-fold range of hPLCζ-luc expression level that was permissive for development to the blastocyst stage.

In conclusion, we have herein disclosed and characterized the zeta isoform of phospholipase C and so elucidated a key trigger in the fertilization process.

TABLE 2

Genomic organisation of the human plc-zeta gene
Sequence coordinates and length of exons and introns comprising the human plc-zeta gene localised to chromosome 12p12.3

| Chromosome 12 coordinates | Exon Number | Intron Number | Length (basepairs) |
|---|---|---|---|
| 4443338-4443286 | 1 | | 53 |
| 4443285-4442862 | | 1 | 424 |
| 4442861-4442712 | 2 | | 150 |
| 4442711-4441697 | | 2 | 1015 |
| 4441696-4441564 | 3 | | 133 |
| 4441563-4428887 | | 3 | 12677 |
| 4428886-4428667 | 4 | | 220 |
| 4428666-4424987 | | 4 | 3680 |
| 4424986-4424784 | 5 | | 203 |
| 4424783-4418341 | | 5 | 6443 |
| 4418340-4418195 | 6 | | 146 |
| 4418194-4410669 | | 6 | 7526 |
| 4410668-4410519 | 7 | | 150 |
| 4410518-4407131 | | 7 | 3388 |
| 4407130-4407045 | 8 | | 86 |
| 4407044-4406922 | | 8 | 123 |
| 4406921-4406853 | 9 | | 69 |
| 4406852-4405305 | | 9 | 1548 |
| 4405304-4405151 | 10 | | 154 |
| 4405150-4401621 | | 10 | 3530 |
| 4401620-4401503 | 11 | | 118 |
| 4401502-4400434 | | 11 | 1069 |
| 4400433-4400263 | 12 | | 171 |
| 4400262-4393572 | | 12 | 6691 |
| 4393571-4393443 | 13 | | 129 |
| 4393442-4389634 | | 13 | 3809 |
| 4389633-4389484 | 14 | | 150 |
| 4389483-4388679 | | 14 | 805 |
| 4388678-4388535 | 15 | | 144 |

What is claimed is:

1. A diagnostic method for determining the fertility status of a mammal, comprising determining the amount of a nucleic acid as set forth in SEQ ID NO. 3 or a sequence which hybridizes thereto under stringent conditions, present or absent in a test sample comprising a sperm cell obtained from the mammal;
wherein said stringent conditions comprise incubation at from about 42° C. to about 68° C. in a solution comprising 6×SSC or 6×SSPE and one or more washing steps at 65° C.; and
further wherein the amount of nucleic acid in the test sample is indicative of expression of a phospholipase C (PLC) ζ per sperm cell of less than 170 femtograms or more than 410 femtograms, which amount is indicative that the sperm cell will be unable to stimulate an oocyte to develop to a blastocyst stage and so that the mammal is at risk of infertility.

2. A method according to claim 1, wherein the test sample comprises genomic DNA.

3. The method according to claim 1, wherein the amount of nucleic acid sequence is indicative of expression of a PLC C per sperm cell of less than 150 femtograms or more than 450 femtograms.

* * * * *

UNITED STATES PATENT AND TRADEMARK OFFICE
CERTIFICATE OF CORRECTION

PATENT NO. : 8,709,774 B2  
APPLICATION NO. : 12/122056  
DATED : April 29, 2014  
INVENTOR(S) : Francis Anthony Lai Page 1 of 1

It is certified that error appears in the above-identified patent and that said Letters Patent is hereby corrected as shown below:

In the Claims

Column 64, line 52, please replace "PLCC" with -- PLC $\zeta$

Signed and Sealed this  
Tenth Day of March, 2015

Michelle K. Lee  
*Deputy Director of the United States Patent and Trademark Office*